US009409994B2

(12) United States Patent
Ho et al.

(10) Patent No.: US 9,409,994 B2
(45) Date of Patent: Aug. 9, 2016

(54) HIGH-AFFINITY MONOCLONAL ANTIBODIES TO GLYPICAN-3 AND USE THEREOF

(71) Applicant: The United States of America, as represented by the Secretary, Department of Health and Human Services, Bethesda, MD (US)

(72) Inventors: Mitchell Ho, Urbana, MD (US); Yen T. Phung, Annandale, VA (US); Wei Gao, Rockville, MD (US); Yifan Zhang, Haymarket, VA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 23 days.

(21) Appl. No.: 14/403,896

(22) PCT Filed: May 31, 2013

(86) PCT No.: PCT/US2013/043633
§ 371 (c)(1),
(2) Date: Nov. 25, 2014

(87) PCT Pub. No.: WO2013/181543
PCT Pub. Date: Dec. 5, 2013

(65) Prior Publication Data
US 2015/0147330 A1    May 28, 2015

Related U.S. Application Data

(60) Provisional application No. 61/654,232, filed on Jun. 1, 2012.

(51) Int. Cl.
| C07K 16/30 | (2006.01) |
| A61K 39/395 | (2006.01) |
| G01N 33/68 | (2006.01) |
| A61K 38/45 | (2006.01) |
| A61K 47/48 | (2006.01) |
| G01N 33/574 | (2006.01) |
| A61K 39/00 | (2006.01) |

(52) U.S. Cl.
CPC ............ *C07K 16/3069* (2013.01); *A61K 38/45* (2013.01); *A61K 47/48569* (2013.01); *A61K 47/48638* (2013.01); *C07K 16/30* (2013.01); *C07K 16/303* (2013.01); *G01N 33/57423* (2013.01); *G01N 33/57438* (2013.01); *G01N 33/57449* (2013.01); *G01N 33/57492* (2013.01); *A61K 2039/505* (2013.01); *C07K 2317/24* (2013.01); *C07K 2317/54* (2013.01); *C07K 2317/55* (2013.01); *C07K 2317/56* (2013.01); *C07K 2317/569* (2013.01); *C07K 2317/622* (2013.01); *C07K 2317/73* (2013.01); *C07K 2317/76* (2013.01); *C07K 2317/92* (2013.01); *C12Y 204/02036* (2013.01); *G01N 2333/705* (2013.01); *G01N 2458/00* (2013.01)

(58) Field of Classification Search
CPC ........................................ C07K 16/30–16/3069
See application file for complete search history.

(56) References Cited

U.S. PATENT DOCUMENTS

| 7,871,613 | B2 * | 1/2011 | Kinoshita | ............ C07K 16/303 424/130.1 |
| 7,919,086 | B2 * | 4/2011 | Nakano | ................ C07K 16/303 424/133.1 |
| 9,206,257 | B2 * | 12/2015 | Ho | ..................... C07K 16/3092 |

FOREIGN PATENT DOCUMENTS

| EP | 1 411 118 | 4/2004 |
| EP | 1 541 680 | 6/2005 |
| EP | 1 674 111 | 6/2006 |
| EP | 2 169 404 | 3/2010 |
| EP | 2 196 541 | 6/2010 |
| EP | 2 270 509 | 1/2011 |
| EP | 2 275 135 | 1/2011 |
| WO | WO 2007/047291 | 4/2007 |
| WO | WO 2009/012394 | 1/2009 |
| WO | WO 2012/145469 | 10/2012 |

OTHER PUBLICATIONS

Carter, "Potent Antibody Therapeutics by Design," *J. Immunol.*, vol. 6:343-357, 2006.
Davies et al., "Affinity Improvement of Single Antibody VH Domains: Residues in all Three Hypervariable Regions Affect Antigen Binding," *Immunotechnology*, vol. 2:169-179, 1996.
Feng et al., "Therapeutically Targeting Glypican-3 via a Conformation-Specific Single-Domain Antibody in Hepatocellular Carcinoma," *Proc., Natl. Acad. Sci. USA*, vol. 110:E1083-E1091, 2013.
Ho et al., "Glypican-3: A New Target for Cancer Immunotherapy," *Eur. J. Cancer*, vol. 47:333-338, 2011.
Ho et al., "Advances in Liver Cancer Antibody Therapies: A Focus on Glypican-3 and Mesothelin," *BioDrugs* 25(5):275-284, 2011.

(Continued)

*Primary Examiner* — Jessica H Roark
(74) *Attorney, Agent, or Firm* — Klarquist Sparkman, LLP

(57) ABSTRACT

Described herein is the identification of a panel of high affinity monoclonal antibodies that bind GPC3. The disclosed antibodies recognize native GPC3 on the surface of cancer cells, as well as soluble GPC3. The highest affinity antibody (YP7) was further characterized and shown to be highly sensitive in that it was capable of detecting cancer cells with low expression of GPC3. YP7 also exhibited significant HCC tumor growth inhibition in vivo. Immunotoxins comprising the antibodies disclosed herein fused to PE38 exhibited very high binding affinity for GPC3-expressing cells and significantly inhibited GPC3-expressing cancer cell growth. Thus, the high-affinity monoclonal antibodies disclosed herein can be used for the diagnosis and treatment of GPC3-expressing cancers.

33 Claims, 23 Drawing Sheets

(56) References Cited

OTHER PUBLICATIONS

Holt et al., "Domain Antibodies: Proteins for Therapy," *Trends Biotechnol.*, vol. 21:484-490, 2003.

Ishiguro et al., "Anti-Glypican 3 Antibody as a Potential Antitumor Agent for Human Liver Cancer," *Cancer Res.*, vol. 68:9832-9838, 2008.

Li et al., "Validation of Glypican-3-Specific scFv Isolated from Paired Display/Secretory Yeast Display Library," *BMC Biotechnol.*, vol. 12:23, 2012.

Nakano et al., "Anti-Glypican 3 Antibodies Cause ADCC Against Human Hepatocellular Carcinoma Cells," *Biochem. Biophys. Res. Commun.*, vol. 378:279-284, 2009.

Phung et al., "High-Affinity Monoclonal Antibodies to Cell Surface Tumor Antigen Glypican-3 Generated through a Combination of Peptide Immunization and Flow Cytometry Screening," *mAbs*, vol. 4:592-599, 2012.

Wark et al., "Latest Technologies for the Enhancement of Antibody Affinity," *Adv. Drug Deliv. Rev.*, vol. 58:657-670, 2006.

\* cited by examiner

FIG. 1B
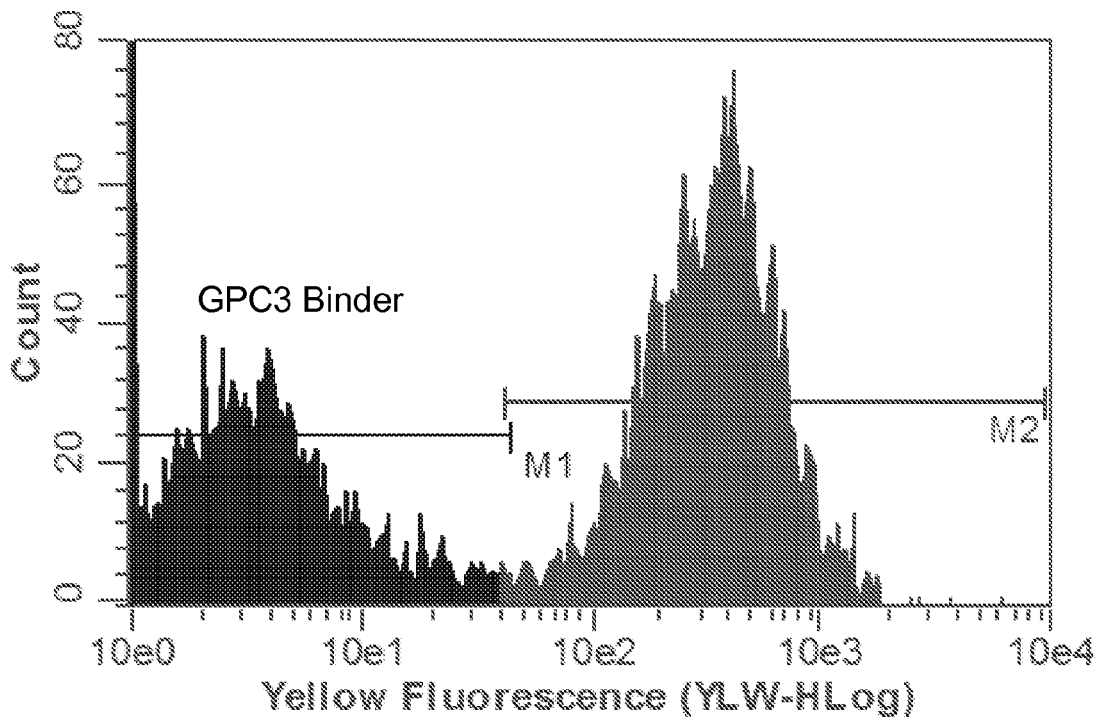
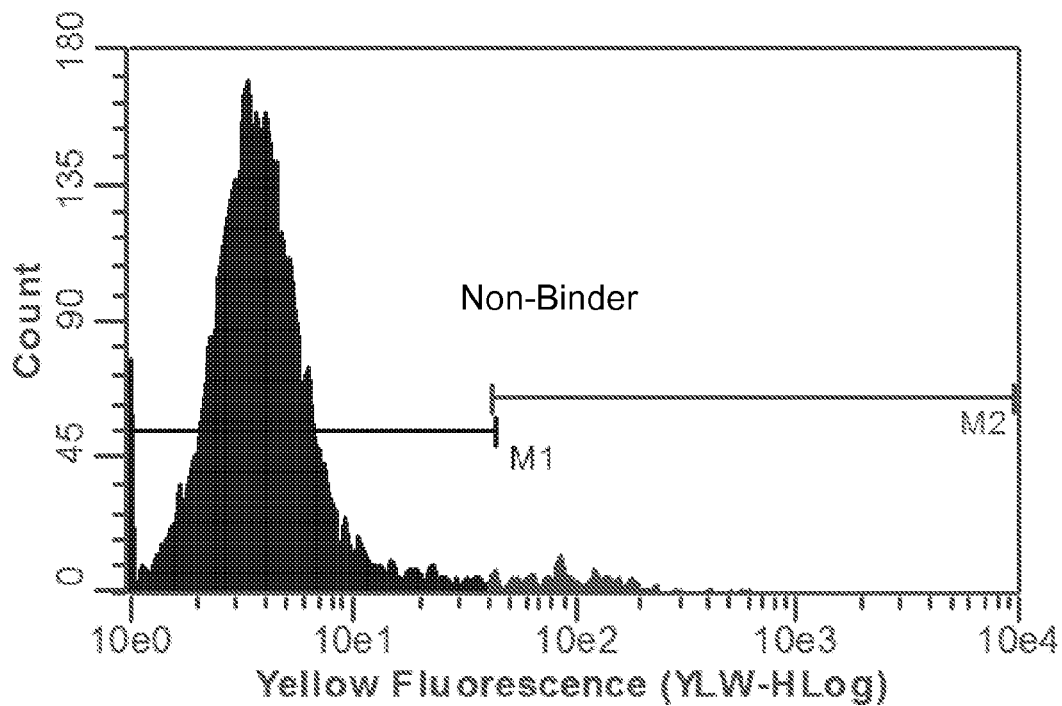

FIG. 3A
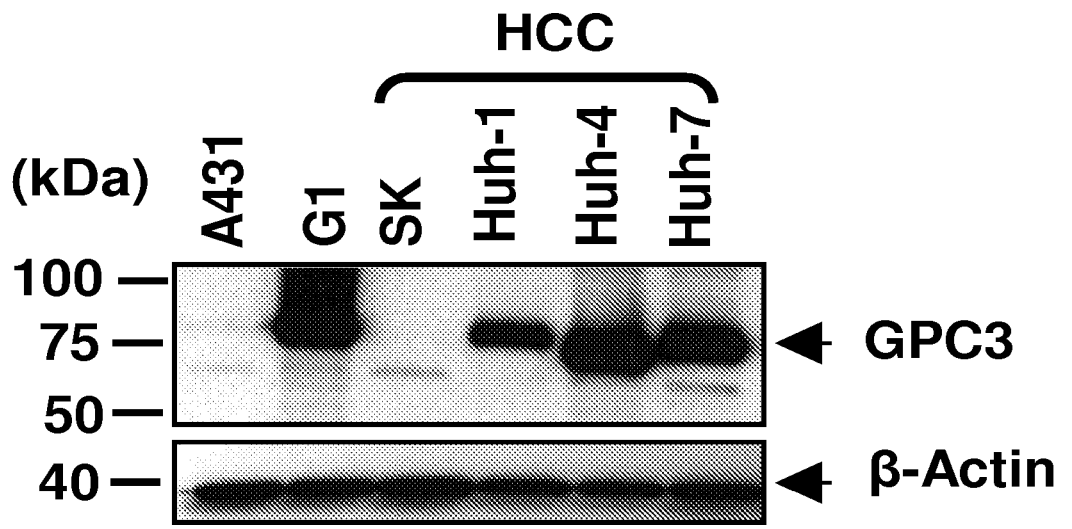
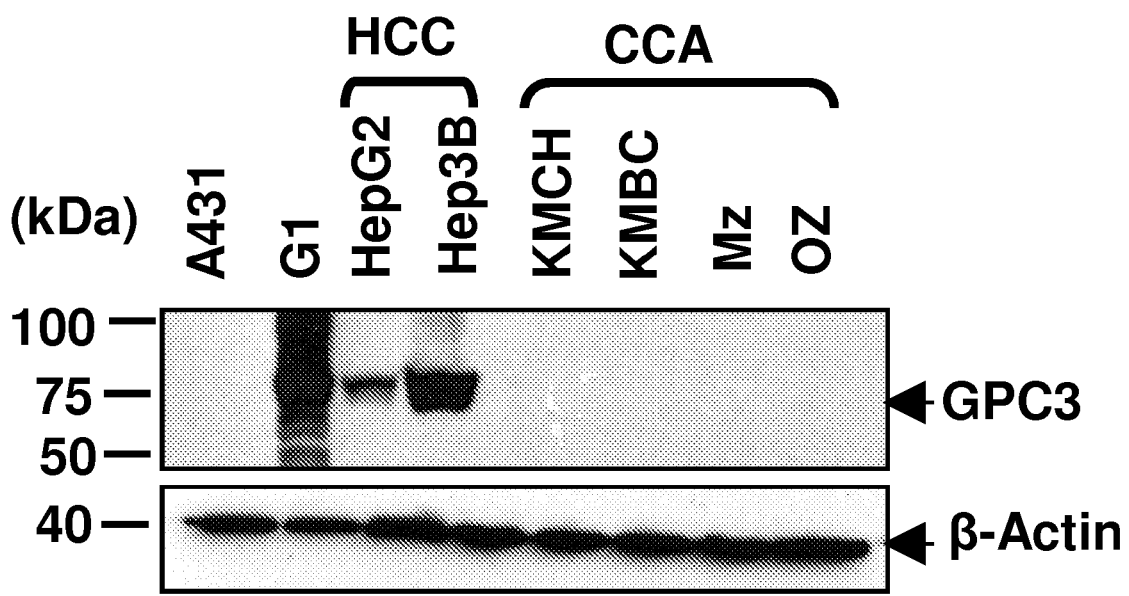

FIG. 5

```
YP6_VH_clone4   GAGGTGCAGCTTGTTGGAAGTGGTGGAGGATTGGTGCAGCCTGAAGGGTCATTGAAACTC 60
YP6_VH_clone7   GAGGTGCAGCTTGTTGGAAGTGGTGGAGGATTGGTGCAGCCTGAAGGGTCATTGAAACTC 60
YP8_VH          GAGGTGCAGCTTGTTGGAAGTGGTGGAGGATTGGTGCAGCCTGAAGGGTCATTGAAACTC 60
YP7_VH          GAGGTGCAGCTTGTTGAGACTGGTGGAGGAATGGTGCAGCCTGAAGGGTCATTGAAACTC 60
YP9_VH          GAGGTCCAGCTTGTTGAGACTGGTGGAGGATTGGTGCAGCCTAAAGGGTCATTGAAACTC 60
YP9.1_VH        GAGGTGCAGCTTGTTGAGACTGGCGGAGGATTGGTGCAGCCTGAAGGGTCATTGAAACTC 60
                ***** ********** * *** ****** *********** *****************

YP6_VH_clone4   TCATGTGCAGCCTCTGGATTCACCTTCAAGACCAATGCCATGAACTGGGTCCGCCAGGCT 120
YP6_VH_clone7   TCATGTGCAGCCTCTGGATTCACCTTCAAGACCAATGCCATGAACTGGGTCCGCCAGGCT 120
YP8_VH          TCATGTGCAGCCTCTGGATTCACCTTCAAGACCAATGCCATGAACTGGGTCCGCCAGGCT 120
YP7_VH          TCATGTGCAGCCTCTGGATTCACCTTCAATAAGAATGCCATGAATTGGGTCCGCCAGGCT 120
YP9_VH          TCATGTGCAGCCTCTGGATTCACCTTCAATACCAATGCCATGAACTGGGTCCGCCAGGCT 120
YP9.1_VH        TCATGTGCAACGTCTGGATTCAACTTCAATACCAATGCCATGAACTGGGTCCGCCAGGCT 120
                ********* * ********** ****** * ************ ***************

YP6_VH_clone4   CCAGGAAAGGGTTTGGAATGGGTTGCTCGCATAAGAAATAAAACTAATAATTATGCAACA 180
YP6_VH_clone7   CCAGGAAAGGGTTTGGAATGGGTTGCTCGCATAAGAAATAAAACTAATAATTATGCAACA 180
YP8_VH          CCAGGAAAGGGTTTGGAATGGGTTGCTCGCATAAGAAATAAAACTAATAATTATGCAACA 180
YP7_VH          CCAGGAAAGGGTTTGGAATGGGTTGCTCGCATAAGAAATAAAACTAATAATTATGCAACA 180
YP9_VH          CCAGGAAAGGGTTTGCAATGGGTTGCTCGCGTAAGAAATAAAACTAATAATTATGCAACA 180
YP9.1_VH        CCAGGAAAGGGTTTGGAATGGGTTGCTCGCGTAAGAAATAAAACTAATAATTATGCAACA 180
                *************** ************* ******************************

YP6_VH_clone4   TATTATGCCGACTCAGTGAAAGACAGGTTCACCATCTCCAGAGATGATTCACAAAGCATG 240
YP6_VH_clone7   TATTATGCCGACTCAGTGAAAGACAGGTTCACCATCTCCAGAGATGATTCACAAAGCATG 240
YP8_VH          TATTATGCCGACTCAGTGAAAGACAGGTTCACCATCTCCAGAGATGATTCACAAAGCATG 240
YP7_VH          TATTATGCCGATTCAGTGAAAGCCAGGTTTACCATCTCCAGAGATGATTCACAAAGCATG 240
YP9_VH          TATTATGCCGATTCCGTGAAAGACAGGTTCACCATCTCCAGAGATGATTCACAAAGCATG 240
YP9.1_VH        TATTATGCCGATTCAGTGAAAGACAGGTTCACCATCTCCAGAGATGATTCACAAAGAATG 240
                *********** ** ** ****** ***** *************************** ***

YP6_VH_clone4   CTCTATCTGCAAATGAACAACTTGAAAACTGAAGACACAGCCATGTATTTCTGTGTGGCC 300
YP6_VH_clone7   CTCTATCTGCAAATGAACAACTTGAAAACTGAAGACACAGCCATGTATTTCTGTGTGGCC 300
YP8_VH          CTCTATCTGCAAATGAACAACTTGAAAACTGAAGACACAGCCATGTATTTCTGTGTGGCC 300
YP7_VH          CTCTATCTGCAAATGAACAACTTGAAAATTGAGGACACAGCCATGTACTATTGTGTGGCT 300
YP9_VH          CTCTATCTGCAAATGAACAACTTGAAAACTGAAGACACGGCCATTTATTACTGTGTGGGG 300
YP9.1_VH        GTCTTTCTGCAAATGAATAACTTGAAAACTGAGGACACAGCCATCTATTACTGTGTGGCG 300
                 *** ************ ********** *** ***** ***** *  * *******

YP6_VH_clone4   GGTAACTCGTTTGCTTACTGGGGCCAGGGGACTCTGGTCACTGTCTCTGCA 351
YP6_VH_clone7   GGTAACTCGTTTGCTTACTTGGGCCAGGGGACTCTGGTCACTGTCTCTGCA 351
YP8_VH          GGTAACTCGTTTGCTTACTGGGGCCAGGGGACTCTGGTCACTGTCTCTGCA 351
YP7_VH          GGTAACTCGTTTGCTTACTGGGGCCAAGGGACTCTGGTCACTGTCTCTGCA 351
YP9_VH          GGTAACTCGTTTGCTTACTGGGGCCAAGGGACTCTGGTCACTGTCTCTGCA 351
YP9.1_VH        GGGAACTCGTTTGCTTATTGGGGCCAAGGGACTCTGGTCACTGTCTCTCCT 351
                ** ************** * ***** *********************   *

KABAT CDRs
IMGT CDRs
```

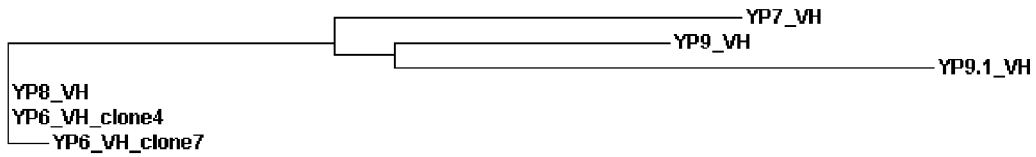

FIG. 6

```
                              CDR1                        CDR2
YP6_VH_clone4  EVQLVGSGGGLVQPEGSLKLSCAAS GFTFKTNAMNWVRQAPGKGLEWVAR IRNKTNNYAT  60
YP6_VH_clone7  EVQLVGSGGGLVQPEGSLKLSCAAS GFTFKTNAMNWVRQAPGKGLEWVAR IRNKTNNYAT  60
YP8_VH         EVQLVGSGGGLVQPEGSLKLSCAAS GFTFKTNAMNWVRQAPGKGLEWVAR IRNKTNNYAT  60
YP7_VH         EVQLVETGGGMVQPEGSLKLSCAAS GFTFNKNAMNWVRQAPGKGLEWVAR IRNKTNNYAT  60
YP9_VH         EVQLVETGGGLVQPKGSLKLSCAAS GFTFNTNAMNWVRQAPGKGLQWVAR VRNKTNNYAT  60
YP9.1_VH       EVQLVETGGGLVQPEGSLKLSCATS GFNFNTNAMNWVRQAPGKGLEWVAR VRNKTNNYAT  60
                ****  ***:***:*********:***  *:   **************** :****:********

CDR3
YP6_VH_clone4  YYADSVKDRFTISRDDSQSMLYLQMNNLKTEDTAMYFC VAGNSFAY WGQGTLVTVSA  117
YP6_VH_clone7  YYADSVKDRFTISRDDSQSMLYLQMNNLKTEDTAMYFC VAGNSFAY LGQGTLVTVSA  117
YP8_VH         YYADSVKDRFTISRDDSQSMLYLQMNNLKTEDTAMYFC VAGNSFAY WGQGTLVTVSA  117
YP7_VH         YYADSVKARFTISRDDSQSMLYLQMNNLKIEDTAMYYC VAGNSFAY WGQGTLVTVSA  117
YP9_VH         YYADSVKDRFTISRDDSQSMLYLQMNNLKTEDTAIYYC VGGNSFAY WGQGTLVTVSA  117
YP9.1_VH       YYADSVKDRFTISRDDSQRMVFLQMNNLKTEDTAIYYC VAGNSFAY WGQGTLVTVSP  117
                ******  **********  *::*******  ****:*:**  ******  *********.

KABAT CDRs
IMGT CDRs
```

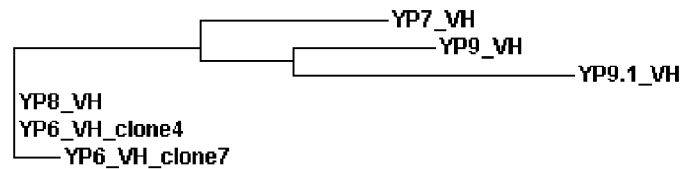

FIG. 7A

```
YP6_VL         GACATTGTGATGTCACAGTCTCCATCCTCCCTAGCTGTGTCAGTTGGAGAGAAGGTTACT 60
YP8_VL         GACATTGTGATGTCACAGTCTCCATCCTCCCTAGCTGTGTCAGTTGGAGAGAAGGTTACT 60
YP9_VL_clone9  GACATTGTGATGTCCCAGTCTCCATCCTCCCTAGCTGTGTCAGTTGGAGAGAAGGTTACT 60
YP9_VL_clone1  GACATTGTGATGTCCCAGTCTCCATCCTCCCTAGCTGTGTCAGTTGGAGAGAAGGTTACT 60
YP9_VL_clone10 GACATTGTGATGTCCCAGTCTCCATCCTCCCTAGCTGTGTCAGTTGGAGAGAAGGTTACT 60
YP9.1_VL       GACATTGTGATGTCACAGTCTCCATCCTCCCTAGCTGTGTCAGTTGGAGAGAGGGTTACT 60
YP7_VL         GACATTGTGATGTCACAGTCTCCATCCTCCCTAGTTGTGTCAATTGGAGAGAAGGTTACT 60
               ************** ****************** ****** ********* *******

YP6_VL         GTGAACTGCAAGTCCAGTCAGAGCCTTTTATATAGTAACAATCAAAAGAACTACTTGGCC 120
YP8_VL         GTGAACTGCAAGTCCAGTCAGAGCCTTTTATATAGTAACAATCAAAAGAACTACTTGGCC 120
YP9_VL_clone9  ATGAGCTGCAAGTCCAGTCAGAGCCTTTTATATAGTAACAATCAAAAGAACTACTTGGCC 120
YP9_VL_clone1  ATGAGCTGCAAGTCCAGTCAGAGCCTTTTATATAGTAACAATCAAAAGAACTACTTGGCC 120
YP9_VL_clone10 ATGAGCTGCAAGTCCAGTCAGAGCCTTTTATATAGTAACAATCAAAAGAACTACTTGGCC 120
YP9.1_VL       ATGAACTGCAAGTCCAGTCAGAGTCTTTTATATAGTAGCAATCAAAAGAACTACTTGGCC 120
YP7_VL         ATGACCTGCAAGTCCAGTCAGAGCCTTTTATATAGCAGCAATCAAAAGAACTACTTGGCC 120
               *** ***************** * *********** * ********************

YP6_VL         TGGTACCAGCAGAAACCAGGGCAGTCTCCTAAACTGCTGATTTACTGGGCATCAACTAGG 180
YP8_VL         TGGTACCAGCAGAAACCAGGGCAGTCTCCTAAACTGCTGATTTACTGGGCATCAACTAGG 180
YP9_VL_clone9  TGGTACCACCAGAAACCAGGGCAGTCTCCTAAACTGCTGATTTACTGGGCATCCACTAGG 180
YP9_VL_clone1  TGGTACCACCAGAAACCAGGGCAGTCTCCTAAACTGCTGATTTACTGGGCATCCACTAGG 180
YP9_VL_clone10 TGGTACCACCAGAAACCAGGGCAGTCTCCTAAACTGCTGATTTACTGGGCATCCACTAGG 180
YP9.1_VL       TGGTACCAGCAGAAACCAGGGCAGTCTCCTAAACTGCTGATTTACTGGGCATCCACTAGG 180
YP7_VL         TGGTACCAACAGAAACCAGGGCAGTCTCCTAAACTGCTGATTTACTGGGCATCCAGTAGG 180
               ******** ************************************** * ****

YP6_VL         GAATATGGGGTCCCTGATCGCTTCACAGGCAGTGGATCTGGGACAGATTTCACTCTCACC 240
YP8_VL         GAATATGGGGTCCCTGATCGCTTCACAGGCAGTGGATCTGGGACAGATTTCACTCTCACC 240
YP9_VL_clone9  GAATCTGGGGTCCCTGATCGCTTCACAGGCAGTGGATCTGGGACAGATTTCACTCTCACC 240
YP9_VL_clone1  GAATCTGGGGTCCCTGATCGCTTCACAGGCAGTGGATCTGGGACAGATTTCACTCTCACC 240
YP9_VL_clone10 GAATCTGGGGTCCCTGATCGCTTCACAGGCAGTGGATCTGGGACAGATTTCACTCTCACC 240
YP9.1_VL       GAATCTGGGGTCCCTGATCGCTTCACAGGCAGTGTATCTGGGACAGATTTCACTCTCACC 240
YP7_VL         GAATCTGGGGTCCCTGATCGCTTCACAGGCAGTGGATCTGGGACAGATTTCACTCTCACC 240
               **** ***************************** ************************

YP6_VL         ATCAGCAGTGTGAAGGCTGAAGACCTGGCAGTTTATTACTGTCAGCAATATTATAACTAT 300
YP8_VL         ATCAGCAGTGTGAAGGCTGAAGACCTGGCAGTTTATTACTGTCAGCAATATTATAACTAT 300
YP9_VL_clone9  ATCAGCAGTGTGAAGGCTGAAGACCTGGCAGTTTATTACTGTCAGCAATATTATAGCTAT 300
YP9_VL_clone1  ATCAGCAGTGTGAAGGCTGAAGACCTGGCAGTTTATTACTGTCAGCAATATTATAGCTAT 300
YP9_VL_clone10 ATCAGCAGTGTGAAGGCTGAAGACCTGGCAGTTTATTACTGTCAGCAATATTATATCTAT 300
YP9.1_VL       ATCAGCAGTGTGAAGGCTGAAGACCTGGCAGTTTATTACTGTCAGCAATATTATAACTAT 300
YP7_VL         ATCAGCAGTGTGAAGGCTGAAGACCTGGCAGTTTATTACTGTCAGCAATATTATAACTAT 300
               ****************************************************** ****
```

FIG. 8

```
YP6             DIVMSQSPSSLAVSVGEKVTVNCKSSQSLLYSNNQKNYLAWYQQKPGQSPKLLIYWASTR 60
YP8_VL          DIVMSQSPSSLAVSVGEKVTVNCKSSQSLLYSNNQKNYLAWYQQKPGQSPKLLIYWASTR 60
YP9_VL_clone9   DIVMSQSPSSLAVSVGEKVTMSCKSSQSLLYSNNQKNYLAWYHQKPGQSPKLLIYWASTR 60
YP9_VL_clone1   DIVMSQSPSSLAVSVGEKVTMSCKSSQSLLYSNNQKNYLAWYHQKPGQSPKLLIYWASTR 60
YP9_VL_clone10  DIVMSQSPSSLAVSVGEKVTMNCKSSQSLLYSNNQKNYLAWYQQKPGQSPKLLIYWASTR 60
YP9.1_VL        DIVMSQSPSSLAVSVGERVTMNCKSSQSLLYSNNQKNYLAWYQQKPGQSPKLLIYWASTR 60
YP7_VL          DIVMSQSPSSLVVSIGEKVTMTCKSSQSLLYSSNQKNYLAWYQQKPGQSPKLLIYWASSR 60
                **********::*:**:***.*****:***********:**********:*****:*

YP6             EYGVPDRFTGSGSGTDFTLTISSVKAEDLAVYYCQQYYNYPLTFGAGTKLELK 113
YP8_VL          EYGVPDRFTGSGSGTDFTLTISSVKAEDLAVYYCQQYYNYPLTFGAGTKLELK 113
YP9_VL_clone9   ESGVPDRFTGSGSGTDFTLTISSVKAEDLAVYYCQQYYSYPLTFGAGTKLELK 113
YP9_VL_clone1   ESGVPDRFTGSGSGTDFTLTISSVKAEDLAVYYCQQYYSYPLTFGAGTKLELK 113
YP9_VL_clone10  ESGVPDRFTGSGSGTDFTLTISSVKAEDLAVYYCQQYIYPLTFGAGTKLEIK 113
YP9.1_VL        ESGVPDRFTGSGSGTDFTLTISSVKAEDLAVYYCQQYYNYPLTFGAGTKLELK 113
YP7_VL          ESGVPDRFTGSVSGTDFTLTISSVKAEDLAVYYCQQYYNYPLTFGAGTKLELK 113
                *.*********.***********************.:.********* ***

KABAT CDRs
IMGT CDRs
```

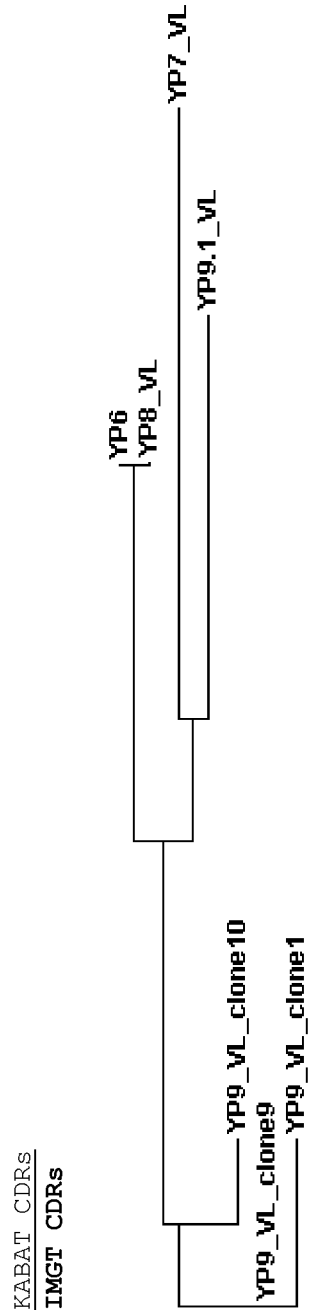

FIG. 9A

```
atggaggtgcagcttgttgagactggtggaggaatggtgcagcctgaagggtcattg
 M  E  V  Q  L  V  E  T  G  G  G  M  V  Q  P  E  G  S  L
aaactctcatgtgcagcctctggattcaccttcaataagaatgccatgaattgggtccgc
 K  L  S  C  A  A  S  G  F  T  F  N  K  N  A  M  N  W  V  R
caggctccaggaaagggtttggaatgggttgctcgcataacaaataaaactaataattat
 Q  A  P  G  K  G  L  E  W  V  A  R  I  R  N  K  T  N  N  Y
gcaacatattatgccgattcagtgaaagccaggtttaccatctccagagatcattcacaa
 A  T  Y  Y  A  D  S  V  K  A  R  F  T  I  S  R  D  D  S  Q
agcatgctctatctgcaaatgaacaactgaaaattgaggacacagccatgtactattgt
 S  M  L  Y  L  Q  M  N  N  L  K  I  E  D  T  A  M  Y  Y  C
gtggctggtaactgttttgcttactggggccaagggactctggtcactgtctctgcaggc
 V  A  G  N  S  F  A  Y  W  G  Q  G  T  L  V  T  V  S  A  G
ggaggcggatcagctggtggcggatctggaggtggcggaagcgacattgtgatgtcacag
 G  G  G  S  G  G  G  S  G  G  G  S  D  I  V  M  S  Q
tctccatcctccctagttgtgtcaattggagagaaggttactatgacctgcaagtccagt
 S  P  S  S  L  V  V  S  I  G  E  K  V  T  M  T  C  K  S  S
cagagccttttatatagcagcaatcaaaagaactacttggcctggtaccaacagaaacca
 Q  S  L  L  Y  S  S  N  Q  K  N  Y  L  A  W  Y  Q  Q  K  P
gggcagtctcctaaactgctgatttactgggcatccagtagggaatctggggtccctgat
 G  Q  S  P  K  L  L  I  Y  W  A  S  S  R  E  S  G  V  P  D
cgcttcacaggcagtggatctgggacagatttcactctcaccatcagcagtgtgaaggct
 R  F  T  G  S  G  S  G  T  D  F  T  L  T  I  S  S  V  K  A
gaagacctggcagtttattactgtcagcaatattataactatccgctcacgttcggtgct
 E  D  L  A  V  Y  Y  C  Q  Q  Y  Y  N  Y  P  L  T  F  G  A
gggaccaagttggagctgaaagctccggaggt*cccgaggcggcagcctggccgcgctg*
 G  T  K  L  E  L  K A  S  G  G  *P  E  G  G  S  L  A  A  L*
*accgcgcaccaggcttgccacctgccgctggagactttcacccgtcatcgccagccgcgc*
 *T  A  H  Q  A  C  H  L  P  L  E  T  F  T  R  H  R  Q  P  R*
*ggctgggaacaactggagcagtgcggctatccggtgcagcggctggtcgccctctacctg*
 *G  W  E  Q  L  E  Q  C  G  Y  P  V  Q  R  L  V  A  L  Y  L*
*gcggcgcggctgtcgtggaaccaggtcgaccaggtgatccgcaacgccctggccagcccc*
 *A  A  R  L  S  W  N  Q  V  D  Q  V  I  R  N  A  L  A  S  P*
*ggcagcggcggcgacctgggcgaagcgatccgcgagcagccggagcaagcccgtctggcc*
 *G  S  G  G  D  L  G  E  A  I  R  E  Q  P  E  Q  A  R  L  A*
*ctgaccctggccgcgccgagagcgagcgcttcgtccggcagggcaccggcaacgacgag*
 *L  T  L  A  A  A  E  S  E  R  F  V  R  Q  G  T  G  N  D  E*
*gccggcgcggccaacggcccggcggacagcggcgacgccctgctggagcgcaactatccc*
 *A  G  A  A  N  G  P  A  D  S  G  D  A  L  L  E  R  N  Y  P*
*actggcgcggagttcctcggcgacggcggcgacgtcagcttcagcacccgcggcacgcag*
 *T  G  A  E  F  L  G  D  G  G  D  V  S  F  S  T  R  G  T  Q*
*aactggacggtggagcggctgctccaggcgcaccgccaactgaaggagcgcggctatgtg*
 *N  W  T  V  E  R  L  L  Q  A  H  R  Q  L  E  E  R  G  Y  V*
*ttcgtcggctaccacggcaccttcctgaagcggcgcaaagcatcgtcttcggcgggtg*
 *F  V  G  Y  H  G  T  F  L  E  A  A  Q  S  I  V  F  G  G  V*
*cgcgcgcgcagccaggaccctgacgcggatctggcgcggtttctatatcgccggcgatccg*
 *R  A  R  S  Q  D  L  D  A  I  W  R  G  F  Y  I  A  G  D  P*
*gcgctggcctacggctacgcccaggaccaggaacccgacgcacgcggccggatccgcaac*
 *A  L  A  Y  G  Y  A  Q  D  Q  E  P  D  A  R  G  R  I  R  N*
*ggtgccctgctgcgggtctatgtgccgcgctcgagcctgccggcttctaccgcaccagc*
 *G  A  L  L  R  V  Y  V  P  R  S  S  L  P  G  F  Y  R  T  S*
*ctgaccctggccgcgccgaggcggcggcgaggtcgaacggctgatcggccatccgctg*
 *L  T  L  A  A  P  E  A  A  G  E  V  E  R  L  I  G  H  P  L*
*ccgctgcgcctggacgccatcaccggccccgaggaggaaggcgggcgcctggagaccatt*
 *P  L  R  L  D  A  I  T  G  P  E  E  G  G  R  L  E  T  I*
*ctcggctggccgctggccgagcgcaccgtggtgattccctcggcgatccccaccgacccg*
 *L  G  W  P  L  A  E  R  T  V  V  I  P  S  A  I  P  T  D  P*
*cgcaacgtcggcggcgacctcgacccgtccagcatccccgacaaggaacaggcgatcagc*
 *R  N  V  G  G  D  L  D  P  S  S  I  P  D  K  E  Q  A  I  S*
*gccctgccggactacgccagccagcccggcaaaccgccgcgcgaggacctgaagtaactg*
 *A  L  P  D  Y  A  S  Q  P  G  K  P  P  R  E  D  L  K  -*
```

```
atggaggtgcaccttgttggaagtggtggagcattggtgcagcctgaacggtcattgaaa
 M  E  V  Q  L  V  G  S  G  G  G  L  V  Q  P  E  G  S  L  K
ctctcatgtgcagcctctggattcaccttcaagaccaatgccatgaactgggtccgccag
 L  S  C  A  A  S  G  F  T  F  K  T  N  A  M  N  W  V  R  Q
gctccaggaaacggtttggaatgggttgctcgcataagaaataaaactaataattatgca
 A  P  G  K  G  L  E  W  V  A  R  I  R  N  K  T  N  N  Y  A
acatattatgccgactcagtgaaagacaggttcaccatctccagagatgattcacaaagc
 T  Y  Y  A  D  S  V  K  D  R  F  T  I  S  R  D  D  S  Q  S
atgctctatctgcaaatgaacaacttgaaaactgaagacacagccatgtatttctgtgtg
 M  L  Y  L  Q  M  N  N  L  K  T  E  D  T  A  M  Y  F  C  V
gccggtaactcgtttgcttactgggccaggtgactctggtcactgtctctgcaggcgga
 A  G  N  S  F  A  Y  W  G  Q  G  T  L  V  T  V  S  A  G  G
ggcggatcaggtggtggcggatccggaggtggcggaagcgacattgtgatgtcacagtct
 G  G  S  G  G  G  S  G  G  G  S  D  I  V  M  S  Q  S
ccatcctccctagctgtgtcagttggagagaaggttactgtgaactgcaagtccagtcag
 P  S  S  L  A  V  S  V  G  E  K  V  T  V  N  C  K  S  S  Q
agccttttatatagtaacaatcaaaagaactacttggcctggtaccagcagaaaccaggg
 S  L  L  Y  S  N  N  Q  K  N  Y  L  A  W  Y  Q  Q  K  P  G
cagtctcctaaactgctgatttactgggcatcaactagggaatatggggtccctgatcgc
 Q  S  P  K  L  L  I  Y  W  A  S  T  R  E  Y  G  V  P  D  R
ttcacaggcagtggatctgggacagatttcactctcaccatcagcagtgtgaaggctgaa
 F  T  G  S  G  S  G  T  D  F  T  L  T  I  S  S  V  K  A  E
gacctggcagtttattactgtcagcaatattataactatccgctcacgttcggtgctggg
 D  L  A  V  Y  Y  C  Q  Q  Y  Y  N  Y  P  L  T  F  G  A  G
accaagctggagctgaaagcttccggaggt*cccgagggcggcagcctggccgcgctgacc*
 T  K  L  E  L  K  A  S  G  G  *P  E  G  G  S  L  A  A  L  T*
*gcgcaccaggcttgccacctgccgctggagacttttcacccgtcatcgccagccgcgcgc*
 *A  H  Q  A  C  H  L  P  L  E  T  F  T  R  H  R  Q  P  R  G*
*tgggaacaactggagcagtgcggctatccggtgcagcggctggtcgccctctacctggcg*
 *W  E  Q  L  E  Q  C  G  Y  P  V  Q  R  L  V  A  L  Y  L  A*
*gcgcggctgtcgtggaaccaggtcgaccaggtgatccgcaacgccctggccagccccggc*
 *A  R  L  S  W  N  Q  V  D  Q  V  I  R  N  A  L  A  S  P  G*
*agcggcggcgacctgggcgaagcgatccgcgagcagccggagcaggcccgtctggccctg*
 *S  G  G  D  L  G  E  A  I  R  E  Q  P  E  Q  A  R  L  A  L*
*accctggccgccgcgagagcgagcgcttcgtccggcagggcaccggcaacgacgaggcc*
 *T  L  A  A  A  E  S  E  R  F  V  R  Q  G  T  G  N  D  E  A*
*ggcgcggccaacggcccggcggacagcggcgacgccctgctggagcgcaactatcccact*
 *G  A  A  N  G  P  A  D  S  G  D  A  L  L  E  R  N  Y  P  T*
*ggcgcggagttcctcggcgacggcgcgacgtcagcttcagcacccgcggcacgcagaac*
 *G  A  E  F  L  G  D  G  D  V  S  F  S  T  R  G  T  Q  N*
*tggacggtggagcggctgctccagcgccaccgccaactggaggagcgcggctatgtgttc*
 *W  T  V  E  R  L  L  Q  A  H  R  Q  L  E  E  R  G  Y  V  F*
*gtcggctaccacggcaccttcctcgaagcggcgcaaagcatcgtcttcggcggggtgcgc*
 *V  G  Y  H  G  T  F  L  E  A  A  Q  S  I  V  F  G  G  V  R*
*gcgcgcagccaggacctcgacgcgatctggcgcggtttctatatcgccggcgatccggcg*
 *A  R  S  Q  D  L  D  A  I  W  R  G  F  Y  I  A  G  D  P  A*
*ctggcctacggctacgcccaggaccaggaacccgacgcacgcggccggatccgcaacggt*
 *L  A  Y  G  Y  A  Q  D  Q  E  P  D  A  R  G  R  I  R  N  G*
*gccctgctgcgggtctatgtgccgcgctcgagcctgccgggcttctaccgcaccagcctg*
 *A  L  L  R  V  Y  V  P  R  S  S  L  P  G  F  Y  R  T  S  L*
*accctggccgccgccggaggcggcgggcgaggtgaacggctgatcggccatccgctgccg*
 *T  L  A  A  P  E  A  A  G  E  V  E  R  L  I  G  H  P  L  P*
*ctgcgcctggacgccatcaccggccccgaggaggaaggcggcgcctggagaccattctc*
 *L  R  L  D  A  I  T  G  P  E  E  E  G  G  R  L  E  T  I  L*
*ggctggccgctggccgagcgcaccgtggtgattccctcggcgatccccaccgacccgcgc*
 *G  W  P  L  A  E  R  T  V  V  I  P  S  A  I  P  T  D  P  R*
*aacgtcggcggcgacctcgacccgtccagcatccccgacaaggaacaggcgatcagcgcc*
 *N  V  G  G  D  L  D  P  S  S  I  P  D  K  E  Q  A  I  S  A*
*ctgccggactacgccagccagcccggcaaaccgccgcgcgaggacctgaagtaa*ctgccg
 *L  P  D  Y  A  S  Q  P  G  K  P  P  R  E  D  L  K*  -
```

```
atggaggtgcagcttcttgagactgctggagcattgctgcaccctaaagggtcattgaaa
 M  E  V  Q  L  V  E  T  G  G  G  L  V  Q  P  K  G  S  L  K
ctctcatgtgcagcctctggattcaccttcaataccaatgccatgaactggctccgccag
 L  S  C  A  A  S  G  F  T  F  N  T  N  A  M  N  W  V  R  Q
gctccaggaaagggtttgcaatgggttgctccgtaagaaataaaactaataattatcca
 A  P  G  K  G  L  C  W  V  A  R  V  R  N  K  T  N  N  Y  A
acatattatgccgattccgtgaaagacaggtttcaccatctccagagatgattcacaaagc
 T  Y  Y  A  D  S  V  K  D  R  F  T  I  S  R  D  D  S  Q  S
atgctctatctgcaaatgaacaacttgaaaactgaacacaccgccatttattactgtctg
 M  L  Y  L  Q  M  N  N  L  K  T  E  D  T  A  I  Y  Y  C  V
ggggctaactcgtttccttactgggccaagcgactctggtcactgtctctccaggcgga
 G  G  N  S  F  A  Y  W  G  Q  G  T  L  V  T  V  S  A  G  G
ggcggatcaggtggtcgcggatctgcaggtggcggaagcgacattgtgatgtcccagtct
 G  G  S  G  G  G  S  G  G  G  S  D  I  V  M  S  Q  S
ccatcctccctagctgtgtcagttggagagaaggttactatgagctgcaagtccagtcag
 P  S  S  L  A  V  S  V  G  E  K  V  T  M  S  C  K  S  S  Q
agcctttatatagtaacaatcaaaagaactacttggcctggtaccaccagaaaccaggg
 S  L  L  Y  S  N  N  Q  K  N  Y  L  A  W  Y  H  Q  K  P  G
cagtctcctaaactgctgatttactgggcatccactagggaatctggggtccctgatcgc
 Q  S  P  K  L  L  I  Y  W  A  S  T  R  E  S  G  V  P  D  R
ttcacaggcagtggatctgggacagatttcactctcaccatcagcagtgtgaaggctgaa
 F  T  G  S  G  S  G  T  D  F  T  L  T  I  S  S  V  K  A  E
gacctggcagtttattactgtcagcaatattatagctatccactcacgttcggtgctggg
 D  L  A  V  Y  Y  C  Q  Q  Y  Y  S  Y  P  L  T  F  G  A  G
accaagctggagctgaaagctccggcaggtcccgagggcggcagcctggccgcgctgacc
 T  K  L  E  L  K  A  S  G  G  P  E  G  G  S  L  A  A  L  T
gcgcaccaggcttgccacctgccgctggagactttcacccgtcatcgccagccgcgcggc
 A  H  Q  A  C  H  L  P  L  E  T  F  T  R  H  R  Q  P  R  G
tgggaacaactggagcagtgcggctatccggtgcagcggctggtcgccctctacctggcg
 W  E  Q  L  E  Q  C  G  Y  P  V  Q  R  L  V  A  L  Y  L  A
gcgcgcctgtcgtggaaccaggtcgaccaggtgatccgcaacgccctggccagcccccgg
 A  R  L  S  W  N  Q  V  D  Q  V  I  R  N  A  L  A  S  P  G
agcggcggcgacctgggcgaagcgatccgcgagcagccggagcaggcccgtctggccctg
 S  G  G  D  L  G  E  A  I  R  E  Q  P  E  Q  A  R  L  A  L
acccTagccgccgccgagagcgagcgcttcgtccggcagggcaccggcaacgacgaggcc
 T  L  A  A  A  E  S  E  R  F  V  R  Q  G  T  G  N  D  E  A
ggcgcgccaacgcccggcggacagcggcgacgccctgctggagcgcaactatcccact
 G  A  A  N  G  P  A  D  S  G  D  A  L  L  E  R  N  Y  P  T
ggcgcggagttcctcggcgacggcggcgacgtcagcttcagcacccgcggcacgcagaac
 G  A  E  F  L  G  D  G  G  D  V  S  F  S  T  R  G  T  Q  N
tggacggtggagcggctgctccaggcgcaccgccaactggaggagcgcggctatgtgttc
 W  T  V  E  R  L  L  Q  A  H  R  Q  L  E  E  R  G  Y  V  F
gtcggctaccacggcaccttcctcgaagcggcgcaaagcatcgtcttcggcggggtgcgc
 V  G  Y  H  G  T  F  L  E  A  A  Q  S  I  V  F  G  G  V  R
gcgcgcagcaggacctcgacgcgatctggcgcggttTctatatcgccggcgatccggcg
 A  R  S  Q  D  L  D  A  I  W  R  G  F  Y  I  A  G  D  P  A
ctggcctacggctacgcccaggaccaggaacccgacgcacgcggccggatccgcaacggt
 L  A  Y  G  Y  A  Q  D  Q  E  P  D  A  R  G  R  I  R  N  G
gccctgctgcgggtctatgtgccgcgctcgagcctgccgggcttctaccgcaccagcctg
 A  L  L  R  V  Y  V  P  R  S  S  L  P  G  F  Y  R  T  S  L
acccTggccgcgccggaggcggcggcgaggTcgaacgctgatcggccatccgctgccg
 T  L  A  A  P  E  A  A  G  E  V  E  R  L  I  G  H  P  L  P
ctgcgcctggacgccatcaccggccccgaggaggaaggcgggcgcctggagaccattctc
 L  R  L  D  A  I  T  G  P  E  E  E  G  G  R  L  E  T  I  L
ggctggccgctggccgagcgcaccgtggtgattccctcggcgatccccaccgacccgcgc
 G  W  P  L  A  E  R  T  V  V  I  P  S  A  I  P  T  D  P  R
aacgtcggcggcgacctcgacccgtccagcatccccgacaaggaacaggcgatcagcgcc
 N  V  G  G  D  L  D  P  S  S  I  P  D  K  E  Q  A  I  S  A
ctgccggactacgccagccagcccggcaaaccgccgcgcgaggacctgaagtaactgccg
 L  P  D  Y  A  S  Q  P  G  K  P  P  R  E  D  L  K  -
```

```
atggaggtgcagcttgttgagactggcggaggattcgtgcagcctgaagggtcattg
 M  E  V  Q  L  V  E  T  G  G  G  L  V  Q  P  E  G  S  L
aaactctcatgtgcaacgtctggattcaacttcaataccaatgccatgaactgcgtccgc
 K  L  S  C  A  T  S  G  F  N  F  N  T  N  A  M  N  W  V  R
caggctccaggaaaggggtttggaatgggttgctcgcgtaagaaataaaactaataattat
 Q  A  P  G  K  G  L  E  W  V  A  R  V  R  N  K  T  N  N  Y
gcaacatattatgccgattcagtgaaagacaggttcaccatctccagagatgattcacaa
 A  T  Y  Y  A  D  S  V  K  D  R  F  T  I  S  R  D  D  S  Q
acaatggtctttctgcaaatgaataacttgaaaactgaggacacagccatctattactgt
 R  M  V  F  L  Q  M  N  N  L  K  T  E  D  T  A  I  Y  Y  C
gtggcggggaactcgtttgcttattgggggccaaggcactctggtcactgtctctcctggc
 V  A  G  N  S  F  A  Y  W  G  Q  G  T  L  V  T  V  S  P  G
gcaggcggatcaggtggtggcggatctggaggtggcggaagcgacattgtgatgtcacag
 G  G  G  S  G  G  G  G  S  G  G  G  G  S  D  I  V  M  S  Q
tctccatcctccctagctgtgtcagttggagagagggttactatgaactgcaagtccagt
 S  P  S  S  L  A  V  S  V  G  E  R  V  T  M  N  C  K  S  S
cagagtcttttatatagtagcaatcaaaagaactacttggcctggtaccagcagaaacca
 Q  S  L  L  Y  S  S  N  Q  K  N  Y  L  A  W  Y  Q  Q  K  P
gggcagtctcctaaactgctgatttactgggcatccactagggaatctgggtccctgat
 G  Q  S  P  K  L  L  I  Y  W  A  S  T  R  E  S  G  V  P  D
cgcttcacaggcagtgtatctgggacagatttcactctcaccatcagcagtgtgaaggct
 R  F  T  G  S  V  S  G  T  D  F  T  L  T  I  S  S  V  K  A
gaagacctggcagtttattactgtcagcaatattataactatccgctcacgttcggtgct
 E  D  L  A  V  Y  Y  C  Q  Q  Y  Y  N  Y  P  L  T  F  G  A
gggaccaagctggagctgaaagcttccggagggcccgaggcggcagcctggccgcgctg
 G  T  K  L  E  L  K  A  S  G  G  P  E  G  G  S  L  A  A  L
accgcgcaccaggcttgccacctgccgctggagactttcacccgtcatcgccagccgcgc
 T  A  H  Q  A  C  H  L  P  L  E  T  F  T  R  H  R  Q  P  R
ggctgggaacaactggagcagtgcggctatccggtgcagcggctggtcgccctctacctg
 G  W  E  Q  L  E  Q  C  G  Y  P  V  Q  R  L  V  A  L  Y  L
gcggcgcggctgtcgtggaaccaggtcgaccaggtgatccgcaacgccctggccagcccc
 A  A  R  L  S  W  N  Q  V  D  Q  V  I  R  N  A  L  A  S  P
ggcagcggcggcgacctgggcgaagcgatccgcgagcagccggagcaggcccgtctggcc
 G  S  G  G  D  L  G  E  A  I  R  E  Q  P  E  Q  A  R  L  A
ctgaccctggccgccgccgagagcgagcgcttcgtccggcagggcaccggcaacgacgag
 L  T  L  A  A  A  E  S  E  R  F  V  R  Q  G  T  G  N  D  E
gccggcgcggccaacggcccggcggacagcggcgacgccctgctggagcgcaactatccc
 A  G  A  A  N  G  P  A  D  S  G  D  A  L  L  E  R  N  Y  P
actggcgcggagttcctcggcgacggcggcgacgtcagcttcagcacccgcggcacgcag
 T  G  A  E  F  L  G  D  G  G  D  V  S  F  S  T  R  G  T  Q
aactggacggtggagcggctgctccaggcgcaccgccaactggaggagcgcggctatgtg
 N  W  T  V  E  R  L  L  Q  A  H  R  Q  L  E  E  R  G  Y  V
ttcgtcggctaccacggcaccttcctcgaagcggcgcaaagcatcgtcttcggcggggtg
 F  V  G  Y  H  G  T  F  L  E  A  A  Q  S  I  V  F  G  G  V
cgcgcgcgcagccaggacctcgacgcgatctggcgcggttttctatatcgccggcgatccg
 R  A  R  S  Q  D  L  D  A  I  W  R  G  F  Y  I  A  G  D  P
gcgctggcctacggctacgcccaggaccaggaacccgacgcacgcggccggatccgcaac
 A  L  A  Y  G  Y  A  Q  D  Q  E  P  D  A  R  G  R  I  R  N
ggtgccctgctgcgggtctatgtgccgcgctcgagcctgccgggcttctaccgcaccagc
 G  A  L  L  R  V  Y  V  P  R  S  S  L  P  G  F  Y  R  T  S
ctgaccctggccgcgccggaggcggcgggcgaggtcgaacggctgatcggccatccgctg
 L  T  L  A  A  P  E  A  A  G  E  V  E  R  L  I  G  H  P  L
ccgctgcgcctggacgccataccggcccgaggaggaaggcgggcgcctggagaccatt
 P  L  R  L  D  A  I  T  G  P  E  E  E  G  G  R  L  E  T  I
ctcggctggccgctggcgagcgcaccgtggtgattccctcggcgatccccaccgacccg
 L  G  W  P  L  A  E  R  T  V  V  I  P  S  A  I  P  T  D  P
cgcaacgtcggcggcgacctcgacccgtccagcatccccgacaaggaacaggcgatcagc
 R  N  V  G  G  D  L  D  P  S  S  I  P  D  K  E  Q  A  I  S
gccctgccggactacgccagccagcccggcaaaccgccgcgcgaggacctgaagtaactg
 A  L  P  D  Y  A  S  Q  P  G  K  P  P  R  E  D  L  K  -
```

VH
VL
*PE38*

HIGH-AFFINITY MONOCLONAL ANTIBODIES TO GLYPICAN-3 AND USE THEREOF

CROSS REFERENCE TO RELATED APPLICATIONS

This is the U.S. National Stage of International Application No. PCT/US2013/043633, filed May 31, 2013, published in English under PCT Article 21(2), which claims the benefit of U.S. Provisional Application No. 61/654,232, filed Jun. 1, 2012, which is herein incorporated by reference in its entirety.

FIELD

This disclosure concerns high-affinity antibodies specific for glypican-3 (GPC3), and their use for the diagnosis and treatment of cancer.

BACKGROUND

Liver cancer is the fifth most common malignant tumor worldwide (Ho, *BioDrugs* 25:275-284, 2011), with hepatocellular carcinoma (HCC) being the most common form. Cholangiocarcinoma (CCA) is another major form of primary liver cancer. Although surgical resection offers a standard method for treatment of the disease, only a small portion of patients are eligible for the procedure. Liver cancer does not respond to most chemotherapy drugs. Thus, there is a critical need for novel immunotherapy, such as antibody therapy. It has been suggested that glypican-3 (GPC3) represents an attractive target for liver cancer therapy given that it is highly expressed in HCC (Capurro et al., *Gastroenterology* 125:89-97, 2003; Capurro and Filmus, *Cancer Res* 65:372, 2005; Ho and Kim, *Eur J Cancer* 47:333-338, 2011; Allegretta and Filmus, *Anticancer Agents Med Chem* 11:543-548, 2011).

The GPC3 gene encodes a 70-kDa precursor core protein, which can be cleaved by furin to generate a 40-kDa amino (N) terminal protein and a 30-kDa membrane-bound carboxyl (C) terminal protein. The C-terminus is attached to the cell membrane by a glycosylphosphatidylinositol (GPI) anchor. GPC3 has been suggested as a target for both antibody (Ishiguro et al., *Cancer Res* 68:9832-9838, 2008; Nakano et al., *Biochem Biophys Res Commun* 378:279-284, 2009; Nakano et al., *Anticancer Drugs* 21:907-916, 2010) and cell-based (Nakatsura et al., *Clin Cancer Res* 10:8630-8640, 2004; Komori et al., *Clin Cancer Res* 12:2689-2697, 2006) immunotherapies. However, GPC3 expression is highly heterogeneous in HCC and other cancers (e.g., ovarian clear cell carcinoma and melanoma) (Suzuki et al., *Cancer Sci*, 102:1622-1629, 2011). Ideal therapeutic monoclonal antibodies (mAbs) should eliminate tumor cells expressing low levels of target antigen. Research in the area has been hampered by the lack of high-affinity mAbs that could be used to detect low expression of GPC3 in tumor cells for cancer therapy and diagnostics.

Filmus and colleagues developed the widely-used 1G12 mAb specific for the C-terminus of GPC3 and established an ELISA method to detect serum GPC3 in HCC patients (Capurro et al., *Gastroenterology* 125:89-97, 2003). Hippo et al. developed mAbs specific for the N-terminus of GPC3 (Hippo et al., *Cancer Res*, 64:2418-2423, 2004). While both studies detected soluble GPC3 protein in HCC culture supernatant or in the circulating blood of cancer patients, it is not clear whether the N-terminal or C-terminal subunit actually represents the soluble GPC3 format (Capurro and Filmus, *Cancer Res* 65:372, 2005). Prior studies indicate that concentrations of serum GPC3 are generally not high in patients and that none of the readily available mAbs can be used to measure serum GPC3, most likely due to low affinity of the mAb for GPC3.

SUMMARY

Disclosed herein is a panel of monoclonal antibodies that bind with high affinity to cell surface and soluble GPC3 proteins. The antibodies provided herein include immunoglobulin molecules, such as IgG antibodies, as well as antibody fragments and humanized monoclonal antibodies and fragments. Further provided are compositions including the antibodies that bind, for example specifically bind, to GPC3, nucleic acid molecules encoding these antibodies, expression vectors comprising the nucleic acid molecules, and isolated host cells that express the nucleic acid molecules. Also provided are immunoconjugates comprising the antibodies disclosed herein and an effector molecule, such as a toxin.

The antibodies and compositions provided herein can be used for a variety of purposes, such as for confirming the diagnosis of a cancer that expresses GPC3, for example HCC, melanoma, squamous cell carcinoma of the lung or ovarian clear cell carcinoma. Thus, provided herein is a method of confirming the diagnosis of cancer in a subject by contacting a sample from the subject diagnosed with cancer with a monoclonal antibody that binds GPC3, and detecting binding of the antibody to the sample. An increase in binding of the antibody to the sample relative to binding of the antibody to a control sample confirms the cancer diagnosis. In some embodiments, the method further includes contacting a second antibody that specifically recognizes the GPC3-specific antibody with the sample, and detecting binding of the second antibody.

Similarly, provided herein is a method of detecting a cancer that expresses GPC3 in a subject. The method includes contacting a sample from the subject with a monoclonal antibody described herein, and detecting binding of the antibody to the sample. An increase in binding of the antibody to the sample relative to a control sample detects cancer in the subject. In some embodiments, the methods further comprise contacting a second antibody that specifically recognizes the GPC3-specific antibody with the sample, and detecting binding of the second antibody.

Further provided is a method of treating a subject with cancer, for example HCC, melanoma, squamous cell carcinoma of the lung or ovarian clear cell carcinoma, by selecting a subject with a cancer that expresses GPC3 and administering to the subject a therapeutically effective amount of a monoclonal antibody specific for GPC3, or an immunoconjugate comprising the antibody.

Also provided is a method for inhibiting tumor growth in a subject by selecting a subject with a cancer that expresses GPC3 and administering to the subject a therapeutically effective amount of an antibody, immunoconjugate or composition disclosed herein.

The foregoing and other objects, features, and advantages of the invention will become more apparent from the following detailed description, which proceeds with reference to the accompanying figures.

BRIEF DESCRIPTION OF THE DRAWINGS

FIGS. 1A-1E: Discovery of new monoclonal antibodies to GPC3. (FIG. 1A) Schematic structure of GPC3. The human GPC3 gene encodes a 70 kDa precursor protein of 580 amino acids. In the mature form at the cell membrane, a GPI anchor replaces the C-terminal signal (predicted cleavage site: S560). The core protein is held together by cysteine residues forming disulfide bridges. Heparan sulfate (HS) chains are attached to the polypeptide core. The immunization peptide corresponding to the C-terminal end of mature GPC3 is indicated. (FIG. 1B) High-throughput flow cytometry screening. Representative histograms obtained with positive (top panel) and negative supernatant (bottom panel). Each hybridoma was tested for GPC3-specific mAb production by a simultaneous binding assay incorporating a 1:1 mixture of antigen-positive A431/G1 cells and antigen-negative A431 cells in a flow cytometry analysis. (FIG. 1C) Flow cytometry analysis of five selected mouse hybridoma clones (YP6, YP7, YP8, YP9 and YP9.1) (solid lines) and 1G12, a control anti-GPC3 mAb (dotted lines, in the middle) using A431/G1 and Hep3B. Filled peak: isotype control. (FIG. 1D) ELISA analysis of five hybridoma clones on recombinant GPC3 proteins. GPC3: recombinant GPC3-human Fc; GPC3AHS: recombinant GPC3 without HS; control: BSA; 1G12: a commercial anti-GPC3 mAb. (FIG. 1E) Western blot analysis of YP7 and YP9. Thirty µg of whole cell lysates of HepG2, Hep3B, A431/G1 (A431.GPC3+) and A431 was loaded and probed with each hybridoma supernatant.

(FIG. 2A) Flow cytometry analysis using a panel of endogenous GPC3-expressing human cell lines. Binding of YP7 to four HCC cell lines (HepG2, Hep3B, Huh4 and Huh7), four CCA cell lines (HuCCT1, KMBC, KMCH and Mz-ChA-1), one ovarian CCC cell line (TOV-21G) and one melanoma cell line (UACC-62) is shown. (FIG. 2B) Binding affinity measurement of YP7 against cell surface-associated GPC3. MFI: mean fluorescence intensity. The Scatchard plot and the $K_D$ value were calculated using Prism. (FIG. 2C) Binding of YP7 on recombinant GPC1, GPC3 and GPC5 proteins.

FIGS. 3A-3E: GPC3 protein expression in liver cancer. (FIG. 3A) GPC3 expression in liver cancer cell lines detected in Western blotting. HCC: hepatocellular carcinoma; CCA: cholangiocarcinoma; 1G12: a commercial mAb to GPC3; Mz: Mz-ChA-1; SK: SK-Hep-1. (FIG. 3B) Western blots of ovarian clear cell carcinoma (CCC). TOV-21G: an ovarian CCC line. (FIG. 3C) Soluble GPC3 protein immunoprecipitated from culture supernatant and analyzed by Western blotting. YP7 was used to pull down soluble GPC3 protein in culture supernatant. H: mouse IgG heavy chain; L: mouse IgG light chain; C-terminus: C-terminal subunit (~30 kDa); IP: immunoprecipitation. (FIG. 3D) GPC3 expression analysis by Western blotting in nine HCC and nine CCA primary liver tumor tissues. (FIG. 3E) Immunohistochemistry of GPC3 in HCC tissues. Circles identify tumor nests (a, c) with or without distinct GPC3 positivity at a low magnification. Arrows identify tumor (b, d) with or without GPC3 positivity at a higher magnification. a, c: 100×; b and d: a higher magnification (400×) of a and c, respectively.

(FIG. 4A) BALB/c nu/nu mice s.c. inoculated with HepG2 cells. When tumors reached an average volume of 100 mm³, mice were administered 5 mg/kg of YP7 twice a week for two and a half weeks. Arrow: YP7 injection; * p<0.05. (FIG. 4B) Representative mice bearing HCC tumors in treated (YP7) and untreated (vehicle) groups.

FIG. 5 is a nucleotide alignment of the YP6 clone 4 (SEQ ID NO: 15), YP6 clone 7 (SEQ ID NO: 36), YP8 (SEQ ID NO: 15), YP7 (SEQ ID NO: 7), YP9 (SEQ ID NO: 19) and YP9.1 (SEQ ID NO: 11) VH sequences showing the locations of CDR1, CDR2 and CDR3 as determined using IMGT (bold) and Kabat (underline).

FIG. 6 is an amino acid alignment of the YP6 clone 4 (SEQ ID NO: 16), YP6 clone 7 (SEQ ID NO: 37), YP8 (SEQ ID NO: 16), YP7 (SEQ ID NO: 8), YP9 (SEQ ID NO: 20) and YP9.1 (SEQ ID NO: 12) VH sequences showing the locations of CDR1, CDR2 and CDR3 as determined using IMGT (bold) and Kabat (underline).

FIGS. 7A-7B show a nucleotide alignment of the YP6 (SEQ ID NO: 17), YP8 (SEQ ID NO: 17), YP9 clone 9 (SEQ ID NO: 21), YP9 clone 1 (SEQ ID NO: 25), YP9 clone 10 (SEQ ID NO: 23), YP9.1 (SEQ ID NO: 13) and YP7 (SEQ ID NO: 9), VL sequences showing the locations of CDR1, CDR2 and CDR3 as determined using IMGT (bold) and Kabat (underline).

FIG. 8 is an amino acid alignment of the YP6 (SEQ ID NO: 18), YP8 (SEQ ID NO: 18), YP9 clone 9 (SEQ ID NO: 22), YP9 clone 1 (SEQ ID NO: 26), YP9 clone 10 (SEQ ID NO: 24), YP9.1 (SEQ ID NO: 14) and YP7 (SEQ ID NO: 10) VL sequences showing the locations of CDR1, CDR2 and CDR3 as determined using IMGT (bold) and Kabat (underline).

FIGS. 9A-9D show the nucleotide and amino acid sequences of GPC3-specific immunotoxins. (FIG. 9A) Nucleotide (SEQ ID NO: 27) and amino acid (SEQ ID NO: 28) sequence of the YP7ScFv-PE38 immunotoxin. (FIG. 9B) Nucleotide (SEQ ID NO: 30) and amino acid (SEQ ID NO: 31) sequence of the YP8ScFv-PE38 immunotoxin. (FIG. 9C) Nucleotide (SEQ ID NO: 32) and amino acid (SEQ ID NO: 33) sequence of the YP9ScFv-PE38 immunotoxin. (FIG. 9D) Nucleotide (SEQ ID NO: 34) and amino acid (SEQ ID NO: 35) sequence of the YP9.1ScFv-PE38 immunotoxin. In FIGS. 9A-9D, VH sequence is underlined, VL sequence is shown in bold and the PE38 sequence is italicized and underlined.

SEQUENCE LISTING

Figure 1A:
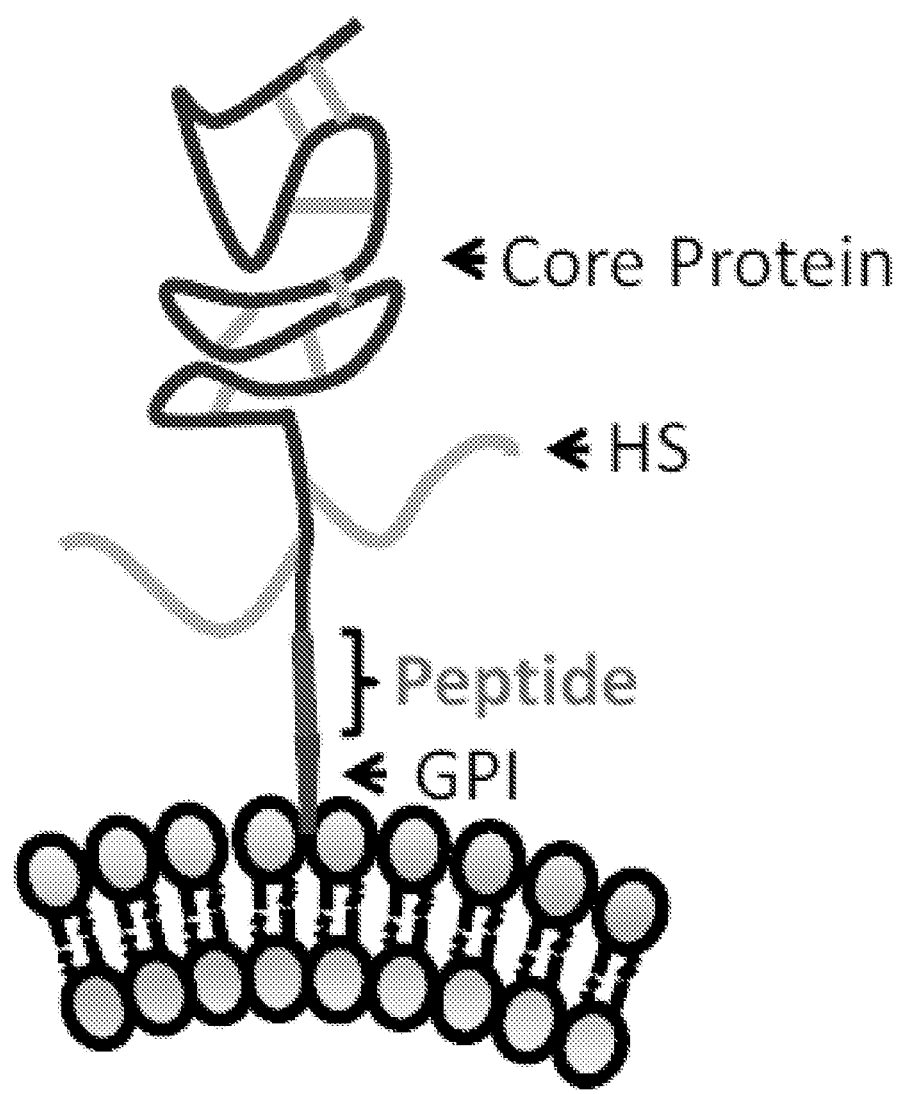

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Nov. 7, 2014, 68.6 KB, which is incorporated by reference herein. In the accompanying sequence listing:

SEQ ID NO: 1 is the amino acid sequence of PE38.
SEQ ID NO: 2 is the amino acid sequence of PE-LR.
SEQ ID NO: 3 is the amino acid sequence of PE-LR/6X.
SEQ ID NO: 4 is the amino acid sequence of PE with reduced immunogenicity.
SEQ ID NO: 5 is the amino acid sequence of PE-LR/8M.
SEQ ID NO: 6 is the amino acid sequence of a GPC3 peptide.
SEQ ID NO: 7 is the nucleotide sequence of the YP7 VH domain.

SEQ ID NO: 8 is the amino acid sequence of the YP7 VH domain.
SEQ ID NO: 9 is the nucleotide sequence of the YP7 VL domain.
SEQ ID NO: 10 is the amino acid sequence of the YP7 VL domain.
SEQ ID NO: 11 is the nucleotide sequence of the YP9.1 VH domain.
SEQ ID NO: 12 is the amino acid sequence of the YP9.1 VH domain.
SEQ ID NO: 13 is the nucleotide sequence of the YP9.1 VL domain.
SEQ ID NO: 14 is the amino acid sequence of the YP9.1 VL domain.
SEQ ID NO: 15 is the nucleotide sequence of the YP8 and YP6 clone 4 VH domain.
SEQ ID NO: 16 is the amino acid sequence of the YP8 and YP6 clone 4 VH domain.
SEQ ID NO: 17 is the nucleotide sequence of the YP8 and YP6 VL domain.
SEQ ID NO: 18 is the amino acid sequence of the YP8 and YP6 VL domain.
SEQ ID NO: 19 is the nucleotide sequence of the YP9 VH domain.
SEQ ID NO: 20 is the amino acid sequence of the YP9 VH domain.
SEQ ID NO: 21 is the nucleotide sequence of the YP9 clone 9 VL domain.
SEQ ID NO: 22 is the amino acid sequence of the YP9 clone 9 VL domain.
SEQ ID NO: 23 is the nucleotide sequence of the YP9 clone 10 VL domain.
SEQ ID NO: 24 is the amino acid sequence of the YP9 clone 10 VL domain.
SEQ ID NO: 25 is the nucleotide sequence of the YP9 clone 1 VL domain.
SEQ ID NO: 26 is the amino acid sequence of the YP9 clone 1 VL domain.
SEQ ID NO: 27 is the nucleotide sequence of the YP7ScFv-PE38 immunotoxin.
SEQ ID NO: 28 is the amino acid sequence of the YP7ScFv-PE38 immunotoxin.
SEQ ID NO: 29 is the amino acid sequence of *Pseudomonas* exotoxin (PE).
SEQ ID NO: 30 is the nucleotide sequence of the YP8ScFv-PE38 immunotoxin.
SEQ ID NO: 31 is the amino acid sequence of the YP8ScFv-PE38 immunotoxin.
SEQ ID NO: 32 is the nucleotide sequence of the YP9ScFv-PE38 immunotoxin.
SEQ ID NO: 33 is the amino acid sequence of the YP9ScFv-PE38 immunotoxin.
SEQ ID NO: 34 is the nucleotide sequence of the YP9.1ScFv-PE38 immunotoxin.
SEQ ID NO: 35 is the amino acid sequence of the YP9.1ScFv-PE38 immunotoxin.
SEQ ID NO: 36 is the nucleotide sequence of the YP6 clone 7 VH domain.
SEQ ID NO: 37 is the amino acid sequence of the YP6 clone 7 VH domain.
SEQ ID NO: 38 is a H-CDR1 consensus amino acid sequence (IMGT).
SEQ ID NO: 39 is a H-CDR2 consensus amino acid sequence (IMGT).
SEQ ID NO: 40 is a H-CDR3 consensus amino acid sequence (IMGT).
SEQ ID NO: 41 is a H-CDR1 consensus amino acid sequence (Kabat).
SEQ ID NO: 42 is a H-CDR2 consensus amino acid sequence (Kabat).
SEQ ID NO: 43 is a H-CDR3 consensus amino acid sequence (Kabat).
SEQ ID NO: 44 is a H-CDR1 consensus amino acid sequence (IMGT).
SEQ ID NO: 45 is a H-CDR3 consensus amino acid sequence (IMGT and Kabat).
SEQ ID NO: 46 is a H-CDR1 consensus amino acid sequence (Kabat).
SEQ ID NO: 47 is a H-CDR2 consensus amino acid sequence (Kabat).

DETAILED DESCRIPTION

I. Abbreviations

BSA bovine serum albumin
CAR chimeric antigen receptor
CCA cholangiocarcinoma
CCC clear cell carcinoma
CDR complementarity determining region
CTL cytotoxic T lymphocyte
ELISA enzyme-linked immunosorbent assay
FACS fluorescence activated cells sorting
GPC3 glypican 3
GPI glycosylphosphatidylinositol
HCC hepatocellular carcinoma
HS heparan sulfate
$IC_{50}$ inhibitory concentration 50
Ig immunoglobulin
IHC immunohistochemistry
IP immunoprecipitation
IT immunotoxin
KLH keyhole limpet hemocyanin
mAb monoclonal antibody
MFI mean fluorescence intensity
PE phycoerythrin
PE *Pseudomonas* exotoxin
s.c. subcutaneous
VH or $V_H$ variable heavy
VL or $V_L$ variable light II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A polypeptide ligand comprising at least a light chain or heavy chain immunoglobulin variable region which recognizes and binds (such as specifically recognizes and specifically binds) an epitope of an antigen, such as GPC3, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook,* 1994-1995 (Pierce Chemical Co., Rockford, Ill.); Kuby, J., *Immunology,* 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined according to Kabat et al. (see, Kabat et al., *Sequences of Proteins of Immunological Interest,* U.S. Department of Health and Human Services, 1991) and the ImMunoGeneTics database (IMGT) (see, Lefranc, *Nucleic Acids Res* 29:207-9, 2001; and online at imgt.cines.fr/IMGT_vquest/vquest?livret=0&Option=humanIg). The Kabat database is maintained online (world wide web at ncbi.nlm.nih.gov/igblast/). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or H-CDR3) is located in the variable domain of the heavy chain of the antibody in which it is found, whereas a $V_L$ CDR1 (or L-CDR1) is the CDR1 from the variable domain of the light chain of the antibody in which it is found. An antibody that binds GPC3, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds GPC3.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Binding affinity: Affinity of an antibody for an antigen. In one embodiment, affinity is calculated by a modification of the Scatchard method described by Frankel et al., *Mol. Immunol.,* 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In another embodiment, antibody affinity is measured by flow cytometry. An antibody that "specifically binds" an antigen (such as GPC3) is an antibody that binds the antigen with high affinity and does not significantly bind other unrelated antigens.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating liver cancer, such as HCC, or another tumor, such as ovarian cancer or melanoma. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., © 2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds GPC3 used in combination with a radioactive or chemical compound.

Conservative variant: "Conservative" amino acid substitutions are those substitutions that do not substantially affect or decrease the affinity of a protein, such as an antibody to GPC3. For example, a monoclonal antibody that specifically binds GPC3 can include at most about 1, at most about 2, at most about 5, and most about 10, or at most about 15 conservative substitutions and specifically bind the GPC3 polypeptide. The term "conservative variant" also includes the use of a substituted amino acid in place of an unsubstituted parent amino acid, provided that antibody specifically binds GPC3. Non-conservative substitutions are those that reduce an activity or binding to GPC3.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Complementarity determining region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a GPC3 polypeptide or an antibody that binds GPC3 that includes a sequence that is degenerate as a result of the genetic code. There are 20 natural amino acids, most of which are specified by more than one codon. Therefore, all degenerate nucleotide sequences are included as long as the amino acid sequence of the GPC3 polypeptide or antibody that binds GPC3 encoded by the nucleotide sequence is unchanged.

Diagnostic: Identifying the presence or nature of a pathologic condition, such as, but not limited to, liver cancer, ovarian cancer, melanoma or lung cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as liver cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-GPC3 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm Ther* 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In and $^{125}$I, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as GPC3.

Framework region: Amino acid sequences interposed between CDRs. Framework regions include variable light and variable heavy framework regions. The framework regions serve to hold the CDRs in an appropriate orientation for antigen binding.

Glypican-3 (GPC3): A member of the glypican family of heparan sulfate (HS) proteoglycans that are attached to the cell surface by a glycosylphosphatidylinositol anchor (Filmus and Selleck, *J Clin Invest* 108:497-501, 2001). The GPC3 gene codes for a core protein of approximately 70 kD, which can be cleaved by furin to produce an N-terminal 40 kD fragment and a C-terminal 30 kD fragment. Two HS chains are attached on the C-terminal portion of GPC3. GPC3 and other glypican family proteins play a role in cell division and cell growth regulation. GPC3 is highly expressed in HCC and some other human cancers including melanoma, squamous cell carcinomas of the lung, and clear cell carcinomas of the ovary (Ho and Kim, *Eur J Cancer* 47(3):333-338, 2011), but is not expressed in normal tissues. GPC3 is also known as SGB, DGSX, MXR7, SDYS, SGBS, OCI-5, SGBS1 and GTR2-2.

There are four known isoforms of human GPC3 (isoforms 1-4). Nucleic acid and amino acid sequences of the four isoforms of GPC3 are known, including GenBank Accession numbers: NM_001164617 and NP_001158089 (isoform 1); NM_004484 and NP_004475 (isoform 2); NM_001164618 and NP_001158090 (isoform 3); and NM_001164619 and NP_001158091 (isoform 4). In some embodiments of the present disclosure, the antibodies disclosed herein bind one or more of the four human GPC3 isoforms, or a conservative variant thereof.

HAMA (human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Hepatocellular carcinoma (HCC): A primary malignancy of the liver typically occurring in patients with inflammatory livers resulting from viral hepatitis, liver toxins or hepatic cirrhosis (often caused by alcoholism). HCC is also called malignant hepatoma.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody or functional fragment thereof. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Melanoma: A form of cancer that originates in melanocytes (cells that make the pigment melanin). Melanocytes are found primary in the skin, but are also present in the bowel and eye. Melanoma in the skin includes superficial spreading melanoma, nodular melanoma, acral lentiginous melanoma, and lentigo maligna (melanoma). Any of the above types may produce melanin or can be amelanotic. Similarly, any subtype may show desmoplasia (dense fibrous reaction with neurotropism) which is a marker of aggressive behavior and a tendency to local recurrence. Other melanomas include clear cell sarcoma, mucosal melanoma and uveal melanoma.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synoviomia, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In several examples, a tumor is a liver cancer, such HCC or hepatoblastoma, melanoma, a squamous cell carcinoma, such as squamous cell carcinoma of the lung, a clear cell carcinoma, such as clear cell carcinoma of the ovary, thyroid cancer, Wilms' tumor, neuroblastoma, or a testicular germ cell tumor.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Ovarian clear cell carcinoma: A distinct histopathologic subtype of epithelial ovarian cancer with an incidence of less than 5% of all ovarian malignancies. When viewed under a microscope, the insides of the cells of this type of tumor appear clear.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which GPC3 is expressed.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy, such as an HCC tissue biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a GPC3 polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Squamous cell carcinoma: A type of cancer that originates in squamous cells, thin, flat cells that form the surface of the skin, eyes, various internal organs, and the lining of hollow organs and ducts of some glands. Squamous cell carcinoma is also referred to as epidermoid carcinoma. One type of squamous cell carcinoma is squamous cell carcinoma of the lung.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Hepatocellular carcinoma (HCC) and cholangiocarcinoma (CCA) are two major forms of primary liver cancers. Glypican-3 (GPC3) is a new target in HCC and other cancers. However, tumor cells are heterogeneous in their expression of GPC3. GPC3-targeted cancer therapy has been hampered by the lack of high-affinity monoclonal antibodies (mAbs) that may be used to target cells exhibiting low GPC3 expression levels.

Disclosed herein is a high-throughput flow cytometry screening method that efficiently isolated a panel of GPC3-specific mAbs (YP6, YP7, YP8, YP9 and YP9.1) for cell surface binding. The antibodies were used to characterize GPC3 protein expression in human liver cancer (HCC and CCA) cell lines and tissues by flow cytometry, immunoblotting and immunohistochemistry. The highest affinity antibody (YP7) was used to evaluate GPC3 expression in non-HCC cell lines, and assessed for anti-tumor cytotoxic activity against tumor xenografts in mice.

The mAbs disclosed herein bind with high affinity to the native form of GPC3 on cancer cells, as well as soluble GPC3. YP7 bound cell surface-associated GPC3 with equilibrium dissociation constant, $K_D$=0.3 nmol/L and was highly specific for HCC, but not CCA or normal tissues. The YP7 antibody was highly sensitive in that it detected GPC3 in low expression cancer cells and exhibited significant HCC tumor growth inhibition in mice. Immunotoxins comprising the antibodies disclosed herein (YP7, YP8, YP9 clone 9 or YP9.1) fused to PE38 exhibited very high binding affinity for GPC3-expressing cells and significantly inhibited GPC3-expressing cancer cell growth. Thus, the high-affinity mAbs disclosed herein can be used for GPC3-expressing cancer diagnostics and therapy.

IV. High Affinity Monoclonal Antibodies that Bind GPC3

Disclosed herein is a panel of monoclonal antibodies that bind with high affinity to cell surface and soluble GPC3 proteins. The nucleotide and amino acid sequences of the VH and VL domains of the YP7, YP8, YP9 and YP9.1 antibodies are shown below. Tables 1-4 list the nucleotide and amino acid positions of the CDRs for each antibody, as determined by Kabat and IMGT. FIGS. 5-8 show nucleotide and amino acid alignments of the VH and VL domains of the antibodies.

YP7 VH Nucleotide Sequence
(SEQ ID NO: 7)
GAGGTGCAGCTTGTTGAGACTGGTGGAGGAATGGTGCAGCCTGAAGGGTC

ATTGAAACTCTCATGTGCAGCCTCTGGATTCACCTTCAATAAGAATGCCA

TGAATTGGGTCCGCCAGGCTCCAGGAAAGGGTTTGGAATGGGTTGCTCGC

ATAAGAAATAAAACTAATAATTATGCAACATATTATGCCGATTCAGTGAA

AGCCAGGTTTACCATCTCCAGAGATGATTCACAAAGCATGCTCTATCTGC

AAATGAACAACTTGAAAATTGAGGACACAGCCATGTACTATTGTGTGGCT

GGTAACTCGTTTGCTTACTGGGGCCAAGGGACTCTGGTCACTGTCTCTGC

A

YP7 VH Amino Acid Sequence
(SEQ ID NO: 8)
EVQLVETGGGMVQPEGSLKLSCAASGFTFNKNAMNWVRQAPGKGLEWVAR

IRNKTNNYATYYADSVKARFTISRDDSQSMLYLQMNNLKIEDTAMYYCVA

GNSFAYWGQGTLVTVSA

YP7 VL Nucleotide Sequence
(SEQ ID NO: 9)
GACATTGTGATGTCACAGTCTCCATCCTCCCTAGTTGTGTCAATTGGAGA

GAAGGTTACTATGACCTGCAAGTCCAGTCAGAGCCTTTTATATAGCAGCA

ATCAAAAGAACTACTTGGCCTGGTACCAACAGAAACCAGGGCAGTCTCCT

AAACTGCTGATTTACTGGGCATCCAGTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATATTATAACTAT

CCGCTCACGTTCGGTGCTGGGACCAAGTTGGAGCTGAAA

YP7 VL Amino Acid Sequence
(SEQ ID NO: 10)
DIVMSQSPSSLVVSIGEKVTMTCKSSQSLLYSSNQKNYLAWYQQKPGQSP

KLLIYWASSRESGVPDRFTGSGSGTDFTLTISSVKAEDLAVYYCQQYYNY

PLTFGAGTKLELK

TABLE 1A

Locations of the CDRs in the YP7 VH Sequence (according to Kabat)

| CDR | DNA Sequence (SEQ ID NO: 7) | Protein Sequence (SEQ ID NO: 8) |
|---|---|---|
| CDR1 | nucleotides 91-105 | amino acids 31-35 |
| CDR2 | nucleotides 148-204 | amino acids 50-68 |
| CDR3 | nucleotides 301-318 | amino acids 101-106 |

TABLE 1B

Locations of the CDRs in the YP7 VH Sequence (according to IMGT)

| CDR | DNA Sequence (SEQ ID NO: 7) | Protein Sequence (SEQ ID NO: 8) |
|---|---|---|
| CDR1 | nucleotides 76-99 | amino acids 26-33 |
| CDR2 | nucleotides 151-180 | amino acids 51-60 |
| CDR3 | nucleotides 295-318 | amino acids 99-106 |

TABLE 1C

Locations of the CDRs in the YP7 VL Sequence (according to Kabat)

| CDR | DNA Sequence (SEQ ID NO: 9) | Protein Sequence (SEQ ID NO: 10) |
|---|---|---|
| CDR1 | nucleotides 70-120 | amino acids 24-40 |
| CDR2 | nucleotides 166-186 | amino acids 56-62 |
| CDR3 | nucleotides 283-309 | amino acids 95-103 |

TABLE 1D

Locations of the CDRs in the YP7 VL Sequence (according to IMGT)

| CDR | DNA Sequence (SEQ ID NO: 9) | Protein Sequence (SEQ ID NO: 10) |
|---|---|---|
| CDR1 | nucleotides 79-114 | amino acids 27-38 |
| CDR2 | nucleotides 166-174 | amino acids 56-58 |
| CDR3 | nucleotides 283-309 | amino acids 95-103 |

YP9.1 VH DNA Sequence
(SEQ ID NO: 11)
GAGGTGCAGCTTGTTGAGACTGGCGGAGGATTGGTGCAGCCTGAAGGGTC

ATTGAAACTCTCATGTGCAACGTCTGGATTCAACTTCAATACCAATGCCA

TGAACTGGGTCCGCCAGGCTCCAGGAAAGGGTTTGGAATGGGTTGCTCGC

GTAAGAAATAAAACTAATAATTATGCAACATATTATGCCGATTCAGTGAA

-continued

AGACAGGTTCACCATCTCCAGAGATGATTCACAAAGAATGGTCTTTCTGC

AAATGAATAACTTGAAAACTGAGGACACAGCCATCTATTACTGTGTGGCG

GGGAACTCGTTTGCTTATTGGGGCCAAGGGACTCTGGTCACTGTCTCTCC

T

YP9.1 VH Protein Sequence
(SEQ ID NO: 12)
EVQLVETGGGLVQPEGSLKLSCATSGFNFNTNAMNWVRQAPGKGLEWVAR

VRNKTNNYATYYADSVKDRFTISRDDSQRMVFLQMNNLKTEDTAIYYCVA

GNSFAYWGQGTLVTVSP

YP9.1 VL DNA Sequence
(SEQ ID NO: 13)
GACATTGTGATGTCACAGTCTCCATCCTCCCTAGCTGTGTCAGTTGGAGA

GAGGGTTACTATGAACTGCAAGTCCAGTCAGAGTCTTTTATATAGTAGCA

ATCAAAAGAACTACTTGGCCTGGTACCAGCAGAAACCAGGGCAGTCTCCT

AAACTGCTGATTTACTGGGCATCCACTAGGGAATCTGGGGTCCCTGATCG

CTTCACAGGCAGTGTATCTGGGACAGATTTCACTCTCACCATCAGCAGTG

TGAAGGCTGAAGACCTGGCAGTTTATTACTGTCAGCAATATTATAACTAT

CCGCTCACGTTCGGTGCTGGGACCAAGCTGGAGCTGAAA

YP9.1 VL Protein Sequence
(SEQ ID NO: 14)
DIVMSQSPSSLAVSVGERVTMNCKSSQSLLYSSNQKNYLAWYQQKPGQSP

KLLIYWASTRESGVPDRFTGSVSGTDFTLTISSVKAEDLAVYYCQQYYNY

PLTFGAGTKLELK

TABLE 2A

Locations of the CDRs in the YP9.1 VH Sequence (according to Kabat)

| CDR | DNA Sequence (SEQ ID NO: 11) | Protein Sequence (SEQ ID NO: 12) |
|---|---|---|
| CDR1 | nucleotides 91-105 | amino acids 31-35 |
| CDR2 | nucleotides 148-204 | amino acids 50-68 |
| CDR3 | nucleotides 301-318 | amino acids 101-106 |

TABLE 2B

Locations of the CDRs in the YP9.1 VH Sequence (according to IMGT)

| CDR | DNA Sequence (SEQ ID NO: 11) | Protein Sequence (SEQ ID NO: 12) |
|---|---|---|
| CDR1 | nucleotides 76-99 | amino acids 26-33 |
| CDR2 | nucleotides 151-180 | amino acids 51-60 |
| CDR3 | nucleotides 295-318 | amino acids 99-106 |

TABLE 2C

Locations of the CDRs in the YP9.1 VL Sequence (according to Kabat)

| CDR | DNA Sequence (SEQ ID NO: 13) | Protein Sequence (SEQ ID NO: 14) |
|---|---|---|
| CDR1 | nucleotides 70-120 | amino acids 24-40 |
| CDR2 | nucleotides 166-186 | amino acids 56-62 |
| CDR3 | nucleotides 283-309 | amino acids 95-103 |

TABLE 2D

Locations of the CDRs in the YP9.1 VL Sequence (according to IMGT)

| CDR | DNA Sequence (SEQ ID NO: 13) | Protein Sequence (SEQ ID NO: 14) |
|---|---|---|
| CDR1 | nucleotides 79-114 | amino acids 27-38 |
| CDR2 | nucleotides 166-174 | amino acids 56-58 |
| CDR3 | nucleotides 283-309 | amino acids 95-103 |

YP8 VH Nucleotide Sequence
(SEQ ID NO: 15)
GAGGTGCAGCTTGTTGGAAGTGGTGGAGGATTGGTGCAGCCTGAAGGGTC

ATTGAAACTCTCATGTGCAGCCTCTGGATTCACCTTCAAGACCAATGCCA

TGAACTGGGTCCGCCAGGCTCCAGGAAAGGGTTTGGAATGGGTTGCTCGC

ATAAGAAATAAAACTAATAATTATGCAACATATTATGCCGACTCAGTGAA

AGACAGGTTCACCATCTCCAGAGATGATTCACAAAGCATGCTCTATCTGC

AAATGAACAACTTGAAAACTGAAGACACAGCCATGTATTTCTGTGTGGCC

GGTAACTCGTTTGCTTACTGGGGCCAGGGGACTCTGGTCACTGTCTCTGC

A

YP8 VH Amino Acid Sequence
(SEQ ID NO: 16)
EVQLVGSGGGLVQPEGSLKLSCAASGFTFKTNAMNWVRQAPGKGLEWVAR

IRNKTNNYATYYADSVKDRFTISRDDSQSMLYLQMNNLKTEDTAMYFCVA

GNSFAYWGQGTLVTVSA

YP8 VL Nucleotide Sequence
(SEQ ID NO: 17)
GACATTGTGATGTCACAGTCTCCATCCTCCCTAGCTGTGTCAGTTGGAGA

GAAGGTTACTGTGAACTGCAAGTCCAGTCAGAGCCTTTTATATAGTAACA

ATCAAAAGAACTACTTGGCCTGGTACCAGCAGAAACCAGGGCAGTCTCCT

AAACTGCTGATTTACTGGGCATCAACTAGGGAATATGGGGTCCCTGATCG

CTTCACAGGCAGTGGATCTGGGACAGATTTCACTCTCACCATCAGCAGTG

TGAAGGCTGAAGACCTGGCAGTTTATTACTGTCAGCAATATTATAACTAT

CCGCTCACGTTCGGTGCTGGGACCAAGCTGGAGCTGAAA

YP8 VL Amino Acid Sequence
(SEQ ID NO: 18)
DIVMSQSPSSLAVSVGEKVTVNCKSSQSLLYSNNQKNYLAWYQQKPGQSP

KLLIYWASTREYGVPDRFTGSGSGTDFTLTISSVKAEDLAVYYCQQYYNY

PLTFGAGTKLELK

TABLE 3A

Locations of the CDRs in the YP8 VH Sequence (according to Kabat)

| CDR | DNA Sequence (SEQ ID NO: 15) | Protein Sequence (SEQ ID NO: 16) |
|---|---|---|
| CDR1 | nucleotides 91-105 | amino acids 31-35 |
| CDR2 | nucleotides 148-204 | amino acids 50-68 |
| CDR3 | nucleotides 301-318 | amino acids 101-106 |

TABLE 3B

Locations of the CDRs in the YP8
VH Sequence (according to IMGT)

| CDR | DNA Sequence (SEQ ID NO: 15) | Protein Sequence (SEQ ID NO: 16) |
|---|---|---|
| CDR1 | nucleotides 76-99 | amino acids 26-33 |
| CDR2 | nucleotides 151-180 | amino acids 51-60 |
| CDR3 | nucleotides 295-318 | amino acids 99-106 |

TABLE 3C

Locations of the CDRs in the YP8
VL Sequence (according to Kabat)

| CDR | DNA Sequence (SEQ ID NO: 17) | Protein Sequence (SEQ ID NO: 18) |
|---|---|---|
| CDR1 | nucleotides 70-120 | amino acids 24-40 |
| CDR2 | nucleotides 166-186 | amino acids 56-62 |
| CDR3 | nucleotides 283-309 | amino acids 95-103 |

TABLE 3D

Locations of the CDRs in the YP8
VL Sequence (according to IMGT)

| CDR | DNA Sequence (SEQ ID NO: 17) | Protein Sequence (SEQ ID NO: 18) |
|---|---|---|
| CDR1 | nucleotides 79-114 | amino acids 27-38 |
| CDR2 | nucleotides 166-174 | amino acids 56-58 |
| CDR3 | nucleotides 283-309 | amino acids 95-103 |

```
YP9 VH Nucleotide Sequence
                                    (SEQ ID NO: 19)
GAGGTCCAGCTTGTTGAGACTGGTGGAGGATTGGTGCAGCCTAAAGGGTC
ATTGAAACTCTCATGTGCAGCCTCTGGATTCACCTTCAATACCAATGCCA
TGAACTGGGTCCGCCAGGCTCCAGGAAAGGGTTTGCAATGGGTTGCTCGC
GTAAGAAATAAAACTAATAATTATGCAACATATTATGCCGATTCCGTGAA
AGACAGGTTCACCATCTCCAGAGATGATTCACAAAGCATGCTCTATCTGC
AAATGAACAACTTGAAAACTGAAGACACGGCCATTTATTACTGTGTGGGG
GGTAACTCGTTTGCTTACTGGGGCCAAGGGACTCTGGTCACTGTCTCTGC
A YP9 VH Amino Acid Sequence
                                    (SEQ ID NO: 20)
EVQLVETGGGLVQPKGSLKLSCAASGFTFNTNAMNWVRQAPGKGLQWVAR
VRNKTNNYATYYADSVKDRFTISRDDSQSMLYLQMNNLKTEDTAIYYCVG
GNSFAYWGQGTLVTVSA YP9 clone 9 VL Nucleotide Sequence
                                    (SEQ ID NO: 21)
GACATTGTGATGTCCCAGTCTCCATCCTCCCTAGCTGTGTCAGTTGGAGA
GAAGGTTACTATGAGCTGCAAGTCCAGTCAGAGCCTTTTATATAGTAACA
ATCAAAAGAACTACTTGGCCTGGTACCACCAGAAACCAGGGCAGTCTCCT
AAACTGCTGATTTACTGGGCATCCACTAGGGAATCTGGGGTCCCTGATCG
CTTCACAGGCAGTGGATCTGGGACAGATTTCACTCTCACCATCAGCAGTG
TGAAGGCTGAAGACCTGGCAGTTTATTACTGTCAGCAATATTATAGCTAT
CCACTCACGTTCGGTGCTGGGACCAAGCTGGAGCTGAAA YP9 clone 9 VL Amino Acid Sequence
                                    (SEQ ID NO: 22)
DIVMSQSPSSLAVSVGEKVTMSCKSSQSLLYSNNQKNYLAWYHQKPGQSP
KLLIYWASTRESGVPDRFTGSGSGTDFTLTISSVKAEDLAVYYCQQYYSY
PLTFGAGTKLELK YP9 clone 10 VL Nucleotide Sequence
                                    (SEQ ID NO: 23)
GACATTGTGATGTCCCAGTCTCCATCCTCCCTAGCTGTGTCAGTTGGAGA
GAAGGTTACTATGAGCTGCAAGTCCAGTCAGAGCCTTTTATATAGTAACA
ATCAAAAGAACTACTTGGCCTGGTACCACCAGAAACCAGGGCAGTCTCCT
AAACTGCTGATTTACTGGGCATCCACTAGGGAATCTGGGGTCCCTGATCG
CTTCACAGGCAGTGGATCTGGGACAGATTTCACTCTCACCATCAGCAGTG
TGAAGGCTGAAGACCTGGCAGTTTATTACTGTCAGCAATATTATATCTAT
CCACTCACGTTCGGTGCTGGGACCAAGCTGGAGCTGAAA YP9 clone 10 VL Amino Acid Sequence
                                    (SEQ ID NO: 24)
DIVMSQSPSSLAVSVGEKVTMSCKSSQSLLYSNNQKNYLAWYHQKPGQSP
KLLIYWASTRESGVPDRFTGSGSGTDFTLTISSVKAEDLAVYYCQQYYIY
PLTFGAGTKLELK YP9 clone 1 VL Nucleotide Sequence
                                    (SEQ ID NO: 25)
GACATTGTGATGTCCCAGTCTCCATCCTCCCTAGCTGTGTCAGTTGGAGA
GAAGGTTACTATGAGCTGCAAGTCCAGTCAGAGCCTTTTATATAGTAACA
ATCAAAAGAACTACTTGGCCTGGTACCACCAGAAACCAGGGCAGTCTCCT
AAACTGCTGATTTACTGGGCATCCACTAGGGAATCTGGGGTCCCTGATCG
CTTCACAGGCAGTGGATCTGGGACAGATTTCACTCTCACCATCAGCAGTG
TGAAGGCTGAAGACCTGGCAGTTTATTACTGTCAGCAATATTATAGCTAT
CCACTCACGTTCGGTGCTGGGACCAAGCTGGAAATAAAA YP9 clone 1 VL Amino Acid Sequence
                                    (SEQ ID NO: 26)
DIVMSQSPSSLAVSVGEKVTMSCKSSQSLLYSNNQKNYLAWYHQKPGQSP
KLLIYWASTRESGVPDRFTGSGSGTDFTLTISSVKAEDLAVYYCQQYYSY
PLTFGAGTKLEIK
```

TABLE 4A

Locations of the CDRs in the YP9
VH Sequence (according to Kabat)

| CDR | DNA Sequence (SEQ ID NO: 19) | Protein Sequence (SEQ ID NO: 20) |
|---|---|---|
| CDR1 | nucleotides 91-105 | amino acids 31-35 |
| CDR2 | nucleotides 148-204 | amino acids 50-68 |
| CDR3 | nucleotides 301-318 | amino acids 101-106 |

TABLE 4B

Locations of the CDRs in the YP9
VH Sequence (according to IMGT)

| CDR | DNA Sequence (SEQ ID NO: 19) | Protein Sequence (SEQ ID NO: 20) |
|---|---|---|
| CDR1 | nucleotides 76-99 | amino acids 26-33 |
| CDR2 | nucleotides 151-180 | amino acids 51-60 |
| CDR3 | nucleotides 295-318 | amino acids 99-106 |

TABLE 4C

Locations of the CDRs in the YP9
VL Sequence (according to Kabat)

| CDR | DNA Sequence (SEQ ID NOs: 21, 23 and 25) | Protein Sequence (SEQ ID NOs: 22, 24 and 26) |
|---|---|---|
| CDR1 | nucleotides 70-120 | amino acids 24-40 |
| CDR2 | nucleotides 166-186 | amino acids 56-62 |
| CDR3 | nucleotides 283-309 | amino acids 95-103 |

TABLE 4D

Locations of the CDRs in the YP9
VL Sequence (according to IMGT)

| CDR | DNA Sequence (SEQ ID NOs: 21, 23 and 25) | Protein Sequence (SEQ ID NOs: 22, 24 and 26) |
|---|---|---|
| CDR1 | nucleotides 79-114 | amino acids 27-38 |
| CDR2 | nucleotides 166-174 | amino acids 56-58 |
| CDR3 | nucleotides 283-309 | amino acids 95-103 |

Sequencing of the VL domain of the YP6 antibody determined that the nucleotide and amino acid sequences of YP6 VL are identical to the YP8 VL nucleotide and amino acid sequences (SEQ ID NO: 17 and SEQ ID NO: 18, respectively). Sequencing of the VH domain of the YP6 antibody identified two clones, referred to as clone 4 and clone 7. The YP6 clone 4 VH domain sequences are identical to the YP8 VH domain nucleotide and amino acid sequences (SEQ ID NO: 15 and SEQ ID NO: 16, respectively). The YP6 clone 7 VH domain sequence differs from the clone 4 sequence by a single amino acid residue immediately following H-CDR3 (a tryptophan to leucine change). The YP6 VH nucleotide and amino acid sequences are set forth herein as SEQ ID NO: 36 and SEQ ID NO: 37, respectively (see also FIG. 5 and FIG. 6).

As shown in FIGS. 6 and 8, the CDR sequences of each antibody are highly similar. Therefore, consensus VL and VH CDR sequences (both IMGT and Kabat) were determined.

```
HCDR1 (IMGT):
                                              (SEQ ID NO: 38)
GFX₁FX₂X₃NA,
where X₁ = T or N, X₂ = K or N and X₃ = T or K HCDR2 (IMGT):
                                              (SEQ ID NO: 39)
XRNKTNNYAT,
where X = I or V HCDR3 (IMGT):
                                              (SEQ ID NO: 40)
VXGNSFAY,
where X = A or G HCDR1 (Kabat):
                                              (SEQ ID NO: 41)
XNAMN,
where X = T or K HCDR2 (Kabat):
                                              (SEQ ID NO: 42)
RX₁RNKTNNYATYYADSVKX₂,
where X₁ = I or V and X₂ = D or A HCDR3 (Kabat):
                                              (SEQ ID NO: 43)
GNSFAY LCDR1 (IMGT):
                                              (SEQ ID NO: 44)
QSLLYSNNQKNY LCDR2 (IMGT):
                                 (residues 56-58 of SEQ ID NO: 14)
WAS LCDR3 (IMGT):
                                              (SEQ ID NO: 45)
QQYYXYPLT,
where X = S, I or N LCDR1 (Kabat):
                                              (SEQ ID NO: 46)
KSSQSLLYSNNQKNYLA LCDR2 (Kabat):
                                              (SEQ ID NO: 47)
WASX₁REX₂,
where X₁ = T or S and X₂ = S or Y LCDR3 (Kabat):
                                              (SEQ ID NO: 45)
QQYYXYPLT,
where X = S, I or N
```

Provided herein are isolated monoclonal antibodies that bind (for example, specifically bind) GPC3, such as cell-surface or soluble GPC3. In some embodiments, the heavy chain of the antibody comprises at least a portion of the amino acid sequence set forth herein as SEQ ID NO: 8 (YP7), SEQ ID NO: 12 (YP9.1), SEQ ID NO: 16 (YP8 and VP6 clone 4), SEQ ID NO: 37 (YP6 clone 7) or SEQ ID NO: 20 (YP9), such as one or more (such as all three) CDR sequences from SEQ ID NO: 8, 12, 16, 20 or 37, as determined by IMGT. In other embodiments, the antibodies comprise one or more (such as all three) CDR sequences from SEQ ID NO: 8, 12, 16, 20 or 37, as determined using the Kabat method. In some embodiments, the light chain of the antibody comprises at least a portion of the amino acid sequence set forth herein as SEQ ID NO: 10 (YP7), SEQ ID NO: 14 (YP9.1), SEQ ID NO: 18 (YP8 and YP6), SEQ ID NO: 22 (YP9, clone 9), SEQ ID NO: 24 (YP9, clone 10) or SEQ ID NO: 26 (YP9, clone 1), such as one or more (such as all three) CDR sequences from SEQ ID NO: 10, 14, 18, 22, 24 or 26, as determined by IMGT. In other embodiments, the antibodies comprise one or more (such as all three) CDR sequences from SEQ ID NO: 10, 14, 18, 22, 24 or 26, as determined using the Kabat method.

In some embodiments, the heavy chain of the antibody that binds GPC3 comprises amino acid residues 26-33, 51-60 and 99-106 of SEQ ID NO: 8; and/or the light chain of the antibody comprises amino acid residues 27-38, 56-58 and 95-103 of SEQ ID NO: 10. In other embodiments, the heavy chain comprises amino acid residues 31-35, 50-68 and 101-106 of SEQ ID NO: 8; and/or the light chain of the antibody comprises amino acid residues 24-40, 56-62 and 95-103 of SEQ ID NO: 10. In some examples, the amino acid sequence of the heavy chain is at least 90%, at least 95%, at least 96%, at least 97%, at least 98% or at least 99% identical to SEQ ID NO: 8; and/or the amino acid sequence of the light chain is at least 90%, at least 95%, at least 96%, at least 97%, at least 98% or at least 99% identical to SEQ ID NO: 10. In particular examples, the heavy chain of the antibody comprises SEQ ID NO: 8 and/or the light chain of the antibody comprises SEQ ID NO: 10.

In some embodiments, the heavy chain of the antibody that binds GPC3 comprises amino acid residues 26-33, 51-60 and 99-106 of SEQ ID NO: 12; and/or the light chain of the antibody comprises amino acid residues 27-38, 56-58 and 95-103 of SEQ ID NO: 14. In other embodiments, the heavy chain comprises amino acid residues 31-35, 50-68 and 101-106 of SEQ ID NO: 12; and/or the light chain of the antibody comprises amino acid residues 24-40, 56-62 and 95-103 of SEQ ID NO: 14. In some examples, the amino acid sequence of the heavy chain is at least 90%, at least 95%, at least 96%, at least 97%, at least 98% or at least 99% identical to SEQ ID NO: 12; and/or the amino acid sequence of the light chain at least 90%, at least 95%, at least 96%, at least 97%, at least 98% or at least 99% identical to SEQ ID NO: 14. In particular examples, the heavy chain of the antibody comprises SEQ ID NO: 12 and/or the light chain of the antibody comprises SEQ ID NO: 14.

In some embodiments, the heavy chain of the antibody that binds GPC3 comprises amino acid residues 26-33, 51-60 and 99-106 of SEQ ID NO: 16; and/or the light chain of the antibody comprises amino acid residues 27-38, 56-58 and 95-103 of SEQ ID NO: 18. In other embodiments, the heavy chain comprises amino acid residues 31-35, 50-68 and 101-106 of SEQ ID NO: 16; and/or the light chain of the antibody comprises amino acid residues 24-40, 56-62 and 95-103 of SEQ ID NO: 18. In some examples, the amino acid sequence of the heavy chain is at least 90%, at least 95%, at least 96%, at least 97%, at least 98% or at least 99% identical to SEQ ID NO: 16; and/or the amino acid sequence of the light chain is at least 90%, at least 95%, at least 96%, at least 97%, at least 98% or at least 99% identical to SEQ ID NO: 18. In particular examples, the heavy chain of the antibody comprises SEQ ID NO: 16 or SEQ ID NO: 37 and/or the light chain of the antibody comprises SEQ ID NO: 18.

In some embodiments, the heavy chain of the antibody that binds GPC3 comprises amino acid residues 26-33, 51-60 and 99-106 of SEQ ID NO: 20; and/or the light chain of the antibody comprises amino acid residues 27-38, 56-58 and 95-103 of SEQ ID NO: 22, 24 or 26. In other embodiments, the heavy chain comprises amino acid residues 31-35, 50-68 and 101-106 of SEQ ID NO: 20; and/or the light chain of the antibody comprises amino acid residues 24-40, 56-62 and 95-103 of SEQ ID NO: 22, 24 or 26. In some examples, the amino acid sequence of the heavy chain is at least 90%, at least 95%, at least 96%, at least 97%, at least 98% or at least 99% identical to SEQ ID NO: 20; and/or the amino acid sequence of the light chain is at least 90%, at least 95%, at least 96%, at least 97%, at least 98% or at least 99% identical to SEQ ID NO: 22, 24 or 26. In particular examples, the heavy chain of the antibody comprises SEQ ID NO: 20 and/or the light chain of the antibody comprises SEQ ID NO: 22, 24 or 26.

In some embodiments, the heavy chain of the antibody comprises SEQ ID NO: 38, SEQ ID NO: 39 and SEQ ID NO: 40, and the light chain of the antibody comprises SEQ ID NO: 44, amino acid residues 56-58 of SEQ ID NO: 14, and SEQ ID NO: 45. In other embodiments, the heavy chain of the antibody comprises SEQ ID NO: 41, SEQ ID NO: 42 and SEQ ID NO: 43, and the light chain of the antibody comprises SEQ ID NO: 46, SEQ ID NO: 47 and SEQ ID NO: 45.

Also provided are isolated monoclonal antibodies that bind, such as specifically bind, GPC3, wherein the antibody comprises a variable heavy (VH) domain comprising the amino acid sequence of SEQ ID NO: 8, SEQ ID NO: 12, SEQ ID NO: 16 or SEQ ID NO: 20; and/or a variable light (VL) domain comprising the amino acid sequence of SEQ ID NO: 10, SEQ ID NO: 14, SEQ ID NO: 18, SEQ ID NO: 22, SEQ ID NO: 24 or SEQ ID NO: 26.

In some embodiments, the VH domain of the antibody comprises SEQ ID NO: 8 and/or the VL domain of the antibody comprises SEQ ID NO: 10.

In some embodiments, the VH domain of the antibody comprises SEQ ID NO: 12 and/or the VL domain of the antibody comprises SEQ ID NO: 14.

In some embodiments, the VH domain of the antibody comprises SEQ ID NO: 16 and/or the VL domain of the antibody comprises SEQ ID NO: 18.

In some embodiments, the VH domain of the antibody comprises SEQ ID NO: 37 and/or the VL domain of the antibody comprises SEQ ID NO: 18.

In some embodiments, the VH domain of the antibody comprises SEQ ID NO: 20 and/or the VL domain of the antibody comprises SEQ ID NO: 22, 24 or 26.

In some embodiments, the monoclonal antibodies that bind, such as specifically bind, GPC3 are humanized antibodies.

In some embodiments, the monoclonal antibody that binds, such as specifically binds, GPC3 is a VH single-domain antibody, a Fab fragment, a Fab' fragment, a F(ab)'$_2$ fragment, a single chain variable fragment (scFv), or a disulfide stabilized variable fragment (dsFv). In other embodiments, the antibody is an immunoglobulin molecule. In particular examples, the antibody is an IgG.

In some embodiments, the disclosed antibodies bind GPC3 (soluble or cell-surface GPC3) with a dissociation constant ($K_d$) of about 1 nM or less. In several embodiments, the human monoclonal antibodies bind GPC3 with a binding affinity of about 1 nM, about 0.9 nM, about 0.8 nM, about 0.7 nM, about 0.6 nM, about 0.5 nM, about 0.4 nM, about 0.3 nM, about 0.2 nM, about 0.15 nM, about 0.1 nM, about 0.05 nM, about 0.04 nM, about 0.03 nM, about 0.02 nM or about 0.01 nM.

The isolated human monoclonal antibodies disclosed herein can be labeled, such as with a fluorescent, enzymatic, or radioactive label.

Further provided herein are compositions comprising a therapeutically effective amount of the disclosed antibodies and a pharmaceutically acceptable carrier.

Immunoconjugates comprising the human monoclonal antibodies disclosed herein and an effector molecule are also provided. The effector molecule can be, for example, a toxin or a detectable label. In some embodiments, the immunoconjugate comprises the VH and VL domain of one of the anti-GPC3 antibodies disclosed herein and a toxin, such as PE or a variant therefore, such as PE38. In some examples, the immunoconjugate comprises the VH and VL of YP7, the VH and VL of YP8, the VH and VL of YP9 clone 9, or the VH and VL of YP9.1 fused to PE38. In non-limiting examples, the amino acid sequence of the immunoconjugate comprises residues 2-597 of SEQ ID NO: 28, residues 2-597 of SEQ ID NO: 31, residues 2-597 of SEQ ID NO: 33 or residues 2-597 of SEQ ID NO: 35. Examples of immunoconjugates are discussed in greater detail in section VI below. Also provided are compositions comprising a therapeutically effective amount of the immunoconjugates disclosed herein and a pharmaceutically acceptable carrier.

Further provided herein are isolated nucleic acid molecules encoding the disclosed monoclonal antibodies. In some embodiments, the nucleotide sequence encoding the heavy chain of the monoclonal antibody comprises at least a portion of SEQ ID NO: 7, 11, 15, 19 or 36, such as the portion encoding one or more CDRs of SEQ ID NO: 7, 11, 15, 19 or 36. In some examples, the heavy chain of the human monoclonal antibody comprises the nucleotide sequence of SEQ ID NO: 7, 11, 15, 19 or 36. In some embodiments, the nucleotide sequence encoding the light chain of the monoclonal antibody comprises at least a portion of SEQ ID NO: 9, 13, 17, 21, 23 or 25, such as a portion encoding one or more CDRs of SEQ ID NO: 9, 13, 17, 21, 23 or 25. In some examples, the light chain of the human monoclonal antibody comprises the nucleotide sequence of SEQ ID NO: 9, 13, 17, 21, 23 or 25.

In some examples, the isolated nucleic acid molecule is operably linked to a promoter.

Also provided are expression vectors comprising the isolated nucleic acid molecules disclosed herein. Isolated host cells comprising the nucleic acid molecules or vectors are also provided herein. In some examples, the host cell is a T cell, such as a cytotoxic T lymphocyte (CTL).

V. Antibody and Antibody Fragments

The monoclonal antibodies disclosed herein can be of any isotype. The monoclonal antibody can be, for example, an IgM or an IgG antibody, such as IgG$_1$ or an IgG$_2$. The class of an antibody that specifically binds GPC3 can be switched with another (for example, IgG can be switched to IgM), according to well-known procedures. Class switching can also be used to convert one IgG subclass to another, such as from IgG$_1$ to IgG$_2$.

Antibody fragments are also encompassed by the present disclosure, such as single-domain antibodies (e.g., VH domain antibodies), Fab, F(ab')$_2$, and Fv. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody (scFV$_2$), defined as a dimer of a scFV (also known as a "miniantibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the V$_H$ and the V$_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the V$_H$ and/or the V$_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

VI. Immunoconjugates

The disclosed monoclonal antibodies specific for GPC3 can be conjugated to a therapeutic agent or effector molecule. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}$I, $^{32}$P, $^{14}$C, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

An antibody that binds (for example specifically binds) GPC3 can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect GPC3 by x-ray, emission spectra, or other diagnostic techniques. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; PCT Publication No. WO 99/51643; Pai et al., *Proc. Natl Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

The full-length PE sequence is set forth herein as SEQ ID NO: 29:

AEEAFDLWNECAKACVLDLKDGVRSSRMSVDPAIADTNGQGVLHYSMVLE

GGNDALKLAIDNALSITSDGLTIRLEGGVEPNKPVRYSYTRQARGSWSLN

WLVPIGHEKPSNIKVFIHELNAGNQLSHMSPIYTIEMGDELLAKLARDAT

FFVRAHESNEMQPTLAISHAGVSVVMAQTQPRREKRWSEWASGKVLCLLD

PLDGVYNYLAQQRCNLDDTWEGKIYRVLAGNPAKHDLDIKPTVISHRLHF

PEGGSLAALTAHQACHLPLETFTRHRQPRGWEQLEQCGYPVQRLVALYLA

ARLSWNQVDQVIRNALASPGSGGDLGEAIREQPEQARLALTLAAAESERF

VRQGTGNDEAGAANADVVSLTCPVAAGECAGPADSGDALLERNYPTGAEF

LGDGGDVSFSTRGTQNWTVERLLQAHRQLEERGYVFVGYHGTFLEAAQSI

VFGGVRARSQDLDAIWRGFYIAGDPALAYGYAQDQEPDARGRIRNGALLR

VYVPRSSLPGFYRTSLTLAAPEAAGEVERLIGHPLPLRLDAITGPEEEGG

RLETILGWPLAERTVVIPSAIPTDPRNVGGDLDPSSIPDKEQAISALPDY

ASQPGKPPREDLK

In some examples, the PE is PE38, comprising the following amino acid sequence:

(SEQ ID NO: 1)
GGSLAALTAHQACHLPLETFTRHRQPRGWEQLEQCGYPVQRLVALYLAAR

LSWNQVDQVIRNALASPGSGGDLGEAIREQPEQARLALTLAAAESERFVR

QGTGNDEAGAANGPADSGDALLERNYPTGAEFLGDGGDVSFSTRGTQNWT

VERLLQAHRQLEERGYVFVGYHGTFLEAAQSIVFGGVRARSQDLDAIWRG

FYIAGDPALAYGYAQDQEPDARGRIRNGALLRVYVPRSSLPGFYRTSLTL

AAPEAAGEVERLIGHPLPLRLDAITGPEEEGGRLETILGWPLAERTVVIP

SAIPTDPRNVGGDLDPSSIPDKEQAISALPDYASQPGKPPREDLK

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105 (32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954) having the following amino acid sequence:

(SEQ ID NO: 2)
RHRQPRGWEQLPTGAEFLGDGGDVSFSTRGTQNWTVERLLQAHRQLEERG

YVFVGYHGTFLEAAQSIVFGGVRARSQDLDAIWRGFYIAGDPALAYGYAQ

DQEPDARGRIRNGALLRVYVPRSSLPGFYRTSLTLAAPEAAGEVERLIGH

PLPLRLDAITGPEEEGGRLETILGWPLAERTVVIPSAIPTDPRNVGGDLD

PSSIPDKEQAISALPDYASQPGKPPREDLK

In other examples, the PE is a variant designated PE-LR/6X (PCT Publication No. WO 2011/032022) having the following amino acid sequence:

(SEQ ID NO: 3)
RHRQPRGWEQLPTGAEFLGDGGDVSFSTRGTQNWTVERLLQAHRQLEEGG

YVFVGYHGTFLEAAQSIVFGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEESGGRLETILGWPLAERTVVIPSAIPTDPRNVGGDLD

PSSIPDSEQAISALPDYASQPGKPPREDLK

In other examples, the PE variant is PE with reducing immunogenicity, such as a PE with the following sequence:

(X = G, A or S; SEQ ID NO: 4)
RHRQPRGWEQLPTGAEFLGDGGXVSFSTRGTQNWTVERLLQAHRQLEEXG

YVFVGYHGTFLEAAQSIVFGGVRARSQDLDAIWXGFYIAGDPALAYGYAQ

DQEPDAXGRIRNGALLRVYVPRSSLPGFYXTSLTLAAPEAAGEVERLIGH

PLPLRLDAITGPEEXGGRLETILGWPLAERTVVIPSAIPTDPRNVGGDLD

PSSIPDXEXAISALPDYASQPGKPPREDLK

In other examples, the PE is a variant designated PE-LR/8M (PCT Publication No. WO 2011/032022) having the following amino acid sequence:

(SEQ ID NO: 5)
RHRQPRGWEQLPTGAEFLGDGGAVSFSTRGTQNWTVERLLQAHRQLEEGG

YVFVGYHGTFLEAAQSIVFGGVRARSQDLDAIWAGFYIAGDPALAYGYAQ

DQEPDAAGRIRNGALLRVYVPRSSLPGFYATSLTLAAPEAAGEVERLIGH

PLPLRLDAITGPEESGGRLETILGWPLAERTVVIPSAIPTDPRNVGGDLD

PSSIPDSEAAISALPDYASQPGKPPREDLK

Substitutions of PE are defined herein by reference to the amino acid sequence of full-length PE set forth herein as SEQ ID NO: 29. Substitutions of PE are described herein by reference to the amino acid residue present at a particular position, followed by the amino acid with which that residue has been replaced in the particular substitution. In this regard, the positions of the amino acid sequence of a particular embodiment of a PE are referred to herein as the positions of the amino acid sequence of the particular embodiment, or as the positions as defined by SEQ ID NO: 29. Thus, substitutions refer to a replacement of an amino acid residue in the amino acid sequence of a particular embodiment of a PE corresponding to the indicated position of the 613-amino acid sequence of SEQ ID NO: 29 with the understanding that the actual positions in the respective amino acid sequence may be different. In the event of multiple substitutions at two or more positions, the two or more substitutions may be the same or different—each amino acid residue of the two or more amino acid residues being substituted can be substituted with the same or different amino acid residue unless explicitly indicated otherwise.

Modification of PE may occur in any previously described variant, including cytotoxic fragments of PE (for example, PE38, PE-LR and PE-LR/8M). Modified PEs may include any substitution(s), as described above, for one or more amino acid residues within one or more T-cell epitopes and/or B cell epitopes of PE.

The antibodies described herein can also be used to target any number of different diagnostic or therapeutic compounds to cells expressing GPC3 on their surface. Thus, an antibody of the present disclosure can be attached directly or via a linker to a drug that is to be delivered directly to cells expressing cell-surface GPC3. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-GPC3 antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, $^3$H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

VII. Compositions and Methods of Use

Compositions are provided that include one or more of the disclosed antibodies that bind (for example specifically bind) GPC3 in a carrier. Compositions comprising immunoconjugates or immunotoxins are also provided. The compositions can be prepared in unit dosage forms for administration to a subject. The amount and timing of administration are at the discretion of the treating clinician to achieve the desired outcome. The antibody can be formulated for systemic or local (such as intra-tumor) administration. In one example, the antibody is formulated for parenteral administration, such as intravenous administration.

The compositions for administration can include a solution of the antibody dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice &

Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

A. Therapeutic Methods

The antibodies, compositions and immunoconjugates disclosed herein can be administered to slow or inhibit the growth of tumor cells or inhibit the metastasis of tumor cells, such as HCC, melanoma, ovarian clear cell carcinoma or squamous cell carcinoma of the lung tumor cells. In these applications, a therapeutically effective amount of an antibody is administered to a subject in an amount sufficient to inhibit growth, replication or metastasis of cancer cells, or to inhibit a sign or a symptom of the cancer. Suitable subjects may include those diagnosed with a cancer that expresses GPC3, such as, but not limited to, HCC, melanoma, ovarian clear cell carcinoma or squamous cell carcinoma of the lung.

In one non-limiting embodiment, provided herein is a method of treating a subject with cancer by selecting a subject with a cancer that expresses GPC3 and administering to the subject a therapeutically effective amount of an antibody, composition or immunoconjugate disclosed herein.

Also provided herein is a method of inhibiting tumor growth or metastasis by selecting a subject with a cancer that expresses GPC3 and administering to the subject a therapeutically effective amount of an antibody, composition or immunoconjugate disclosed herein.

A therapeutically effective amount of a human GPC3-specific antibody or immunoconjugate will depend upon the severity of the disease and the general state of the patient's health. A therapeutically effective amount of the antibody is that which provides either subjective relief of a symptom(s) or an objectively identifiable improvement as noted by the clinician or other qualified observer.

Administration of the antibodies and immunoconjugates disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of GPC3 in vitro or in vivo. In some cases, GPC3 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with a monoclonal antibody disclosed herein; and detecting binding of the antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with a monoclonal antibody disclosed herein; and detecting binding of the antibody to the sample. An increase in binding of the antibody to the sample as compared to binding of the antibody to a control sample confirms the diagnosis of cancer in the subject.

In some examples of the disclosed methods, the monoclonal antibody is directly labeled.

In some examples, the methods further include contacting a second antibody that specifically binds the monoclonal antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is HCC, melanoma, ovarian clear cell carcinoma or squamous cell carcinoma of the lung, or any other type of cancer that expresses GPC3.

In some examples, the control sample is a sample from a subject without cancer. In particular examples, the sample is a blood or tissue sample.

In some cases, the antibody that binds (for example specifically binds) GPC3 is directly labeled with a detectable label. In another embodiment, the antibody that binds (for example, specifically binds) GPC3 (the first antibody) is unlabeled and a second antibody or other molecule that can bind the antibody that specifically binds GPC3 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative embodiment, GPC3 can be assayed in a biological sample by a competition immunoassay utilizing GPC3 standards labeled with a detectable substance and an unlabeled antibody that specifically binds GPC3. In this assay, the biological sample, the labeled GPC3 standards and the antibody that specifically bind GPC3 are combined and the amount of labeled GPC3 standard bound to the unlabeled antibody is determined. The amount of GPC3 in the biological sample is inversely proportional to the amount of labeled GPC3 standard bound to the antibody that specifically binds GPC3.

The immunoassays and method disclosed herein can be used for a number of purposes. In one embodiment, the antibody that specifically binds GPC3 may be used to detect the production of GPC3 in cells in cell culture. In another embodiment, the antibody can be used to detect the amount of GPC3 in a biological sample, such as a tissue sample, or a blood or serum sample. In some examples, the GPC3 is cell-surface GPC3. In other examples, the GPC3 is soluble GPC3.

In one embodiment, a kit is provided for detecting GPC3 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble GPC3 protein or fragment. Kits for detecting a polypeptide will typically comprise a monoclonal antibody that specifically binds GPC3, such as any of the antibodies disclosed herein. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds GPC3. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting GPC3 in a biological sample generally includes the steps of contacting the biological sample with an antibody which specifically reacts, under immunologically reactive conditions, to a GPC3 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind GPC3, as disclosed herein, can be used in these assays. Thus, the antibodies can be used in a conventional immunoassay, includ- C. Engineered Cytotoxic T Lymphocytes (CTLs)

The disclosed monoclonal antibodies can also be used to produce CTLs engineered to express chimeric antigen receptors (CARs; also known as chimeric T cell receptors, artificial T cell receptors or chimeric immunoreceptors). Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a GPC3-specific antibody, thereby targeting the engineered CTLs to GPC3-expressing tumor cells. Engineered T cells have previously used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expressed the target antigen.

Accordingly, provided herein are CARs comprising a GPC3-specific antibody binding fragment, such as a scFv. Also provided are isolated nucleic acid molecules and vectors encoding the CARs, and host cells, such as CTLs, comprising the nucleic acid molecules or vectors. CTLs expressing CARs comprised of a GPC3-specific antibody binding fragment can be used for the treatment of cancers that express GPC3, such as HCC, melanoma, ovarian clear cell carcinoma or squamous cell carcinoma of the lung. Thus, provided herein are methods of treating a subject with cancer by selecting a subject with a cancer that expresses GPC3, and administering to the subject a therapeutically effective amount of the CTLs expressing the GPC3-targeted CARs.

D. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting both CTLs (such as a CTL receptor component such as CD3) and a tumor antigen. The GPC3-specific monoclonal antibodies disclosed herein can be used to generate bispecific antibodies that target both GPC3 and CTLs, thereby providing a means to treat GPC3-expressing cancers.

Provided herein are bispecific monoclonal antibodies comprising a GPC3-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. Also provided are isolated nucleic acid molecules and vectors encoding the bispecific antibodies, and host cells comprising the nucleic acid molecules or vectors. Bispecific antibodies comprising a GPC3-specific antibody, or antigen-binding fragment thereof, can be used for the treatment of cancers that express GPC3, such as HCC, melanoma, ovarian clear cell carcinoma or squamous cell carcinoma of the lung. Thus, provided herein are methods of treating a subject with cancer by selecting a subject with a cancer that expresses GPC3, and administering to the subject a therapeutically effective amount of the GPC3-targeting bispecific antibody.

The following examples are provided to illustrate certain particular features and/or embodiments. These examples should not be construed to limit the disclosure to the particular features or embodiments described.

EXAMPLES

Example 1

Materials and Methods

This example describes the materials and experimental methods for the studies described in Example 2.

Cell Lines

Six human HCC cell lines (SK-Hep1, HepG2, Hep3B, Huh-1, Huh-4, and Huh-7) and five human CCA lines (HuCCT1, OZ, Mz-ChA-1, KMBC, and KMCH) were used in the studies described below. The TOV-21G cell line (human ovarian clear cell carcinoma cell line) was obtained from the American Type Culture Collection (Manassas, Va.). A431/G1 is a transfected A431 human epithelial carcinoma cell line that stably expresses human GPC3. The cell lines were cultured as described in Yu et al. (*J Cancer* 1:141-149, 2010).

Monoclonal Antibody Production

Mouse hybridoma technology included peptide synthesis, mice immunization, cell fusion of mouse spleen cells, hybridoma selection and expansion, and supernatant screening using peptide or protein (E. Harlow, D. Lane (1988) Antibodies: a laboratory manual, Cold Spring Harbor Laboratory, Cold Spring Harbor, N.Y.). In brief, a peptide consisting of 50 residues (DGMIKVKNQLRFLAELAYDLDVDDAPGN-SQQATPKDNEISTFHNLGNVHS; SEQ ID NO: 6) was synthesized (GenScript USA, Piscataway, N.J.) and conjugated to a carrier protein, keyhole limpet hemocyanin (KLH), by maleimide chemistry via a cysteine residue introduced at the N-terminus. Five BALB/c mice were immunized, followed by test bleeds after second and third immunizations, with two fusions performed on mice showing the highest antibody titers (>10,000 on GPC3-expressing cancer cells). Hybridoma cells were screened via flow cytometry (as described below). The most positive five clones were selected for subcloning, the immunoglobulin (Ig) isotype was determined, and the clones were further expanded. The YP7 clone, which demonstrated the highest affinity and most specific binding, was chosen for purification via ascites production in BALB/c mice and protein A purification (E. Harlow, D. Lane (1988) Antibodies: a laboratory manual, Cold Spring Harbor Laboratory, Cold Spring Harbor, N.Y.).

High-Throughput Flow Cytometry

Cells were incubated with mouse hybridoma supernatant containing 1 µg/mL of each mAb. Binding was detected with goat anti-mouse IgG conjugated with phycoerythrin (PE) (Sigma-Aldrich, St. Louis, Mo.). The fluorescence associated with live cells was measured using a FACSCalibur (BD Biosciences, San Jose, Calif.). For screening of hybridomas, a 1:1 mixture of A431 and A431/G1 cells (10,000 cells per well in 96-well plates) were incubated with a 1:5 dilution of mouse hybridoma supernatant. Binding was detected with goat anti-mouse IgG conjugated with PE (Sigma-Aldrich, St. Louis, Mo.). Fluorescence was measured using Guava EasyCyte Plus instrument equipped with a built-in autosampler (Millipore, Billerica, Mass.). Geomean values for A431/G1 and A431 were measured simultaneously for individual clones using Guava Express Pro Software. Clones with binding ratios of 15 or more were considered specific to cell-associated GPC3 protein and selected for further flow cytometry using HepG2 cells.

The Scatchard plot and the $K_D$ value were calculated using Prism (GraphPad Software Inc., San Diego, Calif.) as previously described (Ho et al., *J Biol Chem* 280:607-617, 2005).

Enzyme-Linked Immunosorbent Assay (ELISA)

Nunc MaxiSorp 96-well flat-bottom plates were incubated overnight with 1 μg/ml of wild-type or mutant GPC3 (GPC3ΔHS, a GPC3 mutant without heparan sulfate) protein in PBS at 4° C. followed by blocking with SuperBlock buffer (Thermo Fisher Scientific Inc., Rockford, Ill.). Recombinant GPC3 proteins were made (Yu et al., *J Cancer* 1:141-149, 2010) and recombinant GPC1 and GPC5 proteins were purchased (R&D Systems, Minneapolis, Minn.). Mouse sera were diluted 1:5 in PBST buffer (0.05% Tween 20) and incubated in the same plate for 1 hour at room temperature. To detect bound antibodies, a 1:10,000 dilution of goat anti-mouse IgG conjugated with horseradish peroxidase (HRP, Invitrogen, Carlsbad, Calif.) was added. Assays were developed as described (Ho et al., *J Biol Chem* 280:607-617, 2005).

Immunoprecipitation and Western Blot Analysis

Supernatants of cultured cells were incubated with 1 μg/mL of purified mouse hybridoma antibody or a mouse monoclonal IgG control rotated overnight at 4° C. Fresh protein A beads (Roche, Mannheim, Germany) were washed in advance with immunoprecipitation assay buffer containing 2% SDS and protease inhibitors ("Complete Mini-EDTA Free" protease inhibitor tablet, Roche, Mannheim, Germany) three times. Beads were incubated with sample mixtures and rotated for 2 hours at 4° C., washed three times, incubated with a solution containing loading buffer and immunoprecipitation assay buffer, and reduced at 99° C. for 5 minutes. Supernatants were separated by SDS-PAGE followed by Western blot using a standard method (Yu et al. *J Cancer*, 1:141-149, 2010).

Frozen and fixed liver tumor samples were acquired from the Cooperative Human Tissue Network (Charlottesville, Va.) (Yu et al. *J Cancer*, 1:141-149, 2010) and Western blots were performed.

Immunohistochemistry

Formalin-fixed and paraffin-embedded tissue sections were subjected to immunohistochemical staining using 6 μg/mL of YP7 following a previously published protocol (Man and Tavassoli, *Appl Immunohistochem* 4:139-141, 1996). Immunostaining was carried out as previously described with YP7 and an isotype control mouse IgG (Southern Biotech, Birmingham, Ala.). Immunostained sections were independently evaluated by two investigators.

Animal Testing

All mice were housed and treated under the protocol approved by the Institutional Animal Care and Use Committee at the National Institutes of Health (NIH). Two rounds of in vivo passaging were performed for the HepG2 cell line before animal testing. Ten million cells were suspended in 200 μl of PBS and inoculated subcutaneously into 4 to 6 week-old female BALB/c nu/nu nude mice (NCI-Frederick, Frederick, Md.). When the tumor volume reached approximately 100 mm³ ($V=ab^2/2$, where a and b represent tumor length and width, respectively), mice were intravenously injected with 5 mg/kg of YP7 twice a week for two and a half weeks.

Example 2

Monoclonal Antibodies that Bind with High Affinity to GPC3-Expressing Cells

This example describes the identification of high affinity, GPC3-specific monoclonal antibodies capable of detecting cancer cells with low level expression of GPC3.

Design of the Peptide as an Immunogen for Mouse Immunization

To design a peptide for immunization, the primary structure of the GPC3 protein was analyzed as a 3D structure is not available. The mature GPC3 protein on the cell surface is modified by heparan sulfate chains and attached to the cell membrane by a GPI anchor (FIG. 1A). The GPC3 gene is located on human X chromosome (Xq26) and transcribed and alternatively spliced into four mRNA isoforms (Ho and Kim, *Eur J Cancer* 47:333-338, 2011). All isoforms share the same C-terminal subunit while their N-terminal subunits are slightly different. Their distribution and functional significance have not been established. The most common isoform (Isoform 2, GenBank Accession Nos.: NP_004475 and JQ943686) encodes a 70 kDa core protein with 580 amino acids (Ho, *BioDrugs* 25:275-284, 2011; Ho and Kim, *Eur J Cancer* 47:333-338, 2011). Three variants have been identified in GenBank that encode alternatively spliced forms termed Isoform 1 (NP_001158089), Isoform 3 (NP_001158090) and Isoform 4 (NP_001158091).

The C-terminal subunit of GPC3 is approximately 30 kDa in length. Based on protein sequence using big-PI Predictor, serine 560 was predicted as a cleavage site for GPI (Allegretta and Filmus, *Anticancer Agents Med Chem* 11:543-548, 2011). A 50-mer peptide (residues 511-560) corresponding to the C-terminal end of cell-surface GPC3 was synthesized, allowing for recognition of each isoform. An additional cysteine residue was introduced to the N-terminus of the peptide. Therefore, mAbs raised against this peptide bind the C-terminal end of membrane-bound GPC3.

Screening of Monoclonal Antibodies to Cell Surface-Associated GPC3

Five BALB/c mice were immunized three times and boosted with peptide-KLH conjugate. Serum antibody titer to native conformation of GPC3 on the cell surface was measured by flow cytometry using GPC3-expressing cells as described in Example 1. Antibody titers for all mice were >10,000 after three immunizations, observed as non-overlapped stained cell peaks at a 1:10,000 dilution of sera along with peaks of non-stained cells. Spleen cell fusions were conducted with the two best mice.

To perform primary screening of ten 96-well plates of mAbs that recognize cell surface-associated GPC3 protein, a flow cytometry-based assay was developed in which a mixture of GPC3-negative cells (A431) and GPC3-positive cells (G1 or A431/G1, A431 stably transfected with GPC3) were used as the antigen to be tested for each supernatant sample (FIG. 1B). The use of this rapid screening method made it possible to screen 960 clones on the Guava EasyCyte flow cytometer within a 24-hour period. Clones with binding ratios (G1/A431) of 15 or more were selected for flow cytometry analysis using HepG2 cells. Twelve clones were subcloned by limited dilution. Among them, five (YP6, YP7, YP8, YP9 and YP9.1) were recovered and isotyped as IgG1 (γ1·κ). mAbs with the highest binding signals for the peptide in a standard ELISA have very weak or no binding to cell-surface associated GPC3. Taken together, the new method successfully isolated mAbs with high binding affinity for cell surface GPC3.

Affinity and Specificity of GPC3 mAbs on Cells

Figure 1C:
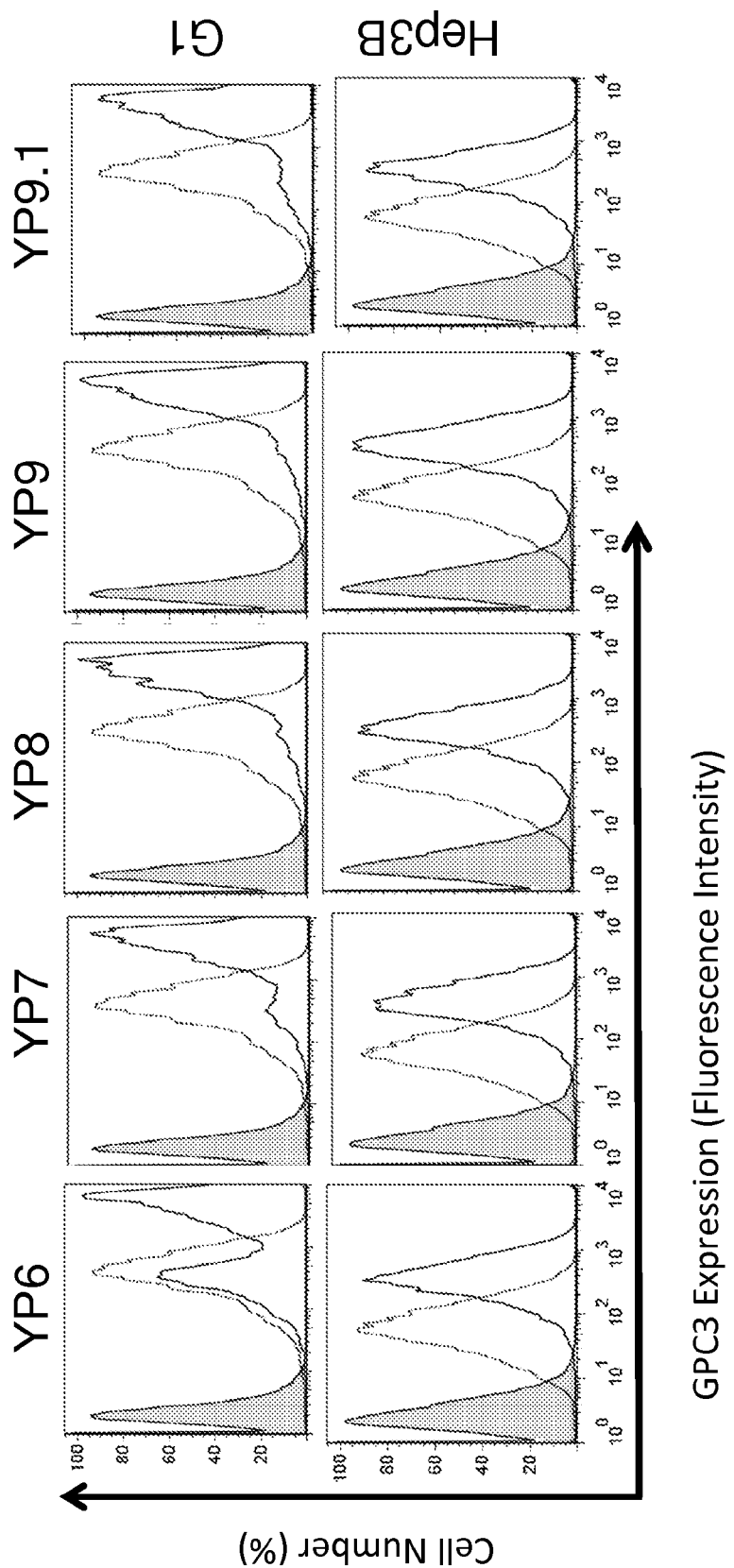
Figure 1D:
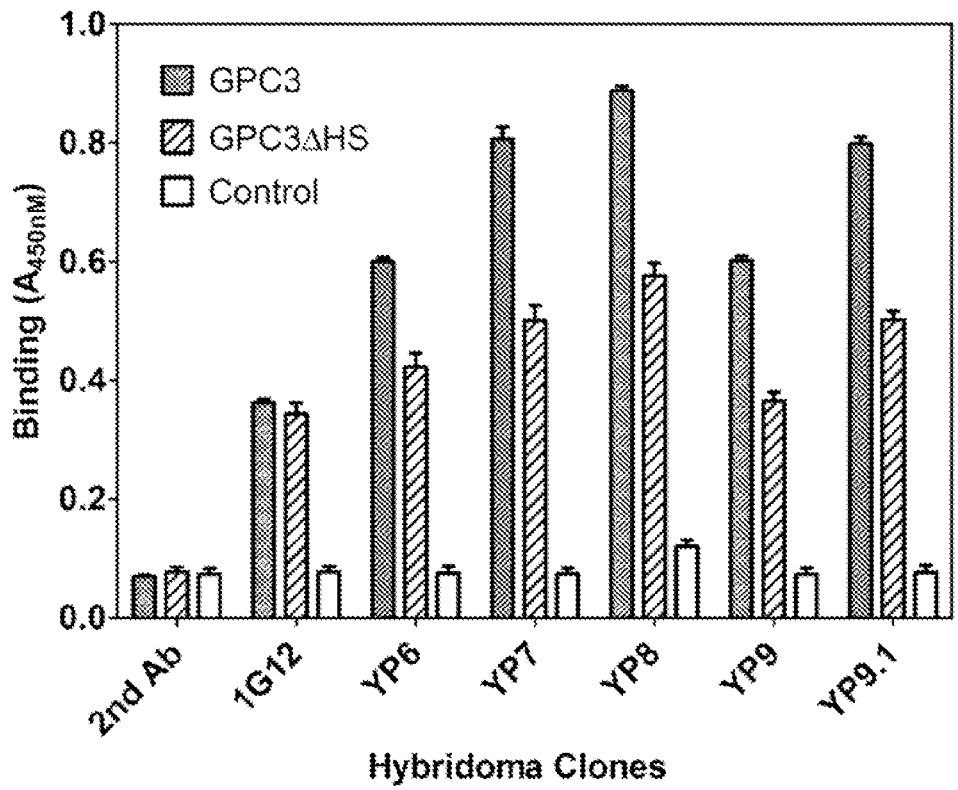

The five selected mAbs (YP6, YP7, YP8, YP9 and YP9.1) were analyzed for binding using four cell lines (A431, A431/G1, HepG2 and Hep3B) at 1 µg/ml. As shown in FIG. 1C, all bound to two GPC3-expressing cell lines tested (A431/G1 and Hep3B). Conversely, none bound to the GPC3-negative A431 cell line, suggesting that it is GPC3-specific and that binding for cell surface GPC3 was generally higher than 1G12 (Capurro and Filmus, *Cancer Res* 65:372, 2005). Reactivity with recombinant GPC3 and GPC3△HS (the mutant without heparan sulfate) proteins was then tested in an ELISA. Stronger binding signals were observed on wild-type GPC3 compared to GPC3△HS, the GPC3 core protein alone, while 1G12 bound both similarly (FIG. 1D). This result suggests that these new mAbs recognize the native form of GPC3 protein with heparan sulfate on the cell surface.

Figure 1E:
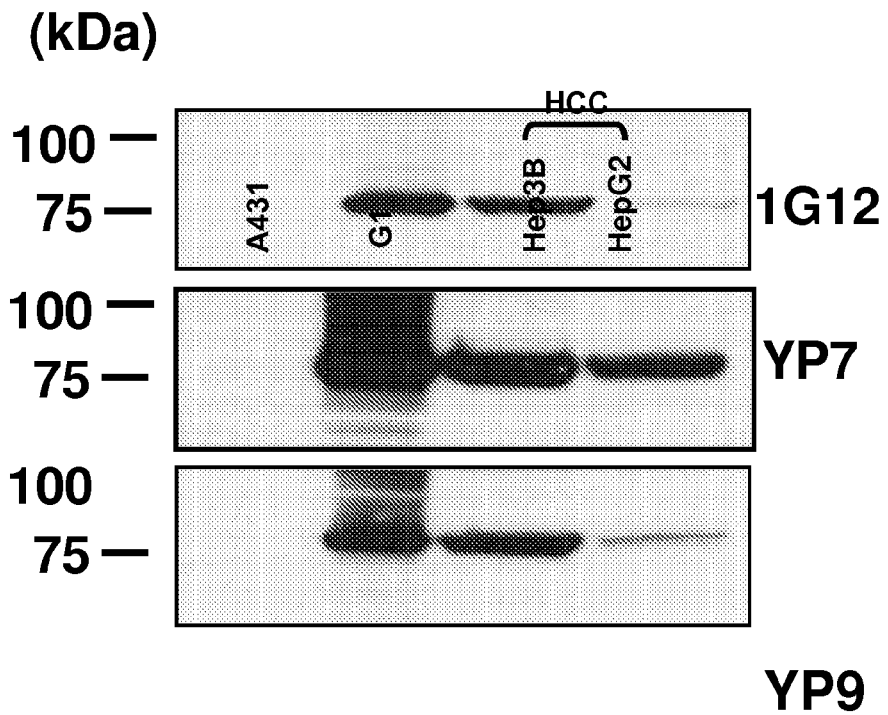

FIG. 1E shows a Western blot analysis indicating strong immunoreactivity of YP7 and YP9 with recombinant GPC3 proteins expressed in the A431/G1 cell line and no reactivity with other cellular proteins in the A431 cell line lysate. These mAbs also reacted with endogenous GPC3 proteins in HCC cell lines to various extents. Among those tested (including 1G12), YP7 showed strongest reactivity with GPC3 proteins in both HCC cell lines (HepG2 and Hep3B) and it was selected for further analyses using a panel of HCC and CCA cell lines.

Figure 2A:
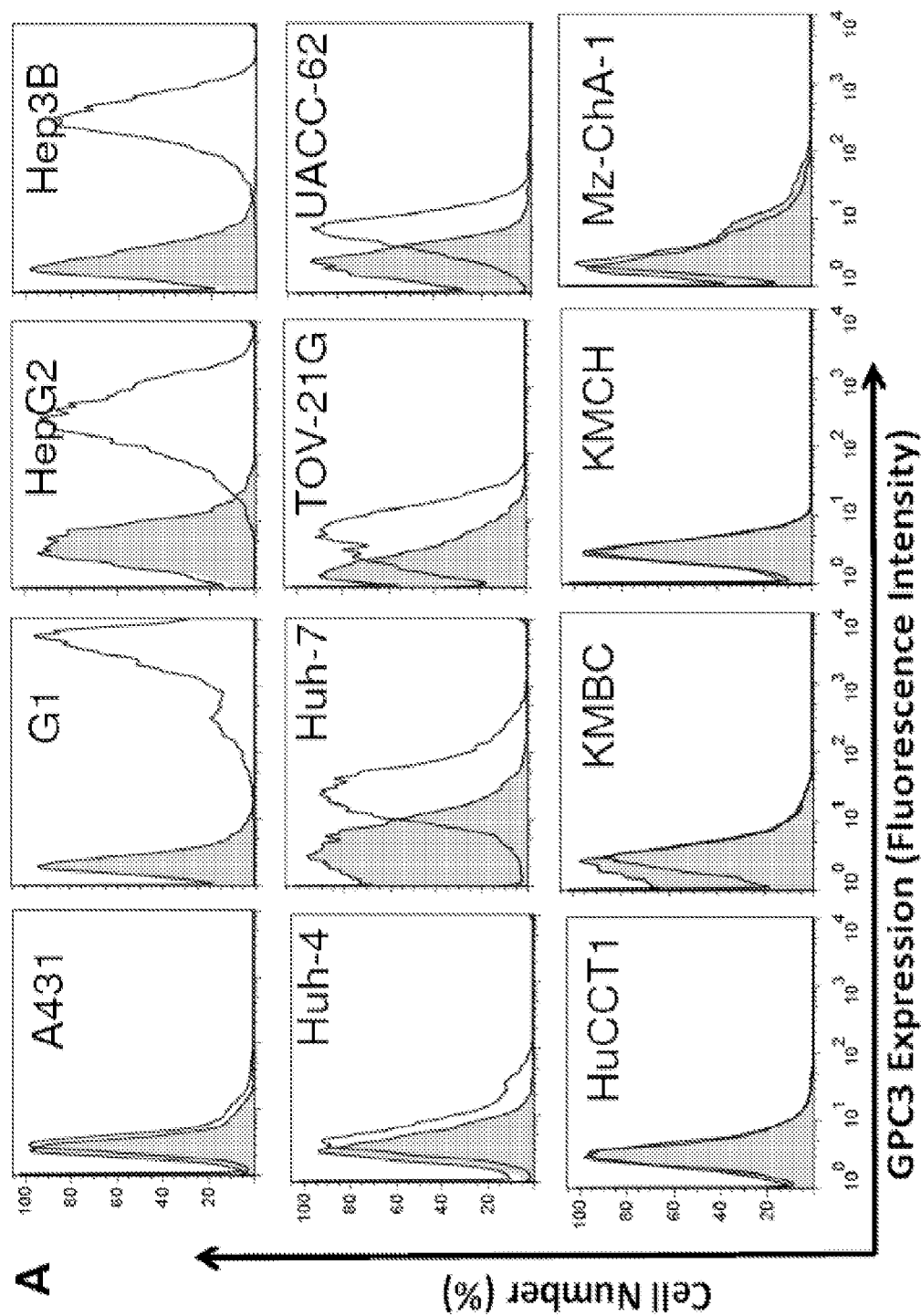
FIGS. 2A-2C: Characterization of YP7 binding properties.
Figure 2B:
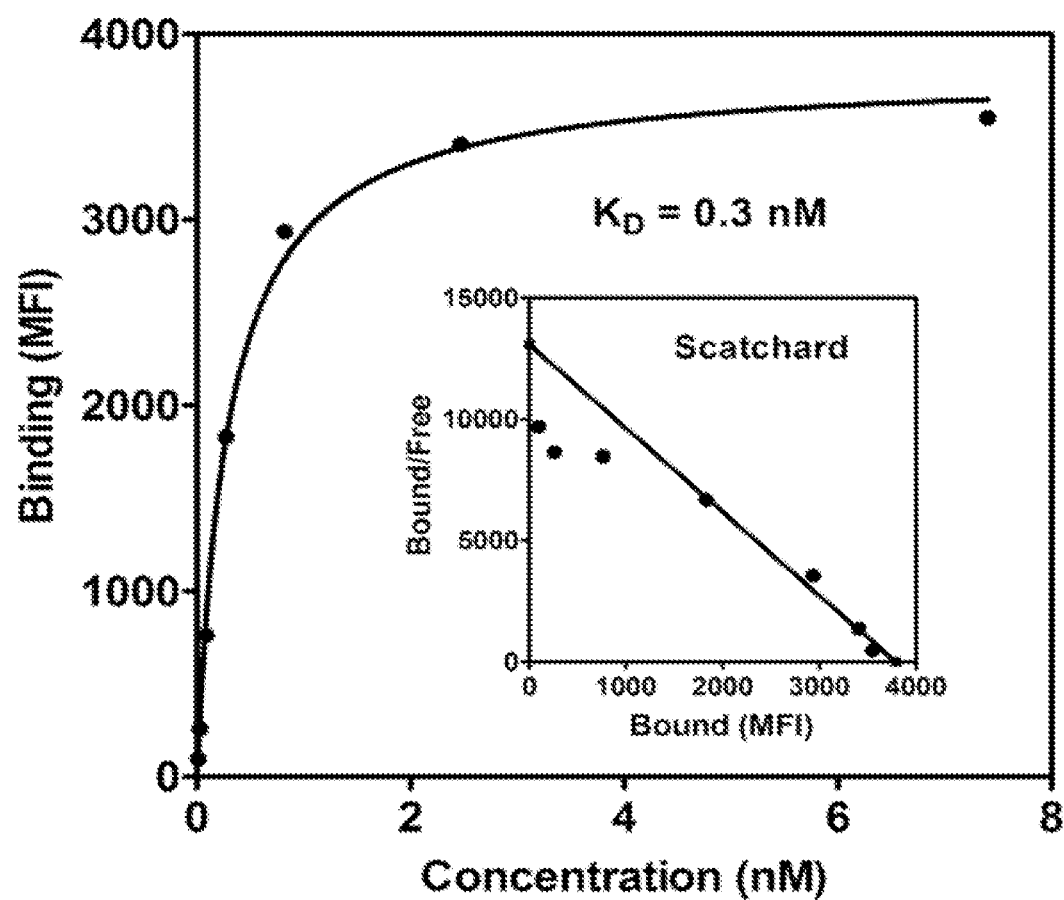
Figure 2C:
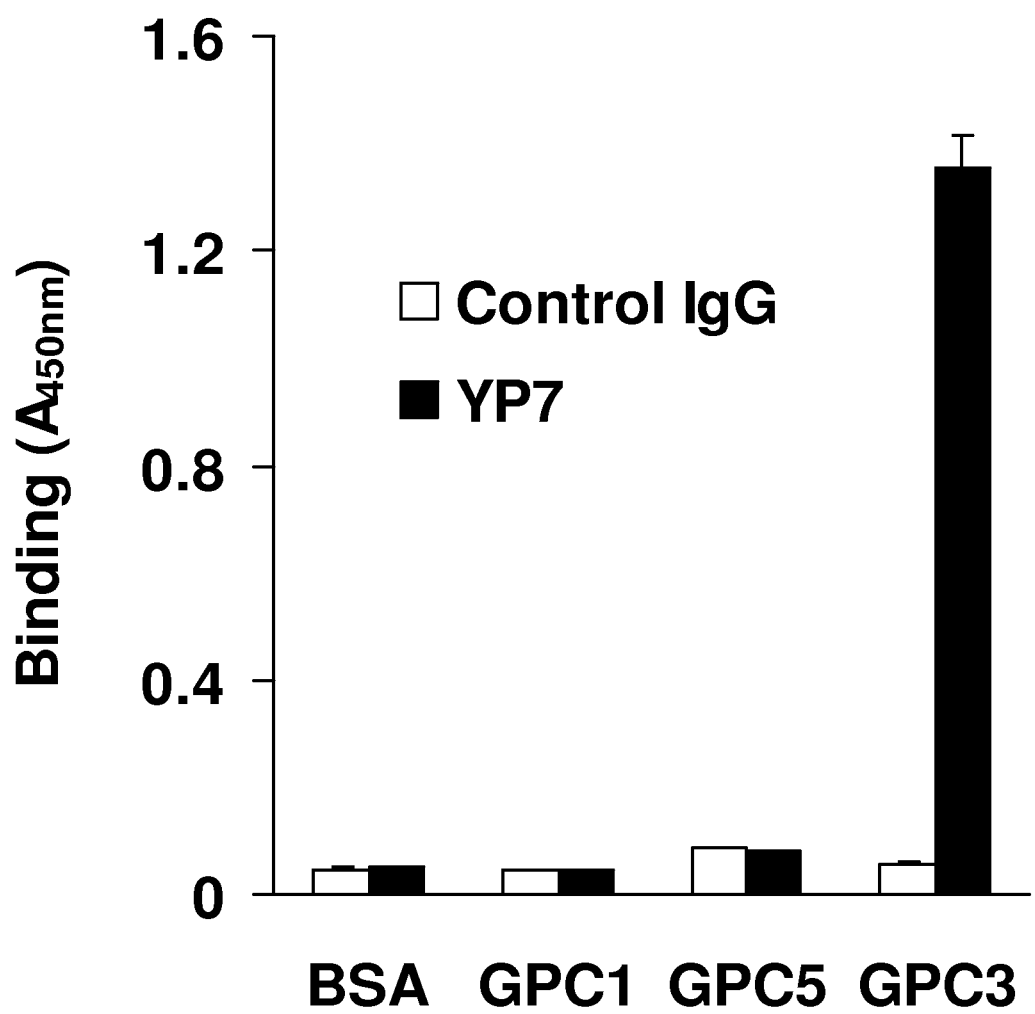

As shown in FIG. 2A, YP7 binds all HCC cell lines (HepG2, Hep3B, Huh4 and Huh7) in flow cytometry analysis. In contrast, YP7 did not react with the SK-Hep-1 cell line, originally reported as a HCC cell line but recently redefined as a non-HCC cell line (Yu et al. *J Cancer*, 1:141-149, 2010). FIG. 2A also shows that YP7 did not bind any of the CCA lines tested (HuCCT1, KMBC, KMCH and Mz-ChA-1). The high, subnanomolar binding affinity of YP7 ($K_D$=0.3 nM), was determined with the native form of GPC3 protein expressed on cells (FIG. 4B). Six glypicans (GPC1-6) have been identified in mammals (Ho and Kim, *Eur J Cancer* 47:333-338, 2011) sharing a characteristic structure. To evaluate whether YP7 is cross-reactive with other glypicans, it was tested with GPC1, GPC5 and GPC3 by ELISA. YP7 bound GPC3, but not GPC1 or GPC5 (FIG. 2C).

Figure 3B:
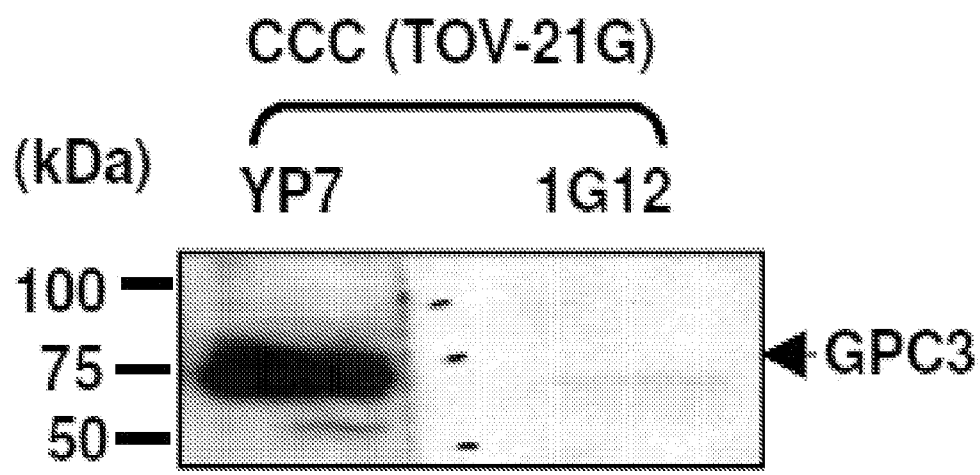

To evaluate the binding specificity of YP7 on liver cancer cells, immunoblotting was performed on a panel of HCC and CCA cells (FIG. 3A). YP7 showed strong GPC3 signals in five (HepG2, Hep3B, Huh1, Huh4 and Huh7) out of five (100%) HCC cell lines. SK-Hep-1 was GPC3-negative. No GPC3 protein was detected in any of the four CCA cell lines (KMCH, KMBC, Mz-ChA-1 and Oz). The reactivity profile of YP7 in Western blotting matched well with flow cytometry data (FIG. 2A), suggesting that YP7 specifically and equally detects endogenous GPC3 proteins. YP7 detected GPC3 expressed in TOV-21G, an ovarian clear cell carcinoma (CCC), while 1G12 did not clearly detect it (FIG. 3B). The difficulty of 1G12 has been previously reported and attributed to the very low expression level of GPC3 in TOV-21G cells (Suzuki et al., *Cancer Sci*, 102:1622-1629, 2011), thus depicting the usefulness of a high affinity mAb over 1G12. Together, these results demonstrate that YP7 has excellent binding affinity and specificity for the native form of GPC3 in HCC and other GPC3-expressing cancers (e.g., ovarian CCC), and is able to detect endogenous GPC3 at a very low expression level.

Detection of Soluble and Tissue GPC3 Proteins by YP7

Figure 3C:
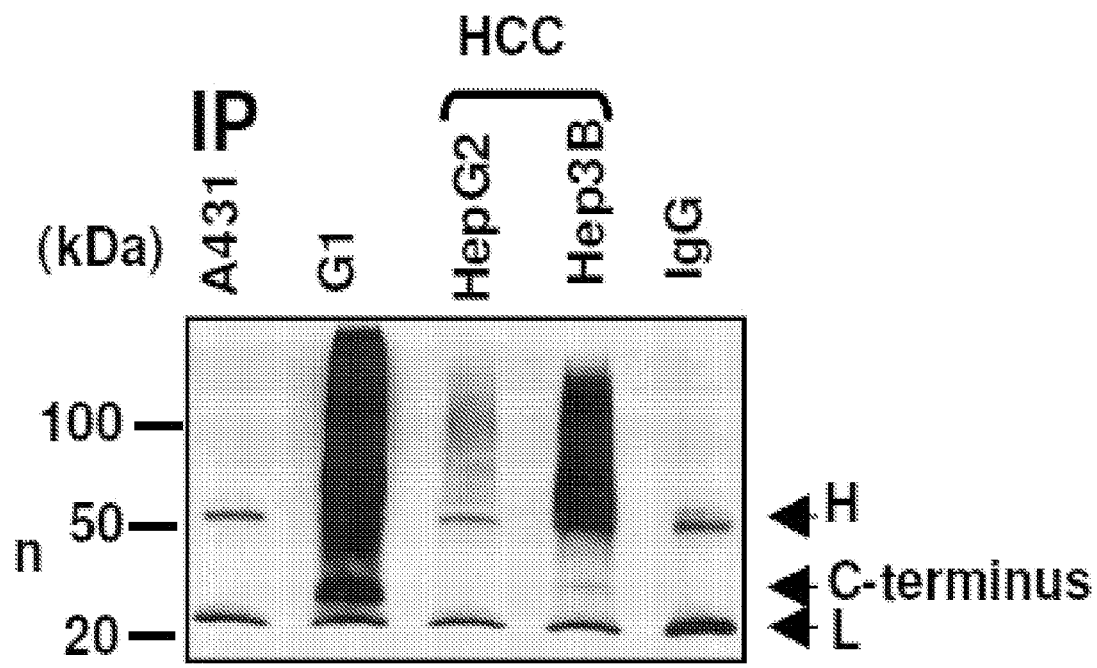

Previous studies showed the existence of soluble GPC3 protein in culture supernatant and patient serum (Capurro et al., *Gastroenterology* 125:89-97, 2003; Hippo et al., *Cancer Res*, 64:2418-2423, 2004). To investigate its diagnostic potential, YP7 was tested with soluble GPC3 protein in culture supernatants and patient samples. YP7 was used to pull down and probe soluble protein in culture supernatant from four cell lines (A431, A431/G1, HepG2, and Hep3B) (FIG. 3C). In A431/G1 and Hep3B pull down proteins, soluble GPC3 proteins were detected as smeared bands indicating a wide range of high molecular weight proteins corresponding to GPC3 proteins modified with varying numbers of heparan sulfate chains (Capurro et al., *Gastroenterology* 125:89-97, 2003; Capurro and Filmus, *Cancer Res* 65:372, 2005; Hippo et al., *Cancer Res*, 64:2418-2423, 2004). In addition to the GPC3 with heparan sulfate (smear), a 30 kDa band was detected in both culture supernatants, indicating that the C-terminal subunit alone was present in soluble GPC3 proteins.

Figure 3D:
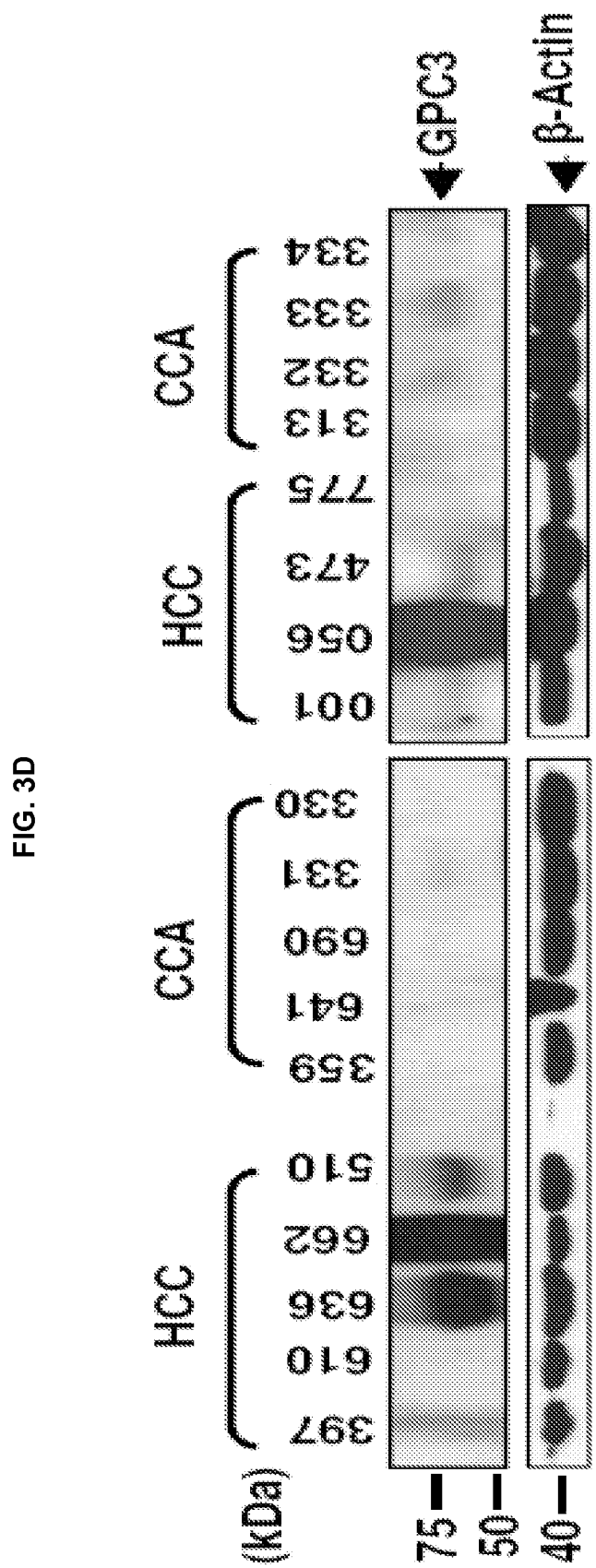

To evaluate YP7 for immunohistochemical applications, nine HCC and nine CCA patient tissues (Yu et al. *J Cancer*, 1:141-149, 2010) were used for Western blotting (FIG. 3D). High GPC3 protein expression was found in four out of nine (44%) HCC tissues as bands with an expected size of ~70 kD. GPC3 expression was not found in any of the nine (0%) CCA tissues.

Previous studies showed GPC3 expression in other cancers such as ovarian clear cell carcinoma, melanoma and non-small lung adenocarcinoma, although the expression profiling was generally not convincing (Ho and Kim, *Eur J Cancer* 47:333-338, 2011). YP7 was tested on all of the GPC3-positive cell lines in the NCI-60 set based on public microarray data (Table 5). It was determined that GPC3 protein expression in non-HCC cancer cells was consistent overall, however, cell surface expression in non-HCC cells was in general lower than that of HCC cells. YP7 bound UACC-62, a human melanoma cell line. GPC3 has been suggested as a potential therapeutic target for melanoma (Ho, *BioDrugs* 25:275-284, 2011; Ho and Kim, *Eur J Cancer* 47:333-338, 2011). However, a cell line model for GPC3-expressing melanoma has not been established and GPC3-targeted antibody therapy against melanoma has not been investigated likely due to the lack of a good cell model and a high-affinity anti-GPC3 mAb. These data indicate that UACC-62 could be a useful cell model to study GPC3 in melanoma and that YP is a suitable antibody for melanoma therapy.

TABLE 5

Characterization of GPC3 expression in non-HCC in the NCI-60 set

| Human cell line | Tumor type | Gene expression (microarray)* | Protein expression (immunoblotting)@ | Surface expression (flow cytometry)@ |
|---|---|---|---|---|
| NCI-H522 | Non-Small Cell Lung Cancer | +++ | +++ | +/− |
| MALME-3M | Melanoma | ++ | − | − |
| SK-MEL-5 | Melanoma | ++ | + | +/− |
| UACC-62 | Melanoma | ++ | +++ | + (histogram shown in FIG. 2A) |
| IGROV-1 | Ovarian cancer | ++ | ++ | − |
| OVCAR-8 | Ovarian cancer | ++ | + | − |
| NCI-ADR-RES | Ovarian cancer | ++ | +++ | +/− |

*Online at dtp.nci.nih.gov/mtweb;
@probed by YP7

Figure 3E:
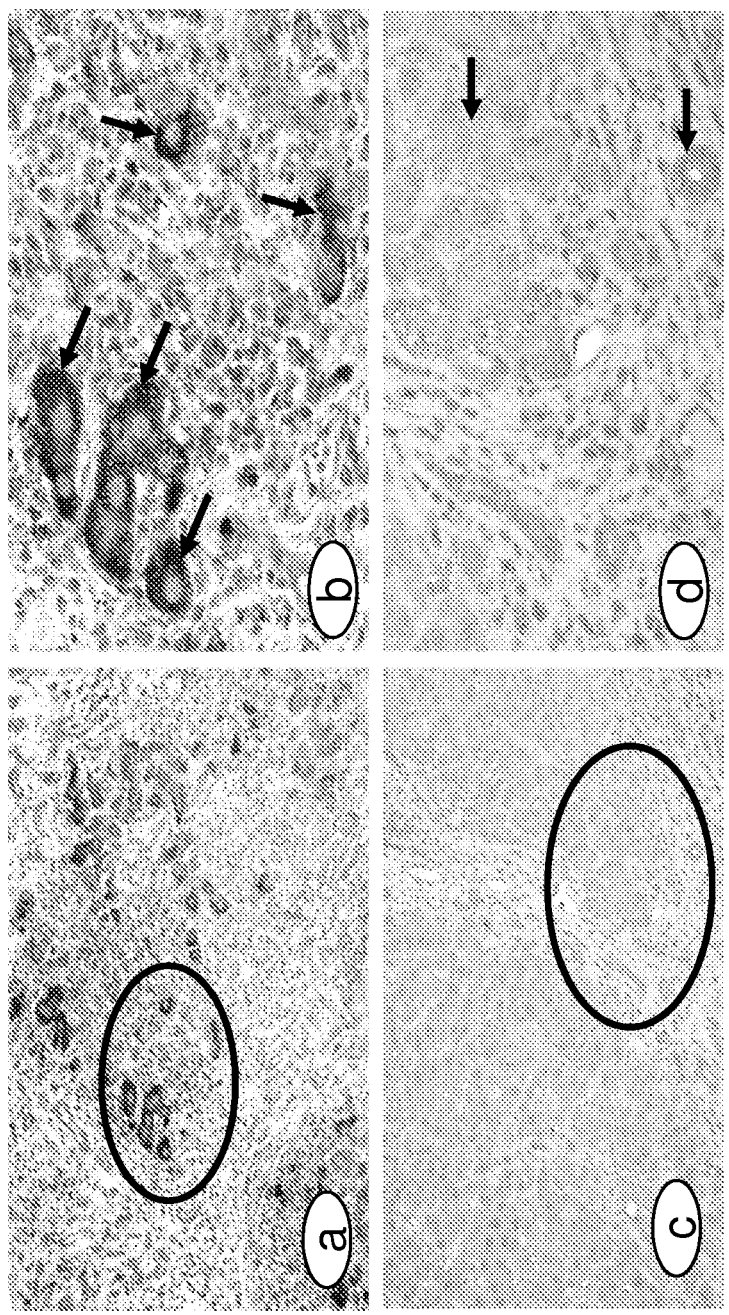

The binding of YP7 on human liver tissues was also examined by immunohistochemistry (IHC). As shown in FIG. 3E, invasive HCC showed distinct membrane or cytoplasmic expression of GPC3, whereas normal cells lacked distinct immunostaining (FIG. 3E). This observation supports the belief that GPC3 stained by YP7 is a suitable marker for IHC of liver tumors, particularly HCC. Together, Western blot analysis of HCC cells and tissues shows that YP7 is highly specific and sensitive for endogenous GPC3 proteins in both cell-surface form and soluble (shed) form, indicating that YP7 can be used as a diagnostic agent to evaluate serum GPC3 protein and GPC3 expression in HCC tissues.

Antitumor Activity of YP7

Figure 4A:
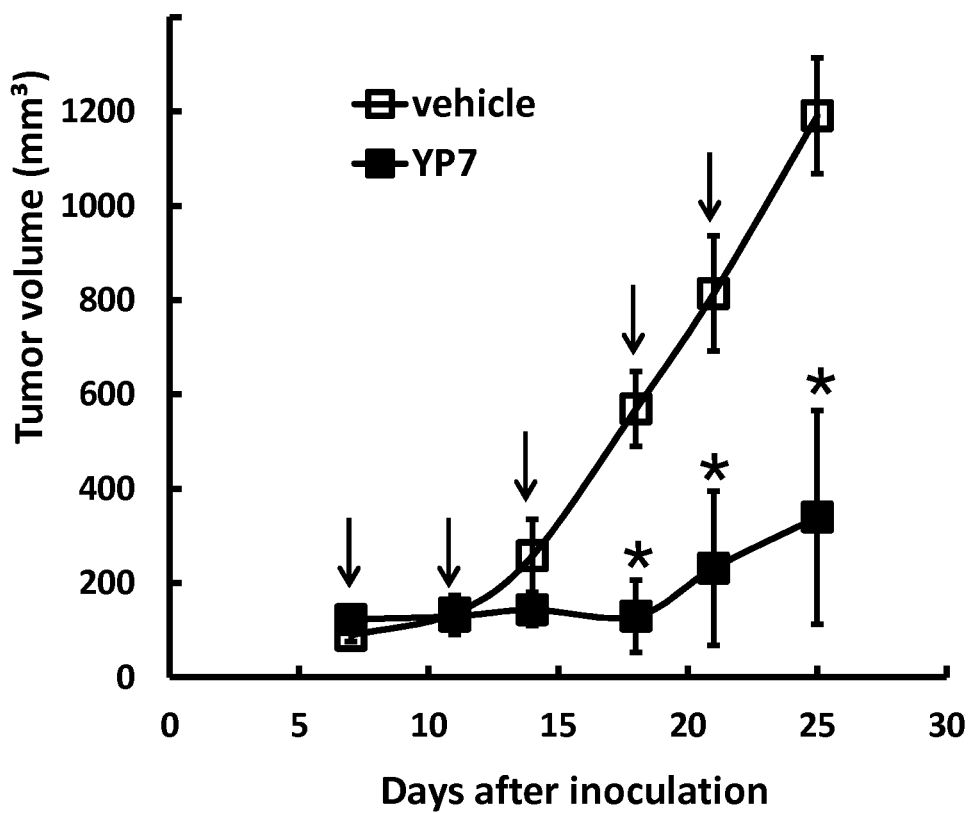
FIGS. 4A-4B: Anti-tumor activity of YP7 in the HCC xenograft model.
Figure 4B:
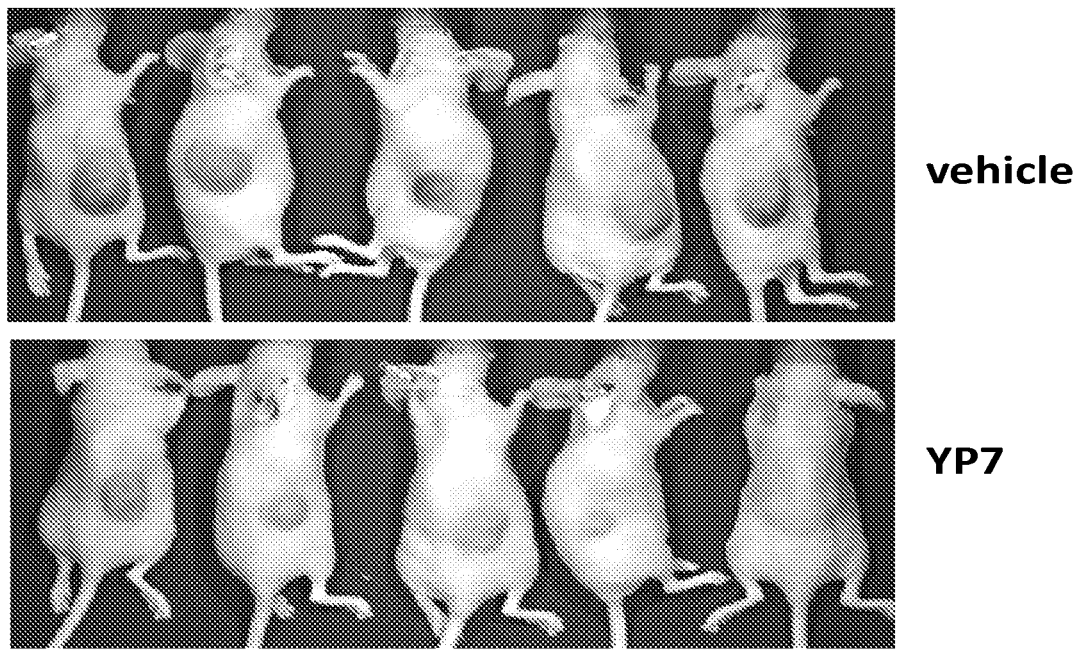
Figure 7B:
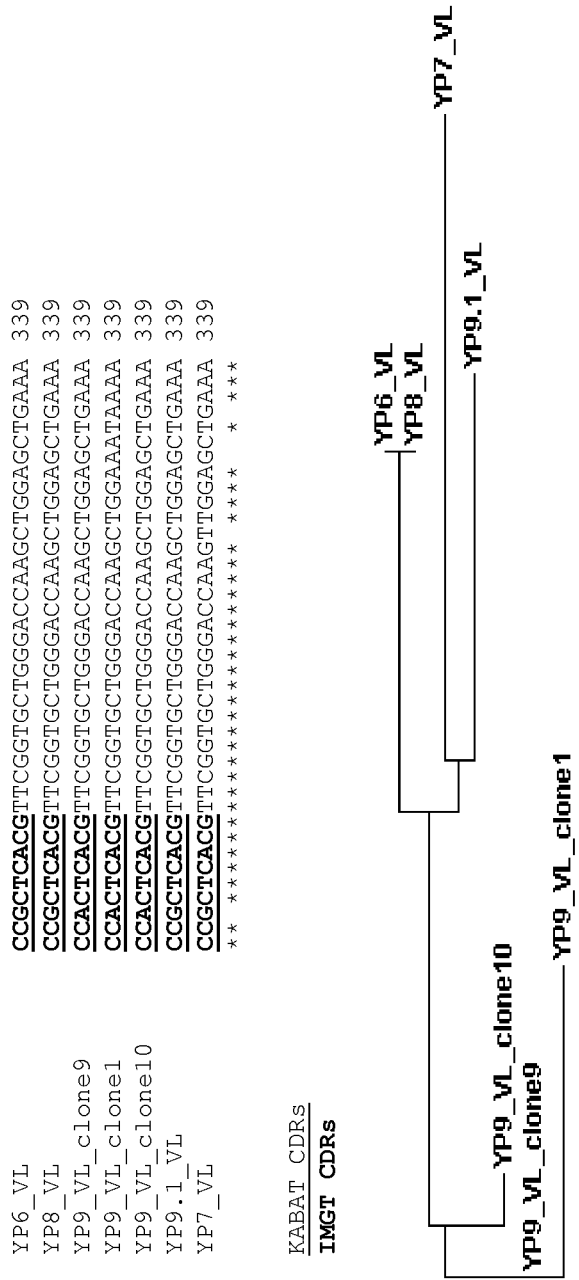

To explore YP7 as a potential cancer therapeutic, tumor growth inhibition was examined in HCC mice xenografts by using HepG2 cells to establish a model in nude mice (FIG. 4). When tumors reached an average volume of 100 mm³ on day 7, mice were administered 5 mg/kg of YP7 twice a week for two weeks. YP7 significantly inhibited the growth of the HepG2 tumors measured with nearly constant values of tumor volume during the two weeks, whereas tumors inoculated to non-treated mice continued to rapidly grow during this period. Therefore, YP7 exhibited strong antitumor activity against HepG2 xenografts in mice.

Discussion

As described herein, high-affinity mAbs to GPC3 were generated that are highly specific for GPC3-expressing tumor cells and tissues. YP7 detected low expression levels of GPC3 in HCC (e.g., HepG2 and Huh-4), ovarian clear cell carcinoma (e.g., TOV-21G), and melanoma cells (e.g., UACC-62). These results indicate that YP7 is a very promising candidate for cancer diagnostics and therapy targeting GPC3-expressing tumor cells.

Hybridoma technology for mAb production has been well established in the last 37 years (Köhler and Milstein, *Nature* 256:495-497, 1975), with eleven mAbs approved for cancer therapy (Shuptrine and Surana, *Semin Cancer Biol* 22:3-13, 2012) since the debut of Rituximab. However, a major obstacle in high-throughput development of therapeutic antibodies involves the feasibility of screening hundreds to thousands of hybridoma supernatants within a short time frame (24-48 hours) (Chiarella and Fazio, *Biotechnol Lett* 30:1303-10, 2008). While an ELISA is a suitable method for isolating mAbs specific for the peptide backbone or partially denatured protein antigen, it is not always practical for picking up mAbs that recognize the native form of antigens on cancer cells (Yokoyama et al., Current Protocols in Immunology, 2.5.1-2.5.25, 2006). To assess antibody reactivity with intact cell-associated antigens, a flow cytometry method is ideal, although traditional instruments are not designed for high-throughput assays. In light of this, a flow cytometer with an autosampler was used during initial screenings for the studies disclosed herein.

These new mAbs have significant potential for GPC3-expressing cancer treatment and diagnosis. Humanization (Getts et al., *MAbs* 2:682-694, 2010) and development of antibody toxin/drug conjugates (Pastan et al., *Nat Rev Cancer* 6:559-565, 2006) can develop them for cancer therapy. Immunoconjugates such as immunotoxins generally require very high-affinity Fv for toxin delivery because patients are treated with a much lower dose and fewer cycles than whole IgG antibodies alone to avoid toxin-mediated side effects (Pastan et al., *Nat Rev Cancer* 6:559-565, 2006). Furthermore, the antibody Fvs can be applied in chimeric antigen receptor (CAR)-T cell and antibody Fv-based gene therapy. The mAbs antibodies disclosed herein also have utility in diagnostics such as measurement of serum GPC3, IHC for cancer detection and treatment follow-up, in vivo tumor imaging, and isolation of circulating tumor cells.

Example 3

GPC3-Specific Immunotoxins

Four recombinant immunotoxins were generated using YP7, YP8, YP9 (clone 9) or YP9.1 scFv fused to *Pseudomonas* exotoxin fragment PE38 (SEQ ID NO: 1), following standard techniques. Briefly, in each immunotoxin construct, the antibody VH domain was fused to the VL domain using a linker sequence encoding the peptide $(Gly_4Ser)_3$ (amino acid residues 119-133 of SEQ ID NO: 28). The antibody VL domain was fused to PE38 using a short linker sequence (ASGG; amino acid residues 247-250 of SEQ ID NO: 28). FIGS. 9A-9D show the nucleotide and amino acid sequences of the YP7ScFv-PE38, YP8ScFv-PE38, YP9ScFv-PE38 and YP9.1ScFv-PE38 immunotoxins (also referred to as YP7IT, YP8IT, YP9IT and YP9.1IT), respectively. The nucleotide and amino acid sequences of the immunotoxins are set forth herein as SEQ ID NOs: 27, 28 and 30-35.

Figure 10:
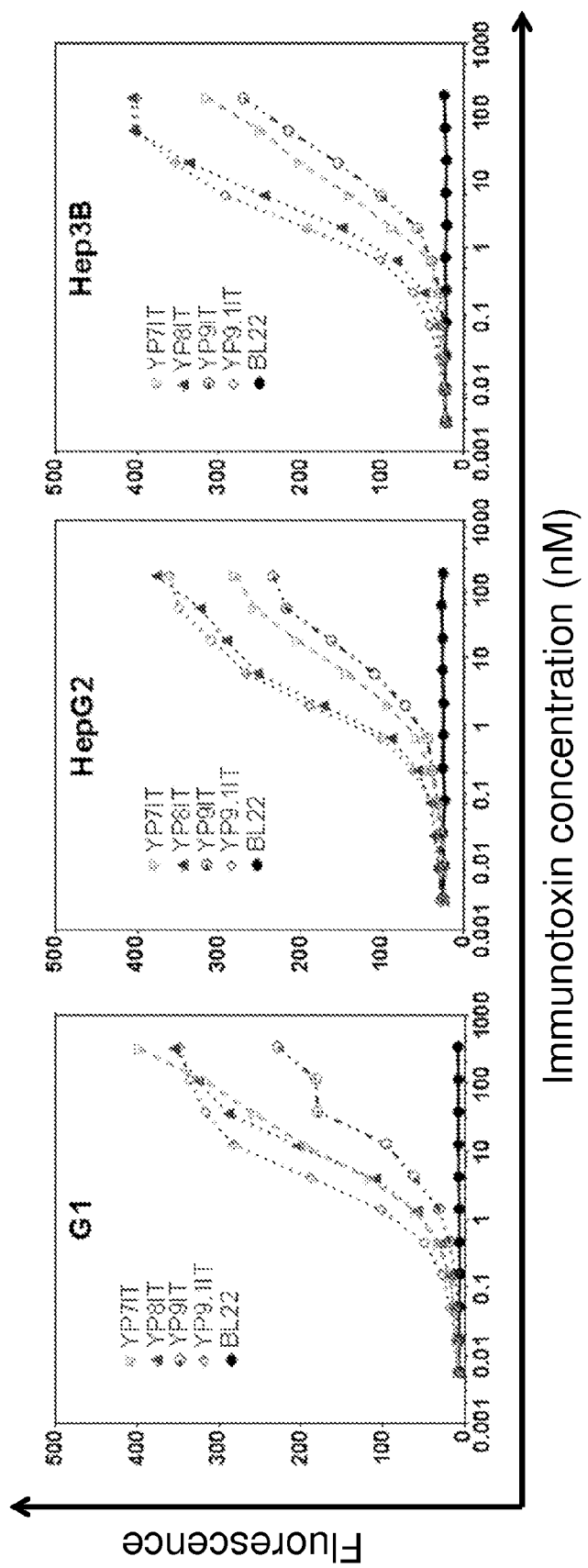
FIG. 10 is a series of graphs showing the binding affinity of anti-GPC3 immunotoxins (YP7IT, YP8IT, YP9IT and YP9.1IT) against GPC3-expressing cell lines G1 (left), HepG2 (middle) and Hep3B (right). Immunotoxin binding on these cell lines is indicated by fluorescence (geometric mean value) measured by flow cytometry.

Binding affinity of the immunotoxins for cells expressing GPC3 (G1, HepG2 and Hep3B cells) was evaluated by flow cytometry. Cells were harvested and resuspended in culture medium (DMEM supplemented with 10% FBS, 1% GIBCO® GlutaMAX™ and antibiotics). Cells were chilled on ice before incubation with immunotoxin serially diluted in culture medium. Next, cells were washed once with cold PBS, and incubated on ice for 60 minutes with rabbit anti PE38 antibody (Sigma-Aldrich) 1/200 diluted in culture medium. Then the cells were washed once with cold PBS, and incubated for 60 minutes on ice with RPE-goat anti rabbit antibody (Invitrogen P-2771MP) 1/200 diluted in culture medium. Cells were washed once in PBS again, and analysis was performed in a FACSCalibur machine (BD Biosciences). Data were acquired using Cell Quest software (BD Biosciences) and analyzed with FlowJo™. As shown in FIG. 10, all four immunotoxins exhibited very high binding affinity for GPC3-expressing cancer cells. For example, YP9.1ScFv-PE38 has picomolar binding affinity for Hep3B and HepG2 cells (Kd=40-50 μM). Binding affinity of each immunotoxin is summarized in Table 6 below.

Figure 11:
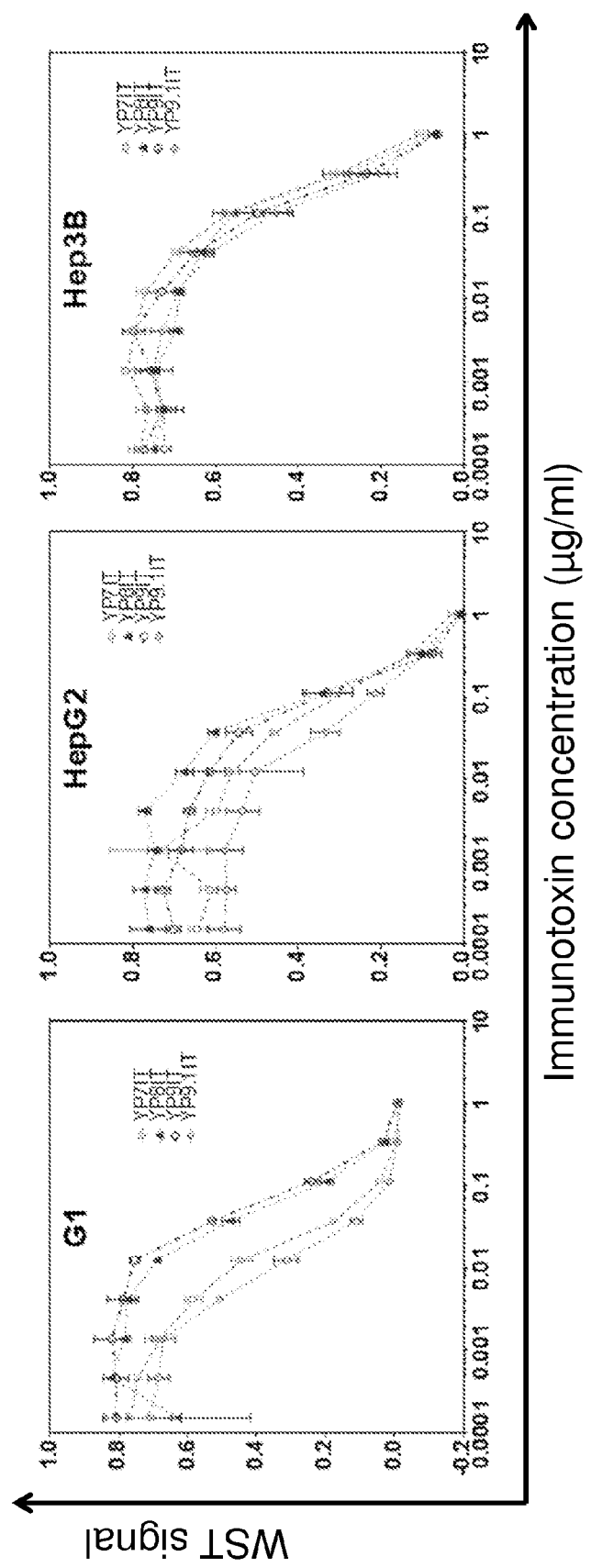
FIG. 11 is a series of graphs showing the cytotoxicity of anti-GPC3 immunotoxins (YP7IT, YP8IT, YP9IT and YP9.1IT) against GPC3-expressing cell lines G1 (left), HepG2 (middle) and Hep3B (right). Cell proliferation was assessed by WST-8 conversion. The absorbance of the sample at 450 nm was measured with a reference wavelength of 650 nm.

After confirming high binding affinity to GPC3-expressing cells, the immunotoxins were evaluated for cytotoxicity. Cells (G1, HepG2 and Hep3B cells) were plated in 96-well plates at a concentration of 2000 cells/180 μl/well in culture medium (DMEM supplemented with 10% FBS, 1% GIBCO® GlutaMAX™ and antibiotics). Immunotoxins were serially diluted in culture medium, and 20 μl of the resulting mixture was added to each well. Plates were incubated for 3 days at 37° C. Cell proliferation was assessed by WST-8 conversion using the Cell Counting Kit-8 (Dojindo Molecular Technologies, Gaithersburg, Md.). A volume of 10 μl of WST-8 (5 mm WST-8, 0.2 mm 1-methoxy-5-methylphenazinium methylsulfate, and 150 mm NaCl) was added to each well, and the incubation was carried out for 4 hours at 37° C. The absorbance of the sample at 450 nm was measured with a reference wavelength of 650 nm. As shown in FIG. 11, all immunotoxins significantly inhibited cell growth of all three GPC3-expressing cell lines. The inhibitory concentration 50 ($IC_{50}$) of each immunotoxin for G1, Hep3B and HepG2 cells is summarized in Table 6.

TABLE 6

Growth inhibition and cell binding affinity of anti-GPC3 immunotoxins

| | G1 | | Hep3B | | HepG2 | |
|---|---|---|---|---|---|---|
| | IC$_{50}$ (ng ml$^{-1}$) | Kd (nM) | IC$_{50}$ (ng ml$^{-1}$) | Kd (nM) | IC$_{50}$ (ng ml$^{-1}$) | Kd (nM) |
| YP7ScFv-PE38 | 15 | ≥10.53 | 304 | ≥8.65 | 92 | 0.10 |
| YP8ScFv-PE38 | 68 | 0.14 | 383 | 0.07 | 120 | ≥2.41 |
| YP9ScFv-PE38 | 73 | 0.22 | 233 | ≥15.53 | 122 | 0.15 |
| YP9.1ScFv-PE38 | 10 | 0.05 | 192 | 0.04 | 61 | 0.03 |

IC$_{50}$: growth inhibition of cells (WST assay)
Kd: binding affinity on cells (flow cytometry)

These data demonstrate that YP7, YP8, YP9 and YP9.1 immunotoxins all have very high binding affinity for GPC3-expressing cells and are capable of significantly inhibiting proliferation of GPC3-expressing cancer cells. In particular, the YP9.1scFv-PE38 immunotoxin exhibited the highest binding affinity and greatest inhibition of cancer cell growth.

Example 4

GPC3-Specific Monoclonal Antibodies for Detecting Cancer in a Subject or Confirming the Diagnosis of Cancer in a Subject This example describes the use of monoclonal antibodies that bind GPC3 for the detection of cancer in a subject. This example further describes the use of these antibodies to confirm the diagnosis of cancer in a subject.

A sample (such as a biopsy) is obtained from the patient diagnosed with, or suspected of having a GPC3-positive cancer (i.e., a cancer that expresses or overexpresses GPC3, such as HCC, melanoma, squamous cell carcinoma of the lung, or ovarian clear cell carcinoma). A sample taken from a patient that does not have cancer can be used as a control. Immuno-histochemistry (IHC) is performed to detect the presence of GPC3-expressing cells in the sample. IHC methods are well known in the art. For example, a GPC3-specific antibody conjugated to a fluorescent marker can be used to directly detect GPC3. An increase in fluorescence intensity of the patient sample, relative to the control sample, detects the presence of GPC3-expressing cells in the sample. Detection of GPC3-positive cells in the sample indicates the patient has a GPC3-positive cancer, or confirms diagnosis of cancer in the subject.

Example 5

GPC3-Specific Monoclonal Antibodies for the Treatment of Cancer

This example describes the use of GPC3-specific monoclonal antibodies for the treatment of cancers that express or overexpress GPC3, such as HCC, melanoma, squamous cell carcinoma of the lung, or ovarian clear cell carcinoma. Patients diagnosed with a GPC3-positive cancer can be treated according to standard procedures in the art.

In this example, patients diagnosed with a GPC3-positive cancer are administered an immunoconjugate comprising a GPC3-specific monoclonal antibody linked to *Pseudomonas* exotoxin (PE). Preparation of PE immunoconjugates has been previously described in the art (see, for example, U.S. Pat. No. 7,081,518 and U.S. Patent Application Publication No. 2005/0214304), and is described above in Example 3. In some patients, the immunoconjugate is administered by intravenous bolus injection every other day for a total of three to six doses. In other patients, the immunoconjugate is administered by continuous intravenous infusion over the course of ten days. The dose of immunoconjugate administered to a patient varies depending on the weight and gender of the patient, and mode and time course of administration. Following treatment, patients are evaluated for cancer progression (including tumor growth and metastasis) and other clinical signs of illness.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated monoclonal antibody that binds glypican-3 (GPC3), wherein:
   (i) the heavy chain of the antibody comprises a complementarity determining region (CDR) 1 set forth as SEQ ID NO: 38, a CDR2 set forth as SEQ ID NO: 39 and a CDR3 set forth as SEQ ID NO: 40, and the light chain of the antibody comprises a CDR1 set forth as SEQ ID NO: 44, a CDR2 set forth as amino acid residues 56-58 of SEQ ID NO: 14, and a CDR3 set forth as SEQ ID NO: 45; or
   (ii) the heavy chain of the antibody comprises a CDR1 set forth as SEQ ID NO: 41, a CDR2 set forth as SEQ ID NO: 42 and a CDR3 set forth as SEQ ID NO: 43, and the light chain of the antibody comprises a CDR1 set forth as SEQ ID NO: 46, a CDR2 set forth as SEQ ID NO: 47 and a CDR3 set forth as SEQ ID NO: 45.

2. The isolated monoclonal antibody of claim 1, wherein:
   (i) the heavy chain of the antibody comprises a CDR1, a CDR2 and a CDR3 respectively set forth as amino acid residues 26-33, 51-60 and 99-106 of SEQ ID NO: 12, and the light chain of the antibody comprises a CDR1, a CDR2 and a CDR3 respectively set forth as amino acid residues 27-38, 56-58 and 95-103 of SEQ ID NO: 14;
   (ii) the heavy chain of the antibody comprises a CDR1, a CDR2 and a CDR3 respectively set forth as amino acid residues 26-33, 51-60 and 99-106 of SEQ ID NO: 8, and the light chain of the antibody comprises a CDR1, a CDR2 and a CDR3 respectively set forth as amino acid residues 27-38, 56-58 and 95-103 of SEQ ID NO: 10;
   (iii) the heavy chain of the antibody comprises a CDR1, a CDR2 and a CDR3 respectively set forth as amino acid residues 26-33, 51-60 and 99-106 of SEQ ID NO: 16, and the light chain of the antibody comprises a CDR1, a CDR2 and a CDR3 respectively set forth as amino acid residues 27-38, 56-58 and 95-103 of SEQ ID NO: 18; or
   (iv) the heavy chain of the antibody comprises a CDR1, a CDR2 and a CDR3 respectively set forth as amino acid residues 26-33, 51-60 and 99-106 of SEQ ID NO: 20, and the light chain of the antibody comprises a CDR1, a CDR2 and a CDR3 respectively set forth as amino acid residues 27-38, 56-58 and 95-103 of SEQ ID NO: 22, a CDR1, a CDR2 and a CDR3 respectively set forth as amino acid residues 27-38, 56-58 and 95-103 of SEQ ID NO: 24 or a CDR1, a CDR2 and a CDR3 respectively set forth as amino acid residues 27-38, 56-58 and 95-103 of SEQ ID NO: 26.

3. The isolated monoclonal antibody of claim 1, wherein:
(i) the heavy chain of the antibody comprises a CDR1, a CDR2 and a CDR3 respectively set forth as amino acid residues 31-35, 50-68 and 101-106 of SEQ ID NO: 12 and the light chain of the antibody comprises a CDR1, a CDR2 and a CDR3 respectively set forth as amino acid residues 24-40, 56-62 and 95-103 of SEQ ID NO: 14;
(ii) the heavy chain of the antibody comprises a CDR1, a CDR2 and a CDR3 respectively set forth as amino acid residues 31-35, 50-68 and 101-106 of SEQ ID NO: 8 and the light chain of the antibody comprises a CDR1, a CDR2 and a CDR3 respectively set forth as amino acid residues 24-40, 56-62 and 95-103 of SEQ ID NO: 10;
(iii) the heavy chain of the antibody comprises a CDR1, a CDR2 and a CDR3 respectively set forth as amino acid residues 31-35, 50-68 and 101-106 of SEQ ID NO: 16 and the light chain of the antibody comprises a CDR1, a CDR2 and a CDR3 respectively set forth as amino acid residues 24-40, 56-62 and 95-103 of SEQ ID NO: 18; or
(iv) the heavy chain of the antibody comprises a CDR1, a CDR2 and a CDR3 respectively set forth as amino acid residues 31-35, 50-68 and 101-106 of SEQ ID NO: 20 and the light chain of the antibody comprises a CDR1, a CDR2 and a CDR3 respectively set forth as amino acid residues 24-40, 56-62 and 95-103 of SEQ ID NO: 22, a CDR1, a CDR2 and a CDR3 respectively set forth as amino acid residues 24-40, 56-62 and 95-103 of SEQ ID NO: 24 or a CDR1, a CDR2 and a CDR3 respectively set forth as amino acid residues 24-40, 56-62 and 95-103 of SEQ ID NO: 26.

4. The isolated monoclonal antibody of claim 1, wherein:
(i) the amino acid sequence of the heavy chain is at least 90% or at least 95% identical to SEQ ID NO: 12; and the amino acid sequence of the light chain is at least 90% or at least 95% identical to SEQ ID NO: 14;
(ii) the amino acid sequence of the heavy chain is at least 90% or at least 95% identical to SEQ ID NO: 8; and the amino acid sequence of the light chain is at least 90% or at least 95% identical to SEQ ID NO: 10;
(iii) the amino acid sequence of the heavy chain is at least 90% or at least 95% identical to SEQ ID NO: 16; and the amino acid sequence of the light chain is at least 90% or at least 95% identical to SEQ ID NO: 18; or
(iv) the amino acid sequence of the heavy chain is at least 90% or at least 95% identical to SEQ ID NO: 20; and the amino acid sequence of the light chain is at least 90% or at least 95% identical to SEQ ID NO: 22, 24 or 26.

5. The isolated monoclonal antibody of claim 1, wherein:
(i) the heavy chain of the antibody comprises SEQ ID NO: 12 and the light chain of the antibody comprises SEQ ID NO: 14;
(ii) the heavy chain of the antibody comprises SEQ ID NO: 8 and the light chain of the antibody comprises SEQ ID NO: 10;
(iii) the heavy chain of the antibody comprises SEQ ID NO: 16 or SEQ ID NO: 37 and the light chain of the antibody comprises SEQ ID NO: 18; or
(iv) the heavy chain of the antibody comprises SEQ ID NO: 20 and the light chain of the antibody comprises SEQ ID NO: 22, 24 or 26.

6. An isolated monoclonal antibody that binds glypican-3 (GPC3), wherein the antibody comprises:
(i) a variable heavy (VH) domain comprising the amino acid sequence of SEQ ID NO: 12, SEQ ID NO: 8, SEQ ID NO: 16, SEQ ID NO: 37 or SEQ ID NO: 20; and
(ii) a variable light (VL) domain comprising the amino acid sequence of SEQ ID NO: 14, SEQ ID NO: 10, SEQ ID NO: 18, SEQ ID NO: 22, SEQ ID NO: 24 or SEQ ID NO: 26.

7. The isolated monoclonal antibody of claim 1, wherein the antibody is a Fab fragment, a Fab' fragment, a F(ab)'$_2$ fragment, a single chain variable fragment (scFv), or a disulfide stabilized variable fragment (dsFv).

8. The isolated monoclonal antibody of claim 1, wherein the antibody is an IgG.

9. The isolated monoclonal antibody of claim 1, wherein the antibody is labeled.

10. The isolated monoclonal antibody of claim 9, wherein the label is a fluorescent, enzymatic, or radioactive label.

11. The isolated monoclonal antibody of claim 1, wherein the monoclonal antibody is a humanized monoclonal antibody.

12. A composition comprising a therapeutically effective amount of the antibody of claim 1 in a pharmaceutically acceptable carrier.

13. An isolated immunoconjugate comprising the monoclonal antibody of claim 1 and an effector molecule.

14. The isolated immunoconjugate of claim 13, wherein the effector molecule is a toxin.

15. The isolated immunoconjugate of claim 14, wherein the toxin is *Pseudomonas* exotoxin or a variant thereof.

16. The isolated immunoconjugate of claim 15, wherein the toxin is PE38 comprising the amino acid sequence of SEQ ID NO: 1.

17. The isolated immunoconjugate of claim 13, comprising the amino acid sequence of residues 2-597 of SEQ ID NO: 35, residues 2-597 of SEQ ID NO: 28, residues 2-597 of SEQ ID NO: 31, or residues 2-597 of SEQ ID NO: 33.

18. The isolated immunoconjugate of claim 13, wherein the effector molecule is a detectable label.

19. A composition comprising a therapeutically effective amount of the isolated immunoconjugate of claim 13 in a pharmaceutically acceptable carrier.

20. A method of treating a liver cancer in a subject, comprising selecting a subject with a liver cancer that expresses glypican-3 (GPC3) and administering to the subject a therapeutically effective amount of the composition of claim 12, thereby treating the liver cancer in the subject.

21. A method of inhibiting liver tumor growth or metastasis, comprising selecting a subject with a liver cancer that expresses glypican-3 (GPC3) and administering to the subject a therapeutically effective amount of the composition of claim 12, thereby inhibiting liver tumor growth or metastasis.

22. A method of detecting glypican-3 (GPC3) in a tissue sample, comprising:
contacting the tissue sample with the monoclonal antibody of claim 1; and
detecting binding of the antibody to the sample,
wherein an increase in binding of the antibody to the sample as compared to binding of the antibody to a control sample detects GPC3 in the tissue sample.

23. The method of claim 22, wherein the monoclonal antibody is directly labeled.

24. The method of claim 22, further comprising:
contacting a second antibody that specifically binds the monoclonal antibody with the sample, and
detecting the binding of the second antibody,
wherein an increase in binding of the second antibody to the sample as compared to binding of the second antibody to a control sample detects GPC3 in the tissue sample.

25. The method of claim 22, wherein the tissue sample comprises a hepatocellular carcinoma (HCC), melanoma, squamous cell carcinoma of the lung or ovarian clear cell carcinoma tumor biopsy.

26. An isolated nucleic acid molecule encoding the monoclonal antibody of claim 1.

27. The isolated nucleic acid molecule of claim 26, wherein:
   (i) the nucleotide sequence encoding the heavy chain of the monoclonal antibody comprises SEQ ID NO: 11 and the nucleotide sequence encoding the light chain of the monoclonal antibody comprises SEQ ID NO: 13;
   (ii) the nucleotide sequence encoding the heavy chain of the monoclonal antibody comprises SEQ ID NO: 7 and the nucleotide sequence encoding the light chain of the monoclonal antibody comprises SEQ ID NO: 9;
   (iii) the nucleotide sequence encoding the heavy chain of the monoclonal antibody comprises SEQ ID NO: 15 or SEQ ID NO: 36 and the nucleotide sequence encoding the light chain of the monoclonal antibody comprises SEQ ID NO: 17; or
   (iv) the nucleotide sequence encoding the heavy chain of the monoclonal antibody comprises SEQ ID NO: 19 and the nucleotide sequence encoding the light chain of the monoclonal antibody comprises SEQ ID NO: 21, SEQ ID NO: 23 or SEQ ID NO: 25.

28. An expression vector comprising the isolated nucleic acid molecule of claim 26.

29. An isolated host cell transformed with the expression vector of claim 28.

30. A method of treating a liver cancer in a subject, comprising selecting a subject with a liver cancer that expresses glypican-3 (GPC3) and administering to the subject a therapeutically effective amount of the composition of claim 19, thereby treating the liver cancer in the subject.

31. A method of inhibiting liver tumor growth or metastasis, comprising selecting a subject with a liver cancer that expresses glypican-3 (GPC3) and administering to the subject a therapeutically effective amount of the composition of claim 19, thereby inhibiting liver tumor growth or metastasis.

32. A chimeric antigen receptor (CAR), comprising the monoclonal antibody of claim 1.

33. A bispecific antibody, comprising the monoclonal antibody of claim 1.

\* \* \* \* \*

SEQUENCE LISTING

```
<160> NUMBER OF SEQ ID NOS: 47

<210> SEQ ID NO 1
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 1

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30
```

Glu Gln Cys Gly Tyr Pro Val Gln Arg Leu Val Ala Leu Tyr Leu Ala
            35                  40                  45

Ala Arg Leu Ser Trp Asn Gln Val Asp Gln Val Ile Arg Asn Ala Leu
 50                  55                  60

Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Gly Asp Val Ser Phe Ser Thr Arg
130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
            195                 200                 205

Leu Ala Tyr Gly Tyr Ala Gln Asp Gln Glu Pro Asp Ala Arg Gly Arg
            210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
            275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345

<210> SEQ ID NO 2
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 2

Arg His Arg Gln Pro Arg Gly Trp Glu Gln Leu Pro Thr Gly Ala Glu
 1               5                  10                  15

Phe Leu Gly Asp Gly Gly Asp Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

```
Arg Gly Tyr Val Phe Val Gly Tyr His Gly Thr Phe Leu Glu Ala Ala
            50                  55                  60

Gln Ser Ile Val Phe Gly Val Arg Ala Arg Ser Gln Asp Leu Asp
 65                  70                  75                  80

Ala Ile Trp Arg Gly Phe Tyr Ile Ala Gly Asp Pro Ala Leu Ala Tyr
                    85                  90                  95

Gly Tyr Ala Gln Asp Gln Glu Pro Asp Ala Arg Gly Arg Ile Arg Asn
               100                 105                 110

Gly Ala Leu Leu Arg Val Tyr Val Pro Arg Ser Ser Leu Pro Gly Phe
               115                 120                 125

Tyr Arg Thr Ser Leu Thr Leu Ala Ala Pro Glu Ala Ala Gly Glu Val
           130                 135                 140

Glu Arg Leu Ile Gly His Pro Leu Pro Leu Arg Leu Asp Ala Ile Thr
145                 150                 155                 160

Gly Pro Glu Glu Glu Gly Gly Arg Leu Glu Thr Ile Leu Gly Trp Pro
                   165                 170                 175

Leu Ala Glu Arg Thr Val Val Ile Pro Ser Ala Ile Pro Thr Asp Pro
               180                 185                 190

Arg Asn Val Gly Gly Asp Leu Asp Pro Ser Ser Ile Pro Asp Lys Glu
               195                 200                 205

Gln Ala Ile Ser Ala Leu Pro Asp Tyr Ala Ser Gln Pro Gly Lys Pro
           210                 215                 220

Pro Arg Glu Asp Leu Lys
225                 230

<210> SEQ ID NO 3
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 3

Arg His Arg Gln Pro Arg Gly Trp Glu Gln Leu Pro Thr Gly Ala Glu
 1               5                  10                  15

Phe Leu Gly Asp Gly Gly Asp Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Gly Gly Tyr Val Phe Val Gly Tyr His Gly Thr Phe Leu Glu Ala Ala
        50                  55                  60

Gln Ser Ile Val Phe Gly Val Arg Ala Arg Ser Gln Asp Leu Asp
 65                  70                  75                  80

Ala Ile Trp Ala Gly Phe Tyr Ile Ala Gly Asp Pro Ala Leu Ala Tyr
                    85                  90                  95

Gly Tyr Ala Gln Asp Gln Glu Pro Asp Ala Ala Gly Arg Ile Arg Asn
               100                 105                 110

Gly Ala Leu Leu Arg Val Tyr Val Pro Arg Ser Ser Leu Pro Gly Phe
               115                 120                 125

Tyr Ala Thr Ser Leu Thr Leu Ala Ala Pro Glu Ala Ala Gly Glu Val
           130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                   165                 170                 175
```

```
Leu Ala Glu Arg Thr Val Val Ile Pro Ser Ala Ile Pro Thr Asp Pro
            180                 185                 190

Arg Asn Val Gly Gly Asp Leu Asp Pro Ser Ser Ile Pro Asp Ser Glu
        195                 200                 205

Gln Ala Ile Ser Ala Leu Pro Asp Tyr Ala Ser Gln Pro Gly Lys Pro
    210                 215                 220

Pro Arg Glu Asp Leu Lys
225                 230

<210> SEQ ID NO 4
<211> LENGTH: 230
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (23)..(23)
<223> OTHER INFORMATION: Xaa = Gly, Ala or Ser
<220> FEATURE:
<221> NAME/KEY: MISC_FEATURE
<222> LOCATION: (49)..(49)
<223> OTHER INFORMATION: Xaa = Gly, Ala or Ser
<220> FEATURE:
<221> NAME/KEY: MISC_FEATURE
<222> LOCATION: (84)..(84)
<223> OTHER INFORMATION: Xaa = Gly, Ala or Ser
<220> FEATURE:
<221> NAME/KEY: MISC_FEATURE
<222> LOCATION: (107)..(107)
<223> OTHER INFORMATION: Xaa = Gly, Ala or Ser
<220> FEATURE:
<221> NAME/KEY: MISC_FEATURE
<222> LOCATION: (130)..(130)
<223> OTHER INFORMATION: Xaa = Gly, Ala or Ser
<220> FEATURE:
<221> NAME/KEY: MISC_FEATURE
<222> LOCATION: (165)..(165)
<223> OTHER INFORMATION: Xaa = Gly, Ala or Ser
<220> FEATURE:
<221> NAME/KEY: MISC_FEATURE
<222> LOCATION: (207)..(207)
<223> OTHER INFORMATION: Xaa = Gly, Ala or Ser
<220> FEATURE:
<221> NAME/KEY: MISC_FEATURE
<222> LOCATION: (209)..(209)
<223> OTHER INFORMATION: Xaa = Gly, Ala or Ser

<400> SEQUENCE: 4

Arg His Arg Gln Pro Arg Gly Trp Glu Gln Leu Pro Thr Gly Ala Glu
1               5                   10                  15

Phe Leu Gly Asp Gly Gly Xaa Val Ser Phe Ser Thr Arg Gly Thr Gln
            20                  25                  30

Asn Trp Thr Val Glu Arg Leu Leu Gln Ala His Arg Gln Leu Glu Glu
        35                  40                  45

Xaa Gly Tyr Val Phe Val Gly Tyr His Gly Thr Phe Leu Glu Ala Ala
    50                  55                  60

Gln Ser Ile Val Phe Gly Val Arg Ala Arg Ser Gln Asp Leu Asp
65                  70                  75                  80

Ala Ile Trp Xaa Gly Phe Tyr Ile Ala Gly Asp Pro Ala Leu Ala Tyr
            85                  90                  95

Gly Tyr Ala Gln Asp Gln Glu Pro Asp Ala Xaa Gly Arg Ile Arg Asn
            100                 105                 110

Gly Ala Leu Leu Arg Val Tyr Val Pro Arg Ser Ser Leu Pro Gly Phe
            115                 120                 125
```

```
Tyr Xaa Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Xaa Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
                180                 185                 190

Arg Asn Val Gly Gly Asp Leu Asp Pro Ser Ser Ile Pro Asp Xaa Glu
            195                 200                 205

Xaa Ala Ile Ser Ala Leu Pro Asp Tyr Ala Ser Gln Pro Gly Lys Pro
210                 215                 220

Pro Arg Glu Asp Leu Lys
225                 230

<210> SEQ ID NO 5
<211> LENGTH: 230
<212> TYPE: PRT
<213> ORGANISM: Artificial Sequence
<220> FEATURE:
<223> OTHER INFORMATION: Synthetic polypeptide

<400> SEQUENCE: 5

Arg His Arg Gln Pro Arg Gly Trp Glu Gln Leu Pro Thr Gly Ala Glu
1               5                   10                  15

Phe Leu Gly Asp Gly Gly Ala Val Ser Phe Ser Thr Arg Gly Thr Gln
                20                  25                  30

Asn Trp Thr Val Glu Arg Leu Leu Gln Ala His Arg Gln Leu Glu Glu
            35                  40                  45

Gly Gly Tyr Val Phe Val Gly Tyr His Gly Thr Phe Leu Glu Ala Ala
        50                  55                  60

Gln Ser Ile Val Phe Gly Gly Val Arg Ala Arg Ser Gln Asp Leu Asp
65                  70                  75                  80

Ala Ile Trp Ala Gly Phe Tyr Ile Ala Gly Asp Pro Ala Leu Ala Tyr
                85                  90                  95

Gly Tyr Ala Gln Asp Gln Glu Pro Asp Ala Ala Gly Arg Ile Arg Asn
            100                 105                 110

Gly Ala Leu Leu Arg Val Tyr Val Pro Arg Ser Ser Leu Pro Gly Phe
        115                 120                 125

Tyr Ala Thr Ser Leu Thr Leu Ala Ala Pro Glu Ala Ala Gly Glu Val
    130                 135                 140

Glu Arg Leu Ile Gly His Pro Leu Pro Leu Arg Leu Asp Ala Ile Thr
145                 150                 155                 160

Gly Pro Glu Glu Ser Gly Gly Arg Leu Glu Thr Ile Leu Gly Trp Pro
                165                 170                 175

Leu Ala Glu Arg Thr Val Val Ile Pro Ser Ala Ile Pro Thr Asp Pro
                180                 185                 190

Arg Asn Val Gly Gly Asp Leu Asp Pro Ser Ser Ile Pro Asp Ser Glu
            195                 200                 205

Ala Ala Ile Ser Ala Leu Pro Asp Tyr Ala Ser Gln Pro Gly Lys Pro
210                 215                 220

Pro Arg Glu Asp Leu Lys
225                 230

<210> SEQ ID NO 6
<211> LENGTH: 50
```

```
<212> TYPE: PRT
<213> ORGANISM: Artificial Sequence
<220> FEATURE:
<223> OTHER INFORMATION: Synthetic polypeptide

<400> SEQUENCE: 6

Asp Gly Met Ile Lys Val Lys Asn Gln Leu Arg Phe Leu Ala Glu Leu
1               5                   10                  15

Ala Tyr Asp Leu Asp Val Asp Asp Ala Pro Gly Asn Ser Gln Gln Ala
            20                  25                  30

Thr Pro Lys Asp Asn Glu Ile Ser Thr Phe His Asn Leu Gly Asn Val
        35                  40                  45

His Ser
    50

<210> SEQ ID NO 7
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 7
gaggtgcagc ttgttgagac tggtggagga atggtgcagc ctgaagggtc attgaaactc    60
tcatgtgcag cctctggatt caccttcaat aagaatgcca tgaattgggt ccgccaggct   120
ccaggaaagg gtttggaatg ggttgctcgc ataagaaata aaactaataa ttatgcaaca   180
tattatgccg attcagtgaa agccaggttt accatctcca gagatgattc acaaagcatg   240
ctctatctgc aaatgaacaa cttgaaaatt gaggacacag ccatgtacta ttgtgtggct   300
ggtaactcgt ttgcttactg gggccaaggg actctggtca ctgtctctgc a            351

<210> SEQ ID NO 8
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 8

Glu Val Gln Leu Val Glu Thr Gly Gly Gly Met Val Gln Pro Glu Gly
1               5                   10                  15

Ser Leu Lys Leu Ser Cys Ala Ala Ser Gly Phe Thr Phe Asn Lys Asn
            20                  25                  30

Ala Met Asn Trp Val Arg Gln Ala Pro Gly Lys Gly Leu Glu Trp Val
        35                  40                  45

Ala Arg Ile Arg Asn Lys Thr Asn Asn Tyr Ala Thr Tyr Tyr Ala Asp
    50                  55                  60

Ser Val Lys Ala Arg Phe Thr Ile Ser Arg Asp Asp Ser Gln Ser Met
65                  70                  75                  80

Leu Tyr Leu Gln Met Asn Asn Leu Lys Ile Glu Asp Thr Ala Met Tyr
                85                  90                  95

Tyr Cys Val Ala Gly Asn Ser Phe Ala Tyr Trp Gly Gln Gly Thr Leu
            100                 105                 110

Val Thr Val Ser Ala
        115

<210> SEQ ID NO 9
<211> LENGTH: 339
<212> TYPE: DNA
```

<213> ORGANISM: Artificial Sequence
<220> FEATURE:
<223> OTHER INFORMATION: Synthetic polynucleotide

<400> SEQUENCE: 9

```
gacattgtga tgtcacagtc tccatcctcc ctagttgtgt caattggaga gaaggttact      60
atgacctgca agtccagtca gagccttttta tatagcagca atcaaaagaa ctacttggcc    120
tggtaccaac agaaaccagg gcagtctcct aaactgctga tttactgggc atccagtagg    180
gaatctgggg tccctgatcg cttcacaggc agtggatctg ggacagattt cactctcacc    240
atcagcagtg tgaaggctga agacctggca gtttattact gtcagcaata ttataactat    300
ccgctcacgt tcggtgctgg gaccaagttg gagctgaaa                           339
```

<210> SEQ ID NO 10
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 10

```
Asp Ile Val Met Ser Gln Ser Pro Ser Ser Leu Val Val Ser Ile Gly
1               5                   10                  15
Glu Lys Val Thr Met Thr Cys Lys Ser Ser Gln Ser Leu Leu Tyr Ser
            20                  25                  30
Ser Asn Gln Lys Asn Tyr Leu Ala Trp Tyr Gln Gln Lys Pro Gly Gln
        35                  40                  45
Ser Pro Lys Leu Leu Ile Tyr Trp Ala Ser Ser Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Lys Ala Glu Asp Leu Ala Val Tyr Tyr Cys Gln Gln
                85                  90                  95
Tyr Tyr Asn Tyr Pro Leu Thr Phe Gly Ala Gly Thr Lys Leu Glu Leu
            100                 105                 110
Lys
```

<210> SEQ ID NO 11
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 11

```
gaggtgcagc ttgttgagac tggcggagga ttggtgcagc ctgaagggtc attgaaactc      60
tcatgtgcaa cgtctggatt caacttcaat accaatgcca tgaactgggt ccgccaggct    120
ccaggaaagg gtttggaatg ggttgctcgc ataagaaata aaactaataa ttatgcaaca    180
tattatgccg attcagtgaa agacaggttc accatctcca gagatgattc acaaagaatg    240
gtctttctgc aaatgaataa cttgaaaact gaggacacag ccatctatta ctgtgtggcg    300
gggaactcgt tgcttattg gggccaaggg actctggtca ctgtctctcc t             351
```

<210> SEQ ID NO 12
<211> LENGTH: 117
<212> TYPE: PRT
<213> ORGANISM: Artificial Sequence
<220> FEATURE:

<223> OTHER INFORMATION: Synthetic polypeptide

<400> SEQUENCE: 12

Glu Val Gln Leu Val Glu Thr Gly Gly Gly Leu Val Gln Pro Glu Gly
1               5                   10                  15

Ser Leu Lys Leu Ser Cys Ala Thr Ser Gly Phe Asn Phe Asn Thr Asn
            20                  25                  30

Ala Met Asn Trp Val Arg Gln Ala Pro Gly Lys Gly Leu Glu Trp Val
        35                  40                  45

Ala Arg Val Arg Asn Lys Thr Asn Asn Tyr Ala Thr Tyr Tyr Ala Asp
    50                  55                  60

Ser Val Lys Asp Arg Phe Thr Ile Ser Arg Asp Asp Ser Gln Arg Met
65                  70                  75                  80

Val Phe Leu Gln Met Asn Asn Leu Lys Thr Glu Asp Thr Ala Ile Tyr
                85                  90                  95

Tyr Cys Val Ala Gly Asn Ser Phe Ala Tyr Trp Gly Gln Gly Thr Leu
            100                 105                 110

Val Thr Val Ser Pro
        115

<210> SEQ ID NO 13
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 13
gacattgtga tgtcacagtc tccatcctcc ctagctgtgt cagttggaga gagggttact      60
atgaactgca gtccagtca gagtctttta tatagtagca atcaaaagaa ctacttggcc     120
tggtaccagc agaaaccagg gcagtctcct aaactgctga tttactgggc atccactagg    180
gaatctgggg tccctgatcg cttcacaggc agtgtatctg ggacagattt cactctcacc    240
atcagcagtg tgaaggctga agacctggca gtttattact gtcagcaata ttataactat    300
ccgctcacgt tcggtgctgg gaccaagctg gagctgaaa                            339

<210> SEQ ID NO 14
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 14

Asp Ile Val Met Ser Gln Ser Pro Ser Ser Leu Ala Val Ser Val Gly
1               5                   10                  15

Glu Arg Val Thr Met Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Val Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Ala Gly Thr Lys Leu Glu Leu

Lys

<210> SEQ ID NO 15
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 15

```
gaggtgcagc ttgttggaag tggtggagga ttggtgcagc ctgaagggtc attgaaactc      60
tcatgtgcag cctctggatt caccttcaag accaatgcca tgaactgggt ccgccaggct     120
ccaggaaagg gtttggaatg ggttgctcgc ataagaaata aaactaataa ttatgcaaca     180
tattatgccg actcagtgaa agacaggttc accatctcca gagatgattc acaaagcatg     240
ctctatctgc aaatgaacaa cttgaaaact gaagacacag ccatgtattt ctgtgtggcc     300
ggtaactcgt ttgcttactg gggccagggg actctggtca ctgtctctgc a              351
```

<210> SEQ ID NO 16
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 16

Glu Val Gln Leu Val Gly Ser Gly Gly Gly Leu Val Gln Pro Glu Gly
1               5                   10                  15
Ser Leu Lys Leu Ser Cys Ala Ala Ser Gly Phe Thr Phe Lys Thr Asn
            20                  25                  30
Ala Met Asn Trp Val Arg Gln Ala Pro Gly Lys Gly Leu Glu Trp Val
        35                  40                  45
Ala Arg Ile Arg Asn Lys Thr Asn Asn Tyr Ala Thr Tyr Tyr Ala Asp
    50                  55                  60
Ser Val Lys Asp Arg Phe Thr Ile Ser Arg Asp Asp Ser Gln Ser Met
65                  70                  75                  80
Leu Tyr Leu Gln Met Asn Asn Leu Lys Thr Glu Asp Thr Ala Met Tyr
                85                  90                  95
Phe Cys Val Ala Gly Asn Ser Phe Ala Tyr Trp Gly Gln Gly Thr Leu
            100                 105                 110
Val Thr Val Ser Ala
        115

<210> SEQ ID NO 17
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 17

```
gacattgtga tgtcacagtc tccatcctcc ctagctgtgt cagttggaga gaaggttact      60
gtgaactgca agtccagtca gagccttta tatagtaaca atcaaaagaa ctacttggcc     120
tggtaccagc agaaaccagg gcagtctcct aaactgctga tttactgggc atcaactagg     180
gaatatgggg tccctgatcg cttcacaggc agtggatctg gacagatttc actctcacc     240
atcagcagtg tgaaggctga agacctggca gtttattact gtcagcaata ttataactat     300
```

```
ccgctcacgt tcggtgctgg gaccaagctg gagctgaaa                            339
```

```
<210> SEQ ID NO 18
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 18
```

Asp Ile Val Met Ser Gln Ser Pro Ser Ser Leu Ala Val Ser Val Gly
1               5                   10                  15

Glu Lys Val Thr Val Asn Cys Lys Ser Ser Gln Ser Leu Leu Tyr Ser
            20                  25                  30

Asn Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Tyr Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Asn Tyr Pro Leu Thr Phe Gly Ala Gly Thr Lys Leu Glu Leu
            100                 105                 110

Lys

```
<210> SEQ ID NO 19
<211> LENGTH: 351
<212> TYPE: DNA
<213> ORGANISM: Artificial Sequence
<220> FEATURE:
<223> OTHER INFORMATION: Synthetic polynucleotide
<400> SEQUENCE: 19
gaggtccagc ttgttgagac tggtggagga ttggtgcagc ctaaagggtc attgaaactc    60
tcatgtgcag cctctggatt caccttcaat accaatgcca tgaactgggt ccgccaggct   120
ccaggaaagg gtttgcaatg ggttgctcgc gtaagaaata aaactaataa ttatgcaaca   180
tattatgccg attccgtgaa agacaggttc accatctcca gagatgattc acaaagcatg   240
ctctatctgc aaatgaacaa cttgaaaact gaagacacgg ccatttatta ctgtgtgggg   300
ggtaactcgt ttgcttactg gggccaaggg actctggtca ctgtctctgc a            351
```

```
<210> SEQ ID NO 20
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 20
```

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Gln Trp Val
        35                  40                  45

Ala Arg Val Arg Asn Lys Thr Asn Asn Tyr Ala Thr Tyr Tyr Ala Asp
    50                  55                  60

```
Ser Val Lys Asp Arg Phe Thr Ile Ser Arg Asp Asp Ser Gln Ser Met
 65                  70                  75                  80

Leu Tyr Leu Gln Met Asn Asn Leu Lys Thr Glu Asp Thr Ala Ile Tyr
                 85                  90                  95

Tyr Cys Val Gly Gly Asn Ser Phe Ala Tyr Trp Gly Gln Gly Thr Leu
            100                 105                 110

Val Thr Val Ser Ala
        115

<210> SEQ ID NO 21
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 21
gacattgtga tgtcccagtc tccatcctcc ctagctgtgt cagttggaga gaaggttact     60
atgagctgca agtccagtca gagccttttta tatagtaaca atcaaaagaa ctacttggcc    120
tggtaccacc agaaaccagg gcagtctcct aaactgctga tttactgggc atccactagg    180
gaatctgggg tccctgatcg cttcacaggc agtggatctg gacagattt cactctcacc     240 atcagcagtg tgaaggctga agacctggca gtttattact gtcagcaata ttatagctat    300
ccactcacgt tcggtgctgg gaccaagctg gagctgaaa                           339

<210> SEQ ID NO 22
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 22

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                 20                  25                  30

Asn Asn Gln Lys Asn Tyr Leu Ala Trp Tyr His Gln Lys Pro Gly Gln
             35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys

<210> SEQ ID NO 23
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 23
gacattgtga tgtcccagtc tccatcctcc ctagctgtgt cagttggaga gaaggttact     60
```

```
atgagctgca agtccagtca gagccttta tatagtaaca atcaaaagaa ctacttggcc    120
tggtaccacc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttatatctat    300
ccactcacgt tcggtgctgg gaccaagctg gagctgaaa                           339
```

```
<210> SEQ ID NO 24
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 24
```

```
Asp Ile Val Met Ser Gln Ser Pro Ser Ser Leu Ala Val Ser Val Gly
  1               5                  10                  15

Glu Lys Val Thr Met Ser Cys Lys Ser Ser Gln Ser Leu Leu Tyr Ser
             20                  25                  30

Asn Asn Gln Lys Asn Tyr Leu Ala Trp Tyr His Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ile Tyr Pro Leu Thr Phe Gly Ala Gly Thr Lys Leu Glu Leu
            100                 105                 110

Lys
```

```
<210> SEQ ID NO 25
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 25
```

```
gacattgtga tgtcccagtc tccatcctcc ctagctgtgt cagttggaga gaaggttact    60
atgagctgca agtccagtca gagccttta tatagtaaca atcaaaagaa ctacttggcc    120
tggtaccacc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttatagctat    300
ccactcacgt tcggtgctgg gaccaagctg gaaataaaa                           339
```

```
<210> SEQ ID NO 26
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 26
```

```
Asp Ile Val Met Ser Gln Ser Pro Ser Ser Leu Ala Val Ser Val Gly
  1               5                  10                  15
```

Glu Lys Val Thr Met Ser Cys Lys Ser Ser Gln Ser Leu Leu Tyr Ser
            20                  25                  30

Asn Asn Gln Lys Asn Tyr Leu Ala Trp Tyr His Gln Lys Pro Gly Gln
        35                  40                  45

Ser Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Ile
            100                 105                 110

Lys

<210> SEQ ID NO 27
<211> LENGTH: 1797
<212> TYPE: DNA
<213> ORGANISM: Artificial Sequence
<220> FEATURE:
<223> OTHER INFORMATION: Synthetic polynucleotide

<400> SEQUENCE: 27

```
atggaggtgc agcttgttga gactggtgga ggaatggtgc agcctgaagg gtcattgaaa      60
ctctcatgtg cagcctctgg attcaccttc aataagaatg ccatgaattg ggtccgccag     120
gctccaggaa agggtttgga atgggttgct cgcataagaa ataaaactaa taattatgca     180
acatattatg ccgattcagt gaaagccagg tttaccatct ccagagatga ttcacaaagc     240
atgctctatc tgcaaatgaa caacttgaaa attgaggaca cagccatgta ctattgtgtg     300
gctggtaact cgtttgctta ctggggccaa gggactctgg tcactgtctc tgcaggcgga     360
ggcggatcag gtggtggcgg atctggaggt ggcggaagcg acattgtgat gtcacagtct     420
ccatcctccc tagttgtgtc aattggagag aaggttacta tgacctgcaa gtccagtcag     480
agccttttat atagcagcaa tcaaaagaac tacttggcct ggtaccaaca gaaaccaggg     540
cagtctccta aactgctgat ttactgggca tccagtaggg aatctggggt ccctgatcgc     600
ttcacaggca gtggatctgg gacagatttc actctcacca tcagcagtgt gaaggctgaa     660
gacctggcag tttattactg tcagcaatat tataactatc cgctcacgtt cggtgctggg     720
accaagttgg agctgaaagc ttccggaggt cccgagggcg cagcctggc cgcgctgacc     780
gcgcaccagg cttgccacct gccgctggag actttcaccc gtcatcgcca gccgcgcggc     840
tgggaacaac tggagcagtg cggctatccg gtgcagcggc tggtcgccct ctacctggcg     900
gcgcggctgt cgtggaacca ggtcgaccag gtgatccgca acgccctggc cagccccggc     960
agcggcggcg acctgggcga agcgatccgc gagcagccgg agcaggcccg tctggccctg    1020
accctggccg ccgccgagag cgagcgcttc gtccggcagg gcaccggcaa cgacgaggcc    1080
ggcgcggcca acgcccggc ggacagcggc gacgccctgc tggagcgcaa ctatcccact    1140
ggcgcggagt tcctcggcga cggcggcgac gtcagcttca gcacccgcgg cacgcagaac    1200
tggacggtgg agcggctgct ccaggcgcac cgccaactgg aggagcgcgg ctatgtgttc    1260
gtcggctacc acggcacctt cctcgaagcg gcgcaaagca tcgtcttcgg cggggtgcgc    1320
gcgcgcagcc aggacctcga cgcgatctgg cgcggtttct atatcgccgg cgatccggcg    1380
ctggcctacg gctacgccca ggaccaggaa cccgacgcac gcggccggat ccgcaacggt    1440
gccctgctgc gggtctatgt gccgcgctcg agcctgccgg gcttctaccg caccagcctg    1500
```

-continued

```
accctggccg cgccggaggc ggcgggcgag gtcgaacggc tgatcggcca tccgctgccg    1560
ctgcgcctgg acgccatcac cggccccgag gaggaaggcg ggcgcctgga gaccattctc    1620
ggctggccgc tggccgagcg caccgtggtg attccctcgg cgatccccac cgacccgcgc    1680
aacgtcggcg cgacctcga cccgtccagc atccccgaca ggaacaggc gatcagcgcc    1740 ctgccggact acgccagcca gcccggcaaa ccgccgcgcg aggacctgaa gtaactg      1797
```

<210> SEQ ID NO 28
<211> LENGTH: 597
<212> TYPE: PRT
<213> ORGANISM: Artificial Sequence
<220> FEATURE:
<223> OTHER INFORMATION: Synthetic polypeptide

<400> SEQUENCE: 28

```
Met Glu Val Gln Leu Val Glu Thr Gly Gly Gly Met Val Gln Pro Glu
1               5                   10                  15

Gly Ser Leu Lys Leu Ser Cys Ala Ala Ser Gly Phe Thr Phe Asn Lys
            20                  25                  30

Asn Ala Met Asn Trp Val Arg Gln Ala Pro Gly Lys Gly Leu Glu Trp
        35                  40                  45

Val Ala Arg Ile Arg Asn Lys Thr Asn Asn Tyr Ala Thr Tyr Tyr Ala
    50                  55                  60

Asp Ser Val Lys Ala Arg Phe Thr Ile Ser Arg Asp Asp Ser Gln Ser
65                  70                  75                  80

Met Leu Tyr Leu Gln Met Asn Asn Leu Lys Ile Glu Asp Thr Ala Met
                85                  90                  95

Tyr Tyr Cys Val Ala Gly Asn Ser Phe Ala Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asp Ile Val Met Ser Gln Ser Pro Ser Ser Leu
    130                 135                 140

Val Val Ser Ile Gly Glu Lys Val Thr Met Thr Cys Lys Ser Ser Gln
145                 150                 155                 160

Ser Leu Leu Tyr Ser Ser Asn Gln Lys Asn Tyr Leu Ala Trp Tyr Gln
                165                 170                 175

Gln Lys Pro Gly Gln Ser Pro Lys Leu Leu Ile Tyr Trp Ala Ser Ser
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Lys Ala Glu Asp Leu Ala Val
    210                 215                 220

Tyr Tyr Cys Gln Gln Tyr Tyr Asn Tyr Pro Leu Thr Phe Gly Ala Gly
225                 230                 235                 240

Thr Lys Leu Glu Leu Lys Ala Ser Gly Gly Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Leu Leu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
```

```
                305                 310                 315                 320
Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
                340                 345                 350

Gln Gly Thr Gly Asn Asp Glu Ala Gly Ala Ala Asn Gly Pro Ala Asp
                355                 360                 365

Ser Gly Asp Ala Leu Leu Glu Arg Asn Tyr Pro Thr Gly Ala Glu Phe
                370                 375                 380

Leu Gly Asp Gly Gly Asp Val Ser Phe Ser Thr Arg Gly Thr Gln Asn
385                 390                 395                 400

Trp Thr Val Glu Arg Leu Leu Gln Ala His Arg Gln Leu Glu Glu Arg
                405                 410                 415

Gly Tyr Val Phe Val Gly Tyr His Gly Thr Phe Leu Glu Ala Ala Gln
                420                 425                 430

Ser Ile Val Phe Gly Gly Val Arg Ala Arg Ser Gln Asp Leu Asp Ala
                435                 440                 445

Ile Trp Arg Gly Phe Tyr Ile Ala Gly Asp Pro Ala Leu Ala Tyr Gly
                450                 455                 460

Tyr Ala Gln Asp Gln Glu Pro Asp Ala Arg Gly Arg Ile Arg Asn Gly
465                 470                 475                 480

Ala Leu Leu Arg Val Tyr Val Pro Arg Ser Ser Leu Pro Gly Phe Tyr
                485                 490                 495

Arg Thr Ser Leu Thr Leu Ala Ala Pro Glu Ala Ala Gly Glu Val Glu
                500                 505                 510

Arg Leu Ile Gly His Pro Leu Pro Leu Arg Leu Asp Ala Ile Thr Gly
                515                 520                 525

Pro Glu Glu Gly Gly Arg Leu Glu Thr Ile Leu Gly Trp Pro Leu
                530                 535                 540

Ala Glu Arg Thr Val Val Ile Pro Ser Ala Ile Pro Thr Asp Pro Arg
545                 550                 555                 560

Asn Val Gly Gly Asp Leu Asp Pro Ser Ser Ile Pro Asp Lys Glu Gln
                565                 570                 575

Ala Ile Ser Ala Leu Pro Asp Tyr Ala Ser Gln Pro Gly Lys Pro Pro
                580                 585                 590

Arg Glu Asp Leu Lys
                595

<210> SEQ ID NO 29
<211> LENGTH: 613
<212> TYPE: PRT
<213> ORGANISM: Pseudomonas aeruginosa

<400> SEQUENCE: 29

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
                35                  40                  45

Leu Glu Gly Gly Asn Asp Ala Leu Lys Leu Ala Ile Asp Asn Ala Leu
            50                  55                  60

Ser Ile Thr Ser Asp Gly Leu Thr Ile Arg Leu Glu Gly Gly Val Glu
65              70                  75                  80
```

```
Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
            130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
                180                 185                 190

Gly Lys Val Leu Cys Leu Leu Asp Pro Leu Asp Gly Val Tyr Asn Tyr
                195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
            275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
            355                 360                 365

Ser Leu Thr Cys Pro Val Ala Ala Gly Glu Cys Ala Gly Pro Ala Asp
            370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
            435                 440                 445

Ser Ile Val Phe Gly Gly Val Arg Ala Arg Ser Gln Asp Leu Asp Ala
            450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
```

```
                500                 505                 510
Arg Thr Ser Leu Thr Leu Ala Ala Pro Glu Ala Ala Gly Glu Val Glu
                515                 520                 525

Arg Leu Ile Gly His Pro Leu Pro Leu Arg Leu Asp Ala Ile Thr Gly
            530                 535                 540

Pro Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 30
<211> LENGTH: 1800
<212> TYPE: DNA
<213> ORGANISM: Artificial Sequence
<220> FEATURE:
<223> OTHER INFORMATION: Synthetic polynucleotide

<400> SEQUENCE: 30
atggaggtgc agcttgttgg aagtggtgga ggattggtgc agcctgaagg gtcattgaaa      60
ctctcatgtg cagcctctgg attcaccttc aagaccaatg ccatgaactg ggtccgccag     120
gctccaggaa agggtttgga atgggttgct cgcataagaa ataaaactaa taattatgca     180
acatattatg ccgactcagt gaaagacagg ttcaccatct ccagagatga ttcacaaagc     240
atgctctatc tgcaaatgaa caacttgaaa actgaagaca cagccatgta tttctgtgtg     300
gccggtaact cgtttgctta ctggggccag gggactctgg tcactgtctc tgcaggcgga     360
ggcggatcag gtggtggcgg atctggaggt ggcggaagcg acattgtgat gtcacagtct     420
ccatcctccc tagctgtgtc agttggagag aaggttactg tgaactgcaa gtccagtcag     480
agccttttat atagtaacaa tcaaaagaac tacttggcct ggtaccagca gaaaccaggg     540
cagtctccta aactgctgat ttactgggca tcaactaggg aatatggggt ccctgatcgc     600
ttcacaggca gtggatctgg gacagatttc actctcacca tcagcagtgt gaaggctgaa     660
gacctggcag tttattactg tcagcaatat tataactatc cgctcacgtt cggtgctggg     720
accaagctgg agctgaaagc ttccggaggt cccgagggcg cagcctggc cgcgctgacc     780
gcgcaccagg cttgccacct gccgctggag actttcaccc gtcatcgcca ccgcgcggc     840
tgggaacaac tggagcagtg cggctatccg gtgcagcggc tggtcgccct ctacctggcg     900
gcgcggctgt cgtggaacca ggtcgaccag gtgatccgca acgccctggc cagccccggc     960
agcggcggcg acctgggcga agcgatccgc gagcagccgg agcaggcccg tctggccctg    1020
accctggccg ccgccgagag cgagcgcttc gtccggcagg caccggcaa cgacgaggcc    1080
ggcgcggcca acggcccggc ggacagcggc gacgccctgc tggagcgcaa ctatcccact    1140
ggcgcggagt cctcggcga cggcggcgac gtcagcttca gcaccgcgg cacgcagaac    1200
tggacggtgg agcggctgct ccaggcgcac cgccaactgg aggagcgcgg ctatgtgttc    1260
gtcggctacc acggcacctt cctcgaagcg cgcaaagca tcgtcttcgg cggggtgcgc    1320
gcgcgcagcc aggacctcga cgcgatctgg cgcggtttct atatcgccgg cgatccggcg    1380
```

```
ctggcctacg gctacgccca ggaccaggaa cccgacgcac gcggccggat ccgcaacggt   1440
gccctgctgc gggtctatgt gccgcgctcg agcctgccgg gcttctaccg caccagcctg   1500
accctggccg cgccggaggc ggcgggcgag gtcgaacggc tgatcggcca tccgctgccg   1560
ctgcgcctgg acgccatcac cggccccgag gaggaaggcg ggcgcctgga gaccattctc   1620
ggctggccgc tggccgagcg caccgtggtg attccctcgg cgatccccac cgacccgcgc   1680
aacgtcggcg cgacctcga cccgtccagc atccccgaca aggaacaggc gatcagcgcc   1740
ctgccggact acgccagcca gcccggcaaa ccgccgcgcg aggacctgaa gtaactgccg   1800
```

<210> SEQ ID NO 31
<211> LENGTH: 597
<212> TYPE: PRT
<213> ORGANISM: Artificial Sequence
<220> FEATURE:
<223> OTHER INFORMATION: Synthetic polypeptide

<400> SEQUENCE: 31

```
Met Glu Val Gln Leu Val Gly Ser Gly Gly Leu Val Gln Pro Glu
1               5                   10                  15

Gly Ser Leu Lys Leu Ser Cys Ala Ala Ser Gly Phe Thr Phe Lys Thr
                20                  25                  30

Asn Ala Met Asn Trp Val Arg Gln Ala Pro Gly Lys Gly Leu Glu Trp
            35                  40                  45

Val Ala Arg Ile Arg Asn Lys Thr Asn Asn Tyr Ala Thr Tyr Tyr Ala
        50                  55                  60

Asp Ser Val Lys Asp Arg Phe Thr Ile Ser Arg Asp Asp Ser Gln Ser
65                  70                  75                  80

Met Leu Tyr Leu Gln Met Asn Asn Leu Lys Thr Glu Asp Thr Ala Met
                85                  90                  95

Tyr Phe Cys Val Ala Gly Asn Ser Phe Ala Tyr Trp Gly Gln Gly Thr
            100                 105                 110

Leu Val Thr Val Ser Ala Gly Gly Gly Gly Ser Gly Gly Gly Gly Ser
        115                 120                 125

Gly Gly Gly Gly Ser Asp Ile Val Met Ser Gln Ser Pro Ser Ser Leu
130                 135                 140

Ala Val Ser Val Gly Glu Lys Val Thr Val Asn Cys Lys Ser Ser Gln
145                 150                 155                 160

Ser Leu Leu Tyr Ser Asn Asn Gln Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Tyr Gly Val Pro Asp Arg Phe Thr Gly Ser Gly Ser Gly Thr
        195                 200                 205

Asp Phe Thr Leu Thr Ile Ser Ser Val Lys Ala Glu Asp Leu Ala Val
    210                 215                 220

Tyr Tyr Cys Gln Gln Tyr Tyr Asn Tyr Pro Leu Thr Phe Gly Ala Gly
225                 230                 235                 240

Thr Lys Leu Glu Leu Lys Ala Ser Gly Gly Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
```

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
            325                 330                 335

Arg Leu Ala Leu Thr Leu Ala Ala Glu Ser Glu Arg Phe Val Arg
        340                 345                 350

Gln Gly Thr Gly Asn Asp Glu Ala Gly Ala Asn Gly Pro Ala Asp
    355                 360                 365

Ser Gly Asp Ala Leu Leu Glu Arg Asn Tyr Pro Thr Gly Ala Glu Phe
370                 375                 380

Leu Gly Asp Gly Gly Asp Val Ser Phe Ser Thr Arg Gly Thr Gln Asn
385                 390                 395                 400

Trp Thr Val Glu Arg Leu Leu Gln Ala His Arg Gln Leu Glu Glu Arg
                405                 410                 415

Gly Tyr Val Phe Val Gly Tyr His Gly Thr Phe Leu Glu Ala Ala Gln
            420                 425                 430

Ser Ile Val Phe Gly Gly Val Arg Ala Arg Ser Gln Asp Leu Asp Ala
        435                 440                 445

Ile Trp Arg Gly Phe Tyr Ile Ala Gly Asp Pro Ala Leu Ala Tyr Gly
    450                 455                 460

Tyr Ala Gln Asp Gln Glu Pro Asp Ala Arg Gly Arg Ile Arg Asn Gly
465                 470                 475                 480

Ala Leu Leu Arg Val Tyr Val Pro Arg Ser Ser Leu Pro Gly Phe Tyr
                485                 490                 495

Arg Thr Ser Leu Thr Leu Ala Ala Pro Glu Ala Ala Gly Glu Val Glu
            500                 505                 510

Arg Leu Ile Gly His Pro Leu Pro Leu Arg Leu Asp Ala Ile Thr Gly
        515                 520                 525

Pro Glu Glu Glu Gly Gly Arg Leu Glu Thr Ile Leu Gly Trp Pro Leu
    530                 535                 540

Ala Glu Arg Thr Val Val Ile Pro Ser Ala Ile Pro Thr Asp Pro Arg
545                 550                 555                 560

Asn Val Gly Gly Asp Leu Asp Pro Ser Ser Ile Pro Asp Lys Glu Gln
                565                 570                 575

Ala Ile Ser Ala Leu Pro Asp Tyr Ala Ser Gln Pro Gly Lys Pro Pro
            580                 585                 590

Arg Glu Asp Leu Lys
        595

<210> SEQ ID NO 32
<211> LENGTH: 1800
<212> TYPE: DNA
<213> ORGANISM: Artificial Sequence
<220> FEATURE:
<223> OTHER INFORMATION: Synthetic polynucleotide

<400> SEQUENCE: 32
atggaggtgc agcttgttga gactggtgga ggattggtgc agcctaaagg gtcattgaaa      60
ctctcatgtg cagcctctgg attcaccttc aataccaatg ccatgaactg ggtccgccag     120
gctccaggaa agggtttgca atgggttgct cgcgtaagaa ataaaactaa taattatgca     180
acatattatg ccgattccgt gaaagacagg ttcaccatct ccagagatga ttcacaaagc     240
atgctctatc tgcaaatgaa caacttgaaa actgaagaca cggccattta ttactgtgtg     300

```
ggggtaact cgtttgctta ctggggccaa gggactctgg tcactgtctc tgcaggcgga      360
ggcggatcag gtggtggcgg atctggaggt ggcggaagcg acattgtgat gtcccagtct      420
ccatcctccc tagctgtgtc agttggagag aaggttacta tgagctgcaa gtccagtcag      480
agccttttat atagtaacaa tcaaaagaac tacttggcct ggtaccacca gaaaccaggg      540
cagtctccta aactgctgat ttactgggca tccactaggg aatctggggt ccctgatcgc      600
ttcacaggca gtggatctgg gacagatttc actctcacca tcagcagtgt gaaggctgaa      660
gacctggcag tttattactg tcagcaatat tatagctatc cactcacgtt cggtgctggg      720
accaagctgg agctgaaagc ttccggaggt cccgagggcg cagcctggc cgcgctgacc      780
gcgcaccagg cttgccacct gccgctggag actttcaccc gtcatcgcca gccgcgcggc      840
tgggaacaac tggagcagtg cggctatccg gtgcagcggc tggtcgccct ctacctggcg      900
gcgcggctgt cgtggaacca ggtcgaccag gtgatccgca cgccctggc cagccccggc      960
agcggcggcg acctgggcga agcgatccgc gagcagccgg agcaggcccg tctggccctg     1020
accctggccg ccgccgagag cgagcgcttc gtccggcagg gcaccggcaa cgacgaggcc     1080
ggcgcggcca acggcccggc ggacagcggc gacgccctgc tggagcgcaa ctatcccact     1140
ggcgcggagt tcctcggcga cggcggcgac gtcagcttca gcaccgcgg cacgcagaac     1200
tggacggtgg agcggctgct ccaggcgcac cgccaactgg aggagcgcgg ctatgtgttc     1260
gtcggctacc acggcacctt cctcgaagcg gcgcaaagca tcgtcttcgg cggggtgcgc     1320
gcgcgcagcc aggacctcga cgcgatctgg cgcggtttct atatcgccgg cgatccggcg     1380
ctggcctacg gctacgccca ggaccaggaa cccgacgcac gcggccggat ccgcaacggt     1440
gccctgctgc gggtctatgt gccgcgctcg agcctgccgg gcttctaccg caccagcctg     1500
accctggccg cgccggaggc ggcgggcgag gtcgaacggc tgatcggcca tccgctgccg     1560
ctgcgcctgg acgccatcac cggccccgag gaggaaggcg ggcgcctgga gaccattctc     1620
ggctggccgc tggccgagcg caccgtggtg attccctcgg cgatccccac cgacccgcgc     1680
aacgtcggcg gcgacctcga cccgtccagc atccccgaca ggaacaggc gatcagcgcc     1740
ctgccggact acgccagcca gcccggcaaa ccgccgcgcg aggacctgaa gtaactgccg     1800
```

<210> SEQ ID NO 33
<211> LENGTH: 597
<212> TYPE: PRT
<213> ORGANISM: Artificial Sequence
<220> FEATURE:
<223> OTHER INFORMATION: Synthetic polypeptide

<400> SEQUENCE: 33

```
Met Glu Val Gln Leu Val Glu Thr Gly Gly Gly Leu Val Gln Pro Lys
1               5                   10                  15

Gly Ser Leu Lys Leu Ser Cys Ala Ala Ser Gly Phe Thr Phe Asn Thr
            20                  25                  30

Asn Ala Met Asn Trp Val Arg Gln Ala Pro Gly Lys Gly Leu Gln Trp
        35                  40                  45

Val Ala Arg Val Arg Asn Lys Thr Asn Asn Tyr Ala Thr Tyr Tyr Ala
    50                  55                  60

Asp Ser Val Lys Asp Arg Phe Thr Ile Ser Arg Asp Asp Ser Gln Ser
65                  70                  75                  80

Met Leu Tyr Leu Gln Met Asn Asn Leu Lys Thr Glu Asp Thr Ala Ile
                85                  90                  95

Tyr Tyr Cys Val Gly Gly Asn Ser Phe Ala Tyr Trp Gly Gln Gly Thr
```

```
              100             105                 110
Leu Val Thr Val Ser Ala Gly Gly Gly Gly Gly Gly Ser
        115                 120             125
Gly Gly Gly Gly Ser Asp Ile Val Met Ser Gln Ser Ser Leu
    130                 135             140
Ala Val Ser Val Gly Glu Lys Val Thr Met Ser Cys Lys Ser Ser Gln
145                 150                 155                 160
Ser Leu Leu Tyr Ser Asn Asn Gln Lys Asn Tyr Leu Ala Trp Tyr His
                165                 170                 175
Gln Lys Pro Gly Gln Ser Pro Lys Leu Leu Ile Tyr Trp Ala Ser Thr
            180                 185                 190
Arg Glu Ser Gly Val Pro Asp Arg Phe Thr Gly Ser Gly Ser Gly Thr
        195                 200                 205
Asp Phe Thr Leu Thr Ile Ser Ser Val Lys Ala Glu Asp Leu Ala Val
    210                 215                 220
Tyr Tyr Cys Gln Gln Tyr Tyr Ser Tyr Pro Leu Thr Phe Gly Ala Gly
225                 230                 235                 240
Thr Lys Leu Glu Leu Lys Ala Ser Gly Gly Pro Glu Gly Gly Ser Leu
                245                 250                 255
Ala Ala Leu Thr Ala His Gln Ala Cys His Leu Pro Leu Glu Thr Phe
            260                 265                 270
Thr Arg His Arg Gln Pro Arg Gly Trp Glu Gln Leu Glu Gln Cys Gly
        275                 280                 285
Tyr Pro Val Gln Arg Leu Val Ala Leu Tyr Leu Ala Ala Arg Leu Ser
    290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                325                 330                 335
Arg Leu Ala Leu Thr Leu Ala Ala Ala Glu Ser Glu Arg Phe Val Arg
            340                 345                 350
Gln Gly Thr Gly Asn Asp Glu Ala Gly Ala Ala Asn Gly Pro Ala Asp
        355                 360                 365
Ser Gly Asp Ala Leu Leu Glu Arg Asn Tyr Pro Thr Gly Ala Glu Phe
    370                 375                 380
Leu Gly Asp Gly Gly Asp Val Ser Phe Ser Thr Arg Gly Thr Gln Asn
385                 390                 395                 400
Trp Thr Val Glu Arg Leu Leu Gln Ala His Arg Gln Leu Glu Glu Arg
                405                 410                 415
Gly Tyr Val Phe Val Gly Tyr His Gly Thr Phe Leu Glu Ala Ala Gln
            420                 425                 430
Ser Ile Val Phe Gly Gly Val Arg Ala Arg Ser Gln Asp Leu Asp Ala
        435                 440                 445
Ile Trp Arg Gly Phe Tyr Ile Ala Gly Asp Pro Ala Leu Ala Tyr Gly
    450                 455                 460
Tyr Ala Gln Asp Gln Glu Pro Asp Ala Arg Gly Arg Ile Arg Asn Gly
465                 470                 475                 480
Ala Leu Leu Arg Val Tyr Val Pro Arg Ser Ser Leu Pro Gly Phe Tyr
                485                 490                 495
Arg Thr Ser Leu Thr Leu Ala Ala Pro Glu Ala Ala Gly Glu Val Glu
            500                 505                 510
Arg Leu Ile Gly His Pro Leu Pro Leu Arg Leu Asp Ala Ile Thr Gly
        515                 520                 525
```

```
Pro Glu Glu Glu Gly Gly Arg Leu Glu Thr Ile Leu Gly Trp Pro Leu
    530                 535                 540

Ala Glu Arg Thr Val Val Ile Pro Ser Ala Ile Pro Thr Asp Pro Arg
545                 550                 555                 560

Asn Val Gly Gly Asp Leu Asp Pro Ser Ser Ile Pro Asp Lys Glu Gln
                565                 570                 575

Ala Ile Ser Ala Leu Pro Asp Tyr Ala Ser Gln Pro Gly Lys Pro Pro
            580                 585                 590

Arg Glu Asp Leu Lys
        595

<210> SEQ ID NO 34
<211> LENGTH: 1797
<212> TYPE: DNA
<213> ORGANISM: Artificial Sequence
<220> FEATURE:
<223> OTHER INFORMATION: Synthetic polynucleotide

<400> SEQUENCE: 34
atggaggtgc agcttgttga gactggcgga ggattggtgc agcctgaagg gtcattgaaa      60
ctctcatgtg caacgtctgg attcaacttc aataccaatg ccatgaactg ggtccgccag     120
gctccaggaa agggtttgga atgggttgct cgcgtaagaa ataaaactaa taattatgca     180
acatattatg ccgattcagt gaaagacagg ttcaccatct ccagagatga ttcacaaaga     240
atggtctttc tgcaaatgaa taacttgaaa actgaggaca cagccatcta ttactgtgtg     300
gcggggaact cgtttgctta ttggggccaa gggactctgg tcactgtctc tcctggcgga     360
ggcggatcag gtggtggcgg atctggaggt ggcggaagcg acattgtgat gtcacagtct     420
ccatcctccc tagctgtgtc agttggagag agggttacta tgaactgcaa gtccagtcag     480
agtcttttat atagtagcaa tcaaaagaac tacttggcct ggtaccagca gaaaccaggg     540
cagtctccta aactgctgat ttactgggca tccactaggg aatctggggt ccctgatcgc     600
ttcacaggca gtgtatctgg gacagatttc actctcacca tcagcagtgt gaaggctgaa     660
gacctggcag tttattactg tcagcaatat tataactatc cgctcacgtt cggtgctggg     720
accaagctgg agctgaaagc ttccggaggt cccgagggcg gcagcctggc cgcgctgacc     780
gcgcaccagg cttgccacct gccgctggag actttcaccc gtcatcgcca gccgcgcggc     840
tgggaacaac tggagcagtg cggctatccg gtgcagcggc tggtcgccct ctacctggcg     900
gcgcggctgt cgtggaacca ggtcgaccag gtgatccgca cgccctggc cagccccggc     960 agcggcggcg acctgggcga agcgatccgc gagcagccgg agcaggcccg tctggccctg    1020
accctggccg ccgccgagag cgagcgcttc gtccggcagg gcaccggcaa cgacgaggcc    1080
ggcgcggcca acggcccggc ggacagcggc gacgccctgc tggagcgcaa ctatcccact    1140
ggcgcggagt cctcggcga cggcggcgac gtcagcttca gcacccgcgg cacgcagaac    1200
tggacggtgg agcggctgct ccaggcgcac cgccaactgg aggagcgcgg ctatgtgttc    1260
gtcggctacc acggcaccct cctcgaagcg gcgcaaagca tcgtcttcgg cggggtgcgc    1320
gcgcgcagcc aggacctcga cgcgatctgg cgcggtttct atatcgccgg cgatccggcg    1380
ctggcctacg gctacgccca ggaccaggaa cccgacgcac gcggccggat ccgcaacggt    1440
gccctgctgc gggtctatgt gccgcgctcg agcctgccgg gcttctaccg caccagcctg    1500
accctggccg cgccggaggc ggcgggcgag gtcgaacgc tgatcggcca tccgctgccg    1560
ctgcgcctgg acgccatcac cggccccgag gaggaaggcg gcgcctgga gaccattctc    1620
```

```
ggctggccgc tggccgagcg caccgtggtg attccctcgg cgatccccac cgacccgcgc    1680
aacgtcggcg cgacctcga cccgtccagc atccccgaca aggaacaggc gatcagcgcc     1740
ctgccggact acgccagcca gcccggcaaa ccgccgcgcg aggacctgaa gtaactg       1797
```

<210> SEQ ID NO 35
<211> LENGTH: 597
<212> TYPE: PRT
<213> ORGANISM: Artificial Sequence
<220> FEATURE:
<223> OTHER INFORMATION: Synthetic polypeptide

<400> SEQUENCE: 35

```
Met Glu Val Gln Leu Val Glu Thr Gly Gly Gly Leu Val Gln Pro Glu
1               5                   10                  15

Gly Ser Leu Lys Leu Ser Cys Ala Thr Ser Gly Phe Asn Phe Asn Thr
            20                  25                  30

Asn Ala Met Asn Trp Val Arg Gln Ala Pro Lys Gly Leu Glu Trp
        35                  40                  45

Val Ala Arg Val Arg Asn Lys Thr Asn Asn Tyr Ala Thr Tyr Tyr Ala
    50                  55                  60

Asp Ser Val Lys Asp Arg Phe Thr Ile Ser Arg Asp Asp Ser Gln Arg
65                  70                  75                  80

Met Val Phe Leu Gln Met Asn Asn Leu Lys Thr Glu Asp Thr Ala Ile
                85                  90                  95

Tyr Tyr Cys Val Ala Gly Asn Ser Phe Ala Tyr Trp Gly Gln Gly Thr
            100                 105                 110

Leu Val Thr Val Ser Pro Gly Gly Gly Ser Gly Gly Gly Gly Ser
        115                 120                 125

Gly Gly Gly Gly Ser Asp Ile Val Met Ser Gln Ser Pro Ser Ser Leu
    130                 135                 140

Ala Val Ser Val Gly Glu Arg Val Thr Met Asn Cys Lys Ser Ser Gln
145                 150                 155                 160

Ser Leu Leu Tyr Ser Ser Asn Gln Lys Asn Tyr Leu Ala Trp Tyr Gln
                165                 170                 175

Gln Lys Pro Gly Gln Ser Pro Lys Leu Leu Ile Tyr Trp Ala Ser Thr
            180                 185                 190

Arg Glu Ser Gly Val Pro Asp Arg Phe Thr Gly Ser Val Ser Gly Thr
        195                 200                 205

Asp Phe Thr Leu Thr Ile Ser Ser Val Lys Ala Glu Asp Leu Ala Val
    210                 215                 220

Tyr Tyr Cys Gln Gln Tyr Tyr Asn Tyr Pro Leu Thr Phe Gly Ala Gly
225                 230                 235                 240

Thr Lys Leu Glu Leu Lys Ala Ser Gly Gly Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335
```

```
Arg Leu Ala Leu Thr Leu Ala Ala Glu Ser Glu Arg Phe Val Arg
            340                 345                 350
Gln Gly Thr Gly Asn Asp Glu Ala Gly Ala Ala Asn Gly Pro Ala Asp
            355                 360                 365
Ser Gly Asp Ala Leu Leu Glu Arg Asn Tyr Pro Thr Gly Ala Glu Phe
            370                 375                 380
Leu Gly Asp Gly Gly Asp Val Ser Phe Ser Thr Arg Gly Thr Gln Asn
385                 390                 395                 400
Trp Thr Val Glu Arg Leu Leu Gln Ala His Arg Gln Leu Glu Glu Arg
                405                 410                 415
Gly Tyr Val Phe Val Gly Tyr His Gly Thr Phe Leu Glu Ala Ala Gln
                420                 425                 430
Ser Ile Val Phe Gly Gly Val Arg Ala Arg Ser Gln Asp Leu Asp Ala
                435                 440                 445
Ile Trp Arg Gly Phe Tyr Ile Ala Gly Asp Pro Ala Leu Ala Tyr Gly
            450                 455                 460
Tyr Ala Gln Asp Gln Glu Pro Asp Ala Arg Gly Arg Ile Arg Asn Gly
465                 470                 475                 480
Ala Leu Leu Arg Val Tyr Val Pro Arg Ser Ser Leu Pro Gly Phe Tyr
                485                 490                 495
Arg Thr Ser Leu Thr Leu Ala Ala Pro Glu Ala Ala Gly Glu Val Glu
                500                 505                 510
Arg Leu Ile Gly His Pro Leu Pro Leu Arg Leu Asp Ala Ile Thr Gly
                515                 520                 525
Pro Glu Glu Gly Gly Arg Leu Glu Thr Ile Leu Gly Trp Pro Leu
            530                 535                 540
Ala Glu Arg Thr Val Val Ile Pro Ser Ala Ile Pro Thr Asp Pro Arg
545                 550                 555                 560
Asn Val Gly Gly Asp Leu Asp Pro Ser Ser Ile Pro Asp Lys Glu Gln
                565                 570                 575
Ala Ile Ser Ala Leu Pro Asp Tyr Ala Ser Gln Pro Gly Lys Pro Pro
                580                 585                 590
Arg Glu Asp Leu Lys
            595

<210> SEQ ID NO 36
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 36
gaggtgcagc ttgttggaag tggtggagga ttggtgcagc ctgaagggtc attgaaactc      60
tcatgtgcag cctctggatt caccttcaag accaatgcca tgaactgggt ccgccaggct     120
ccaggaaagg gtttggaatg ggttgctcgc ataagaaata aaactaataa ttatgcaaca     180
tattatgccg actcagtgaa agacaggttc accatctcca gagatgattc acaaagcatg     240
ctctatctgc aaatgaacaa cttgaaaact gaagacacag ccatgtattt ctgtgtggcc     300
ggtaactcgt ttgcttactt gggccagggg actctggtca ctgtctctgc a             351

<210> SEQ ID NO 37
<211> LENGTH: 117
<212> TYPE: PRT
<213> ORGANISM: Artificial Sequence
```

<220> FEATURE:
<223> OTHER INFORMATION: Synthetic polypeptide

<400> SEQUENCE: 37

Glu Val Gln Leu Val Gly Ser Gly Gly Leu Val Gln Pro Glu Gly
1               5                   10                  15

Ser Leu Lys Leu Ser Cys Ala Ala Ser Gly Phe Thr Phe Lys Thr Asn
            20                  25                  30

Ala Met Asn Trp Val Arg Gln Ala Pro Gly Lys Gly Leu Glu Trp Val
        35                  40                  45

Ala Arg Ile Arg Asn Lys Thr Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Phe Cys Val Ala Gly Asn Ser Phe Ala Tyr Leu Gly Gln Gly Thr Leu
            100                 105                 110

Val Thr Val Ser Ala
            115

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = Thr or Asn
<220> FEATURE:
<221> NAME/KEY: MISC_FEATURE
<222> LOCATION: (5)..(5)
<223> OTHER INFORMATION: Xaa = Lys or Asn
<220> FEATURE:
<221> NAME/KEY: MISC_FEATURE
<222> LOCATION: (6)..(6)
<223> OTHER INFORMATION: Xaa = Thr or Lys

<400> SEQUENCE: 38

Gly Phe Xaa Phe Xaa Xaa Asn Ala
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Ile or Val

<400> SEQUENCE: 39

Xaa Arg Asn Lys Thr Asn Asn Tyr Ala Thr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic peptide
<220> FEATURE:

```
<221> NAME/KEY: MISC_FEATURE
<222> LOCATION: (2)..(2)
<223> OTHER INFORMATION: Xaa = Ala or Gly

<400> SEQUENCE: 40

Val Xaa Gly Asn Ser Phe Ala Tyr
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa = Thr or Lys

<400> SEQUENCE: 41

Xaa Asn Ala Met Asn
1               5

<210> SEQ ID NO 42
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Ile or Val
<220> FEATURE:
<221> NAME/KEY: MISC_FEATURE
<222> LOCATION: (19)..(19)
<223> OTHER INFORMATION: Xaa = Asp or Ala

<400> SEQUENCE: 42

Arg Xaa Arg Asn Lys Thr Asn Asn Tyr Ala Thr Tyr Tyr Ala Asp Ser
1               5                   10                  15

Val Lys Xaa

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide

<400> SEQUENCE: 43

Gly Asn Ser Phe Ala Tyr
1               5

<210> SEQ ID NO 44
<211> LENGTH: 12
<212> TYPE: PRT
<213> ORGANISM: Artificial Sequence
<220> FEATURE:
<223> OTHER INFORMATION: Synthetic peptide

<400> SEQUENCE: 44

Gln Ser Leu Leu Tyr Ser Asn Asn Gln Lys Asn Tyr
1               5                   10

<210> SEQ ID NO 45
<211> LENGTH: 9
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa = Ser, Ile or Asn

<400> SEQUENCE: 45

Gln Gln Tyr Tyr Xaa Tyr Pro Leu Thr
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic peptide

<400> SEQUENCE: 46

Lys Ser Ser Gln Ser Leu Leu Tyr Ser Asn Asn Gln Lys Asn Tyr Leu
1               5                   10                  15

Ala

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa = Thr or Ser
<220> FEATURE:
<221> NAME/KEY: MISC_FEATURE
<222> LOCATION: (7)..(7)
<223> OTHER INFORMATION: Xaa = Ser or Tyr

<400> SEQUENCE: 47

Trp Ala Ser Xaa Arg Glu Xaa
1               5
```